US012797264B2

(12) United States Patent
Schoon et al.

(10) Patent No.: US 12,797,264 B2
(45) Date of Patent: Nov. 17, 2026

(54) ABSORBENT STRUCTURES AND METHODS FOR MANUFACTURING ABSORBENT STRUCTURES

(71) Applicant: Kimberly-Clark Worldwide, Inc., Neenah, WI (US)

(72) Inventors: Bradley W. Schoon, Oshkosh, WI (US); Daniel T. Labash, Appleton, WI (US); Mark J. Beitz, Appleton, WI (US); David G. Biggs, New London, WI (US); Kate T. Bowen, Kaukauna, WI (US); Michelle L. Graverson, Appleton, WI (US); Andrew T. Baker, Norcross, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 517 days.

(21) Appl. No.: 18/042,585

(22) PCT Filed: Aug. 25, 2020

(86) PCT No.: PCT/US2020/047753
§ 371 (c)(1),
(2) Date: Feb. 22, 2023

(87) PCT Pub. No.: WO2022/046032
PCT Pub. Date: Mar. 3, 2022

(65) Prior Publication Data
US 2023/0329927 A1 Oct. 19, 2023

(51) Int. Cl.
*B29C 65/00* (2006.01)
*A61F 13/531* (2006.01)
(Continued)

(52) U.S. Cl.
CPC .. *A61F 13/531* (2013.01); *A61F 2013/15284* (2013.01); *A61F 2013/15829* (2013.01);
(Continued)

(58) Field of Classification Search
CPC ............................... B29C 65/48; A61F 13/531
See application file for complete search history.

(56) References Cited

U.S. PATENT DOCUMENTS 3,338,992 A 8/1967 Kinney
3,339,546 A 9/1967 Ling
(Continued)

FOREIGN PATENT DOCUMENTS

CN 1122150 A 5/1996
CN 1125391 A 6/1996
(Continued)

OTHER PUBLICATIONS

American Society for Testing Materials (ASTM) Designation: D1238-70, "Standard Method for Measuring Flow Rates of Thermoplastics by Extrusion Plastometer" Accessed copy from Sep. 11, 2006.
(Continued)

*Primary Examiner* — Philip C Tucker
*Assistant Examiner* — Nickolas R Harm
(74) *Attorney, Agent, or Firm* — KIMBERLY-CLARK WORLDWIDE, INC.

(57) ABSTRACT

Absorbent structures and methods of manufacture are disclosed. In one embodiment, an absorbent structure may comprise a first layer, a second layer, and a mixture of particles and adhesive between the first layer and the second layer, wherein the particles are disposed at greater than 400 gsm and less than 600 gsm, wherein the adhesive is disposed at greater than 4% and less than 6%, by weight, of the weight of the particles, wherein the adhesive forms a three-dimensional mesh network comprising network adhesive filaments
(Continued)

with the particles immobilized within the mesh network, and the network adhesive filaments extending substantially throughout a three-dimensional space defined by the network adhesive filaments and the particles, the structure having a Gray Level % Coefficient of Variability value (GL % COV) of less than or equal to 34.5, according to the Pad Uniformity Test Method.

15 Claims, 17 Drawing Sheets

(51) Int. Cl.
*A61F 13/15* (2006.01)
*A61F 13/53* (2006.01)
*B29C 65/48* (2006.01)

(52) U.S. Cl.
CPC ................. *A61F 2013/1591* (2013.01); *A61F 2013/530496* (2013.01); *B29C 65/48* (2013.01)

(56) References Cited

U.S. PATENT DOCUMENTS 3,341,394 A 9/1967 Kinney
3,485,706 A 12/1969 Evans
3,502,538 A 3/1970 Petersen
3,502,763 A 3/1970 Hartmann
3,542,615 A 11/1970 Dobo et al.
3,692,618 A 9/1972 Dorschner et al.
3,802,817 A 4/1974 Matsuki et al.
3,849,241 A 11/1974 Butin et al.
3,855,046 A 12/1974 Hansen et al.
3,901,236 A 8/1975 Assarsson et al.
3,966,865 A 6/1976 Nishida et al.
4,005,957 A 2/1977 Savich
4,055,180 A 10/1977 Karami
4,076,663 A 2/1978 Masuda et al.
4,100,324 A 7/1978 Anderson et al.
4,286,082 A 8/1981 Tsubakimoto et al.
4,340,563 A 7/1982 Appel et al.
4,369,156 A 1/1983 Mathes et al.
4,392,908 A 7/1983 Dehnel
4,427,737 A 1/1984 Cilento et al.
4,429,001 A 1/1984 Kolpin et al.
4,469,734 A 9/1984 Minto et al.
4,488,928 A 12/1984 Ali Khan et al.
4,530,353 A 7/1985 Lauritzen
4,542,199 A 9/1985 Kaminsky et al.
4,547,420 A 10/1985 Krueger et al.
4,551,191 A 11/1985 Kock et al.
4,585,448 A 4/1986 Enloe
4,587,154 A 5/1986 Hotchkiss et al.
4,588,630 A 5/1986 Shimalla
4,604,313 A 8/1986 McFarland et al.
4,654,038 A 3/1987 Sakurai
4,655,757 A 4/1987 McFarland et al.
4,666,647 A 5/1987 Enloe et al.
4,679,704 A 7/1987 Dunlop et al.
4,685,915 A 8/1987 Hasse et al.
4,704,116 A 11/1987 Enloe
4,724,114 A 2/1988 McFarland et al.
4,729,371 A 3/1988 Krueger et al.
4,755,178 A 7/1988 Insley et al.
4,764,325 A 8/1988 Angstadt
4,767,825 A 8/1988 Pazos et al.
4,775,579 A 10/1988 Hagy et al.
4,795,668 A 1/1989 Krueger et al.
4,803,117 A 2/1989 Daponte
4,806,408 A 2/1989 Pierre et al.
4,834,738 A 5/1989 Kielpikowski et al.
4,848,464 A 7/1989 Jennings, Jr. et al.
4,865,596 A 9/1989 Weisman et al.
4,879,170 A 11/1989 Radwanski et al.
4,891,258 A 1/1990 Fahrenkrug
4,904,440 A 2/1990 Angstadt
4,923,914 A 5/1990 Nohr et al.
4,939,016 A 7/1990 Radwanski et al.
4,940,464 A 7/1990 Van Gompel et al.
4,957,795 A 9/1990 Riedel
4,996,091 A 2/1991 McIntyre
5,017,324 A 5/1991 Kaiser et al.
5,028,224 A 7/1991 Pieper et al.
5,028,225 A 7/1991 Staheli
5,057,166 A 10/1991 Young, Sr. et al.
5,064,689 A 11/1991 Young, Sr. et al.
5,064,802 A 11/1991 Stevens et al.
5,108,820 A 4/1992 Kaneko et al.
5,114,781 A 5/1992 Morman
5,116,662 A 5/1992 Morman
5,143,680 A 9/1992 Molnar et al.
5,149,335 A 9/1992 Kellenberger et al.
5,156,902 A 10/1992 Pieper et al.
5,169,706 A 12/1992 Collier, IV et al.
5,171,391 A 12/1992 Chmielewski et al.
5,188,624 A 2/1993 Young, Sr. et al.
5,189,192 A 2/1993 LaPointe et al.
5,204,429 A 4/1993 Kaminsky et al.
5,213,817 A 5/1993 Pelley
5,213,881 A 5/1993 Timmons et al.
5,225,014 A 7/1993 Ogata et al.
5,230,959 A 7/1993 Young, Sr. et al.
5,248,524 A 9/1993 Soderlund
5,260,126 A 11/1993 Collier, IV et al.
5,272,236 A 12/1993 Lai et al.
5,278,272 A 1/1994 Lai et al.
5,279,854 A 1/1994 Kendall et al.
5,281,207 A 1/1994 Chmielewski et al.
5,284,703 A 2/1994 Everhart et al.
5,288,791 A 2/1994 Collier, IV et al.
5,290,626 A 3/1994 Nishioi et al.
5,308,906 A 5/1994 Taylor et al.
5,332,613 A 7/1994 Taylor et al.
5,336,552 A 8/1994 Strack et al.
5,349,100 A 9/1994 Mintz
5,350,597 A 9/1994 Pelley
5,350,624 A 9/1994 Georger et al.
5,352,749 A 10/1994 DeChellis et al.
5,366,793 A 11/1994 Fitts, Jr. et al.
5,372,885 A 12/1994 Tabor et al.
5,374,696 A 12/1994 Rosen et al.
5,376,198 A 12/1994 Fahrenkrug et al.
5,382,400 A 1/1995 Pike et al.
5,385,775 A 1/1995 Wright
5,387,208 A 2/1995 Ashton et al.
5,389,202 A 2/1995 Everhart et al.
5,411,497 A 5/1995 Tanzer et al.
5,415,716 A 5/1995 Kendall
5,421,940 A 6/1995 Comnils et al.
5,424,115 A 6/1995 Stokes
5,425,725 A 6/1995 Tanzer et al.
5,429,788 A 7/1995 Ribble et al.
5,432,000 A 7/1995 Young, Sr. et al.
5,433,715 A 7/1995 Tanzer et al.
5,447,677 A 9/1995 Griffoul et al.
5,486,166 A 1/1996 Bishop et al.
5,490,846 A 2/1996 Ellis et al.
5,494,622 A 2/1996 Heath et al.
5,503,908 A 4/1996 Faass
5,508,102 A 4/1996 Georger et al.
5,509,915 A 4/1996 Hanson et al.
5,511,960 A 4/1996 Terakawa et al.
5,514,324 A 5/1996 Bachar
5,516,569 A 5/1996 Veith et al.
5,516,585 A 5/1996 Young, Sr. et al.
5,518,801 A 5/1996 Chappell et al.
5,560,878 A 10/1996 Dragoo et al.
5,562,645 A 10/1996 Tanzer et al.
5,567,472 A 10/1996 Siegfried et al.
5,593,399 A 1/1997 Tanzer et al.
5,601,542 A 2/1997 Melius et al.
5,614,283 A 3/1997 Potnis et al.
5,645,542 A 7/1997 Anjur et al.
5,670,044 A 9/1997 Ogata et al.

(56) References Cited

U.S. PATENT DOCUMENTS 5,676,660 A 10/1997 Mukaida et al.
5,679,042 A 10/1997 Varona
5,681,305 A 10/1997 Korpman
5,683,752 A 11/1997 Popp et al.
5,691,035 A 11/1997 Chappell et al.
5,713,881 A 2/1998 Rezai et al.
5,718,913 A 2/1998 Dhuique-Mayer et al.
5,720,832 A 2/1998 Minto et al.
5,750,066 A 5/1998 Vonderhaar et al.
5,759,926 A 6/1998 Pike et al.
5,763,331 A 6/1998 Demhartner
5,766,388 A 6/1998 Pelley et al.
5,766,389 A 6/1998 Brandon et al.
5,789,065 A 8/1998 Haffner et al.
5,820,973 A 10/1998 Dodge, II et al.
5,824,004 A 10/1998 Osborn, III et al.
5,833,678 A 11/1998 Ashton et al.
5,849,000 A 12/1998 Anjur et al.
5,853,881 A 12/1998 Estey et al.
5,858,292 A 1/1999 Dragoo et al.
5,858,515 A 1/1999 Stokes et al.
5,879,751 A 3/1999 Bogdanski
5,882,769 A 3/1999 McCormack et al.
5,883,028 A 3/1999 Morman et al.
5,891,120 A 4/1999 Chmielewski
5,900,109 A 5/1999 Sanders et al.
5,904,675 A 5/1999 Laux et al.
5,922,163 A 7/1999 Helynranta et al.
5,938,650 A 8/1999 Baer et al.
5,964,743 A 10/1999 Abuto et al.
5,977,014 A 11/1999 Plischke et al.
5,981,410 A 11/1999 Hansen et al.
5,981,689 A 11/1999 Mitchell et al.
5,983,457 A 11/1999 Toney et al.
5,994,440 A 11/1999 Staples et al.
5,998,493 A 12/1999 Mitchell et al.
6,046,377 A 4/2000 Huntoon et al.
6,060,115 A 5/2000 Borowski et al.
6,068,620 A 5/2000 Chmielewski
6,072,101 A 6/2000 Beihoffer et al.
6,080,909 A 6/2000 Osterdahl et al.
6,087,448 A 7/2000 Mitchell et al.
6,090,875 A 7/2000 Staples et al.
6,093,474 A 7/2000 Sironi
6,121,409 A 9/2000 Mitchell et al.
6,129,720 A 10/2000 Blenke et al.
6,159,591 A 12/2000 Beihoffer et al.
6,162,959 A 12/2000 Lawrence
6,194,631 B1 2/2001 Mitchell et al.
6,221,062 B1 4/2001 Osborn, III
6,222,091 B1 4/2001 Beihoffer et al.
6,231,557 B1 5/2001 Krautkramer et al.
6,235,965 B1 5/2001 Beihoffer et al.
6,241,713 B1 6/2001 Gross et al.
6,261,679 B1 7/2001 Chen et al.
6,290,686 B1 9/2001 Tanzer
6,319,342 B1 11/2001 Riddell
6,330,735 B1 12/2001 Hahn et al.
6,342,298 B1 1/2002 Evans et al.
6,353,148 B1 3/2002 Gross
6,362,389 B1 3/2002 McDowall et al.
6,376,072 B2 4/2002 Evans et al.
6,387,495 B1 5/2002 Reeves et al.
6,392,116 B1 5/2002 Beihoffer et al.
6,403,857 B1 6/2002 Gross et al.
6,429,350 B1 8/2002 Tanzer et al.
6,455,114 B1 9/2002 Goldhirsch et al.
6,455,753 B1 9/2002 Glaug et al.
6,459,016 B1 10/2002 Rosenfeld et al.
6,470,943 B1 10/2002 Borowski et al.
6,509,512 B1 1/2003 Beihoffer et al.
6,509,513 B2 1/2003 Glaug et al.
6,552,245 B1 4/2003 Roessler et al.
6,555,502 B1 4/2003 Beihoffer et al.
6,579,274 B1 6/2003 Morman et al.
6,582,413 B2 6/2003 Krautkramer et al.
6,590,138 B2 7/2003 Onishi
6,603,054 B2 8/2003 Chen et al.
6,610,900 B1 8/2003 Tanzer
6,627,564 B1 9/2003 Morman et al.
6,641,134 B1 11/2003 Dobbertin et al.
6,641,695 B2 11/2003 Baker
6,645,190 B1 11/2003 Olson et al.
6,646,180 B1 11/2003 Chmielewski
6,664,439 B1 12/2003 Arndt et al.
6,680,423 B1 1/2004 Tanzer
6,703,846 B2 3/2004 Delzer et al.
6,706,129 B2 3/2004 Ando et al.
6,730,387 B2 5/2004 Rezai et al.
6,932,929 B2 8/2005 Krautkramer et al.
6,972,011 B2 12/2005 Maeda et al.
7,121,818 B2 10/2006 Driskell
7,247,215 B2 7/2007 Schewe et al.
7,361,694 B2 4/2008 Strandburg et al.
7,527,823 B2 5/2009 Tombült-Meyer et al.
7,717,150 B2 5/2010 Manabe et al.
7,872,168 B2 1/2011 Sawyer et al.
7,906,065 B1 3/2011 Brown et al.
7,938,813 B2 5/2011 Wang et al.
8,148,598 B2 4/2012 Tsang et al.
8,324,446 B2 12/2012 Wang et al.
8,485,347 B2 7/2013 Jackels
8,552,251 B2 10/2013 Zhou et al.
8,852,161 B2 10/2014 Hermansson
8,852,381 B2 10/2014 Nhan et al.
8,855,979 B2 10/2014 Blessing et al.
8,960,122 B2 2/2015 Yano et al.
8,986,474 B2 3/2015 Kufner et al.
9,033,018 B2 5/2015 Ogasawara et al.
9,044,359 B2 6/2015 Wciorka et al.
9,421,134 B2 8/2016 Schlinz et al.
9,549,858 B2 1/2017 Yang
10,918,529 B2 2/2021 Venturino et al.
2001/0001312 A1 5/2001 Mitchell et al.
2001/0007064 A1 7/2001 Mitchell et al.
2001/0029358 A1 10/2001 Beihoffer et al.
2001/0044612 A1 11/2001 Beihoffer et al.
2002/0007166 A1 1/2002 Mitchell et al.
2002/0015846 A1 2/2002 Evans et al.
2002/0095127 A1 7/2002 Fish et al.
2002/0115744 A1 8/2002 Svenningsen et al.
2002/0150761 A1 10/2002 Lange et al.
2002/0169430 A1 11/2002 Kirk et al.
2002/0183703 A1 12/2002 Singh et al.
2003/0014027 A1 1/2003 Beihoffer et al.
2003/0044562 A1 3/2003 Li et al.
2003/0060112 A1 3/2003 Rezai et al.
2003/0105441 A1 6/2003 Chmielewski
2003/0111774 A1 6/2003 Kellenberger et al.
2003/0114071 A1 6/2003 Everhart et al.
2003/0116888 A1 6/2003 Rymer et al.
2003/0129915 A1 7/2003 Harriz
2003/0130638 A1 7/2003 Baker
2003/0134102 A1 7/2003 Wang et al.
2003/0134559 A1 7/2003 Delzer et al.
2003/0158531 A1 8/2003 Chmielewski
2003/0212376 A1 11/2003 Walter et al.
2003/0236510 A1 12/2003 Yasumura et al.
2004/0054341 A1 3/2004 Kellenberger et al.
2004/0116014 A1 6/2004 Soerens et al.
2004/0116287 A1 6/2004 Wang et al.
2004/0222568 A1 11/2004 Armantrout et al.
2005/0031850 A1 2/2005 Mitchell et al.
2005/0096435 A1 5/2005 Smith et al.
2005/0096623 A1 5/2005 Nhan et al.
2005/0137085 A1 6/2005 Zhang et al.
2005/0148972 A1 7/2005 Miyama et al.
2005/0186351 A1 8/2005 Fung et al.
2005/0228350 A1 10/2005 Ranganathan et al.
2006/0004336 A1 1/2006 Zhang et al.
2006/0005919 A1 1/2006 Schewe et al.
2006/0141891 A1 6/2006 Melius et al.
2007/0077841 A1 4/2007 Zoch et al.
2007/0197987 A1 8/2007 Tsang et al.

(56) References Cited

U.S. PATENT DOCUMENTS

| | | | |
|---|---|---|---|
| 2007/0255243 | A1 | 11/2007 | Kaun et al. |
| 2008/0132863 | A1 | 6/2008 | Waksmundzki et al. |
| 2008/0312628 | A1 | 12/2008 | Hundorf et al. |
| 2009/0018517 | A1 | 1/2009 | Cecconi et al. |
| 2009/0076472 | A1 | 3/2009 | Goldwasser et al. |
| 2009/0198205 | A1 | 8/2009 | Malowaniec et al. |
| 2009/0258138 | A1 | 10/2009 | Burmester et al. |
| 2010/0030177 | A1 | 2/2010 | Sanada et al. |
| 2010/0051166 | A1 | 3/2010 | Hundorf et al. |
| 2010/0228209 | A1 | 9/2010 | Carlucci et al. |
| 2010/0312208 | A1 | 12/2010 | Bond et al. |
| 2011/0041999 | A1 | 2/2011 | Hundorf et al. |
| 2011/0152809 | A1 | 6/2011 | Carlucci et al. |
| 2012/0024470 | A1 | 2/2012 | Hundorf et al. |
| 2012/0148821 | A1 | 6/2012 | Ducker et al. |
| 2012/0316523 | A1 | 12/2012 | Hippe et al. |
| 2012/0316524 | A1 | 12/2012 | Thomann et al. |
| 2012/0316528 | A1 | 12/2012 | Kreuzer et al. |
| 2013/0072889 | A1 | 3/2013 | Yang |
| 2013/0112348 | A1 | 5/2013 | Blessing et al. |
| 2013/0165882 | A1 | 6/2013 | Kawakami et al. |
| 2013/0174959 | A1 | 7/2013 | Kufner et al. |
| 2013/0226119 | A1 | 8/2013 | Katsuragawa et al. |
| 2013/0240139 | A1 | 9/2013 | Zhou et al. |
| 2013/0331806 | A1 | 12/2013 | Rosati et al. |
| 2014/0005622 | A1 | 1/2014 | Wirtz et al. |
| 2014/0005623 | A1 | 1/2014 | Wirtz et al. |
| 2014/0005625 | A1 | 1/2014 | Wirtz et al. |
| 2014/0027943 | A1 | 1/2014 | Hoshika |
| 2014/0163503 | A1 | 6/2014 | Arizti et al. |
| 2014/0163504 | A1 | 6/2014 | Bianchi et al. |
| 2014/0261987 | A1 | 9/2014 | Chartrel |
| 2014/0276509 | A1 | 9/2014 | Ducker et al. |
| 2014/0303582 | A1 | 10/2014 | Wright et al. |
| 2014/0308483 | A1 | 10/2014 | Li |
| 2014/0324008 | A1 | 10/2014 | Hundorf et al. |
| 2014/0329672 | A1 | 11/2014 | Colclough, Jr. et al. |
| 2015/0005727 | A1 | 1/2015 | Matsushita et al. |
| 2015/0011960 | A1 | 1/2015 | Arayama et al. |
| 2015/0065974 | A1 | 3/2015 | Michiels et al. |
| 2015/0080821 | A1 | 3/2015 | Peri et al. |
| 2015/0094682 | A1 | 4/2015 | Fell et al. |
| 2015/0164710 | A1 | 6/2015 | Ehkme et al. |
| 2015/0245952 | A1 | 9/2015 | Gahan |
| 2015/0245958 | A1 | 9/2015 | Chmielewski et al. |
| 2015/0320617 | A1 | 11/2015 | Ducker |
| 2015/0359683 | A1 | 12/2015 | Jackels et al. |
| 2017/0095380 | A1 | 4/2017 | Wirtz et al. |
| 2017/0156947 | A1 | 6/2017 | Esquerra et al. |
| 2017/0258955 | A1 | 9/2017 | Lindner et al. |
| 2017/0312146 | A1 | 11/2017 | Bianchi et al. |
| 2018/0078670 | A1 | 3/2018 | Stelzig et al. |
| 2019/0099302 | A1 | 4/2019 | Venturino et al. |
| 2019/0159946 | A1 | 5/2019 | Descheemaecker et al. |
| 2020/0030162 | A1 | 1/2020 | Lindner et al. |
| 2020/0289355 | A1 | 9/2020 | Robran |
| 2021/0085530 | A1 | 3/2021 | Venturino et al. |

FOREIGN PATENT DOCUMENTS

| | | | |
|---|---|---|---|
| CN | 1406566 | A | 4/2003 |
| CN | 1494883 | A | 5/2004 |
| CN | 1736355 | A | 2/2006 |
| CN | 1853013 | A | 10/2006 |
| CN | 1889985 | A | 1/2007 |
| CN | 101070458 | A | 11/2007 |
| CN | 101797201 | A | 8/2010 |
| CN | 101978107 | A | 2/2011 |
| CN | 102065816 | A | 5/2011 |
| CN | 102281852 | A | 12/2011 |
| CN | 102686395 | A | 9/2012 |
| CN | 102844009 | A | 12/2012 |
| CN | 102883695 | A | 1/2013 |
| CN | 103037823 | A | 4/2013 |
| CN | 103179931 | A | 6/2013 |
| CN | 103202746 | A | 7/2013 |
| CN | 103429207 | A | 12/2013 |
| CN | 103429278 | A | 12/2013 |
| CN | 104066407 | A | 9/2014 |
| CN | 204016630 | U | 12/2014 |
| CN | 104394823 | A | 3/2015 |
| CN | 104507438 | A | 4/2015 |
| CN | 105979917 | A | 9/2016 |
| CN | 107080619 | A | 8/2017 |
| CN | 108348383 | A | 7/2018 |
| CN | 108778204 | A | 11/2018 |
| CN | 108779594 | A | 11/2018 |
| DE | 202012102100 | U1 | 10/2012 |
| EP | 0179937 | B1 | 4/1990 |
| EP | 0497072 | A1 | 8/1992 |
| EP | 0534863 | A1 | 3/1993 |
| EP | 0601610 | A1 | 6/1994 |
| EP | 0611607 | A1 | 8/1994 |
| EP | 0463716 | B1 | 6/1999 |
| EP | 0788874 | B1 | 9/1999 |
| EP | 0633009 | B1 | 10/1999 |
| EP | 0947549 | A1 | 10/1999 |
| EP | 1110528 | A2 | 6/2001 |
| EP | 0700673 | B1 | 3/2002 |
| EP | 0802949 | B1 | 5/2003 |
| EP | 1013291 | B1 | 6/2005 |
| EP | 1253231 | B1 | 11/2005 |
| EP | 1697057 | B1 | 11/2007 |
| EP | 2532330 | A1 | 12/2012 |
| EP | 2679210 | B1 | 1/2015 |
| EP | 3466387 | A1 | 4/2019 |
| JP | H0465568 | A | 3/1992 |
| JP | H07138866 | A | 5/1995 |
| JP | H07213552 | A | 8/1995 |
| JP | 1997327479 | A | 12/1997 |
| JP | H11320742 | A | 11/1999 |
| JP | 2001145659 | A | 5/2001 |
| JP | 2013252332 | A | 12/2013 |
| JP | 2013252333 | A | 12/2013 |
| JP | 2015181785 | A | 10/2015 |
| JP | 2018003205 | A | 1/2018 |
| JP | 2019084146 | A | 6/2019 |
| JP | 2019118587 | A | 7/2019 |
| RU | 2197272 | C1 | 1/2003 |
| WO | 1993015249 | A1 | 8/1993 |
| WO | 1994009043 | A1 | 4/1994 |
| WO | 1996011107 | A1 | 4/1996 |
| WO | 1996014885 | A1 | 5/1996 |
| WO | 1996016624 | A2 | 6/1996 |
| WO | 1998003710 | A1 | 1/1998 |
| WO | 1999000093 | A1 | 1/1999 |
| WO | 1999000095 | A1 | 1/1999 |
| WO | 2000032142 | A1 | 6/2000 |
| WO | 2000037000 | A1 | 6/2000 |
| WO | 2000037009 | A2 | 6/2000 |
| WO | 2000037735 | A1 | 6/2000 |
| WO | 2000059439 | A1 | 10/2000 |
| WO | 2000063295 | A1 | 10/2000 |
| WO | 2001015650 | A1 | 3/2001 |
| WO | 2002010032 | A2 | 2/2002 |
| WO | 2002024132 | A2 | 3/2002 |
| WO | 2002034184 | A1 | 5/2002 |
| WO | 2002043784 | A2 | 6/2002 |
| WO | 2002053378 | A2 | 7/2002 |
| WO | 2003018671 | A1 | 3/2003 |
| WO | 2003037392 | A1 | 5/2003 |
| WO | 2003051411 | A1 | 6/2003 |
| WO | 2003051417 | A1 | 6/2003 |
| WO | 2003052190 | A1 | 6/2003 |
| WO | 2003053319 | A2 | 7/2003 |
| WO | 2003057964 | A1 | 7/2003 |
| WO | 2007122525 | A1 | 11/2007 |
| WO | 2014145312 | A2 | 9/2014 |
| WO | 2017171785 | A1 | 10/2017 |
| WO | 2022046030 | A1 | 3/2022 |
| WO | 2022046031 | A1 | 3/2022 |

(56) References Cited

FOREIGN PATENT DOCUMENTS

| | | |
|---|---|---|
| WO | 2022046033 A1 | 3/2022 |
| WO | 2022046036 A1 | 3/2022 |

OTHER PUBLICATIONS

Baer, Samuel C., Particle Containment And Immobilization in Roll Good Materials, INJ, Fall 2004, pp. 54-59.

Coates, Geoffrey W. et al., "Oscillating Sterocontrol: A Strategy for the Synthesis of Thermoplastic Elastomeric Polypropylene", Science, vol. 267, Jan. 13, 1995, pp. 217-219.

Cowie, J.M.G., "Solubility and the Cohesive Energy Density", Polymers: Chemistry and Physics of Modern Materials, Intext Educational Publishers, New York, 1973, pp. 142-145.

Industry News—LIVE from Index 2014, Ultrasonic diaper core former Helixbond, http://shows.nonwovens-industry.com/index2014/news/40624.

Lawrence, K.D. et al., "An improved Device for the Formation of Superfine, Thermoplastic Fibers", NRL Report 5265, U.S. Navel Research Laboratory, Washington, D.C., Feb. 11, 1959.

Wiley, Molecular Weight Distributions, "Encyclopedia of Polymer Science and Engineering", Second Edition, vol. 3, John Wiley & Sons, New York, 1985, pp. 299-300.

Neumann, A.W., and R. J. Good, "Techniques of Measuring Contact Angles", Chapter 2, Surface and Colloid Science—Experimental Methods, 1979, vol. 11, edited by R.J. Good and R.R. Stomberg, pp. 31-91.

Wagener, K.B., "Oscillating Catalysts: A New Twist for Plastics", Science, vol. 267, Jan. 13, 1995, p. 191.

Wente, V.A. et al., "Manufacture of Superfine Organic Fibers", NRL Report 4364, U.S. Naval Research Laboratory, Washington, D.C., May 25, 1954, pp. 1-15.

Whitmore, Darryl L, "Non Wovens Containing Immobilized Superabsorbent Polymer Particles", Jeff Journal, Fall, 2003, https://www.jeffjournal.org/INJ/inj03_3/p35-40-whitmore.pdf.

ABSORBENT STRUCTURES AND METHODS FOR MANUFACTURING ABSORBENT STRUCTURES

TECHNICAL FIELD

The present disclosure is directed to absorbent structures and more specifically to absorbent structures with a high superabsorbent material content.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. By preventing leakage of the exudates from the absorbent article, the absorbent article intends to prevent the body exudates from soiling or contaminating a wearer's or caregiver's clothing or other articles, such as bedding, that can come in contact with the wearer.

Absorbent cores typically help with liquid uptake and storage within absorbent articles. Many absorbent cores contain multiple absorbent materials such as superabsorbent material and pulp fluff or other fibrous absorbent material. Each type of absorbent material helps to impart such absorbent cores with a range of properties useful in absorbing and retaining liquid bodily exudates. For example, pulp fluff or other fibrous absorbent material may absorb liquid more quickly than superabsorbent material, and the superabsorbent material may be able retain more liquid per particle than pulp fluff.

Many advances have been made to absorbent cores, and particularly to the superabsorbent material of absorbent cores. Some current absorbent cores may now have absorbent material comprising mostly superabsorbent material and further comprising only a small portion of other absorbent material. Other current absorbent cores comprise only superabsorbent material as the absorbent material. Further advances in absorbent cores having a high superabsorbent material content are continually desired to further improve the performance of such absorbent cores.

SUMMARY OF THE DISCLOSURE

Absorbent structures and methods of manufacturing such absorbent structures are disclosed in the present disclosure. In a first embodiment, an absorbent structure having a longitudinal axis and a lateral axis may comprise a first substrate material layer having a first surface and a second surface, a second substrate material layer having a first surface and a second surface, and a mixture of superabsorbent particles and adhesive disposed between the first substrate material layer and the second substrate material layer, wherein the superabsorbent particles are disposed in an amount greater than or equal to 400 gsm and less than or equal to 600 gsm, and wherein the adhesive is disposed in an amount greater than or equal to 4% and less than or equal to 6%, by weight, of the weight of the superabsorbent particles, wherein the adhesive forms a three-dimensional mesh network comprising network adhesive filaments with the superabsorbent particles immobilized within the mesh network, and the network adhesive filaments extending substantially throughout a three-dimensional space defined by the network adhesive filaments and the superabsorbent particles, and wherein the absorbent structure has a Gray Level % Coefficient of Variability value (GL % COV) of less than or equal to 34.5, according to the Pad Uniformity Test Method.

In a second embodiment, an absorbent structure having a longitudinal axis and a lateral axis may comprise a first substrate material layer having a first surface and a second surface, a second substrate material layer having a first surface and a second surface, and a mixture of superabsorbent particles and adhesive disposed between the first substrate material layer and the second substrate material layer, the superabsorbent particles being disposed in an amount greater than or equal to 400 gsm and less than or equal to 500 gsm, and wherein the adhesive is disposed in an amount greater than or equal to 4% and less than or equal to 6%, by weight, of the weight of the superabsorbent particles, wherein the adhesive forms a three-dimensional mesh network comprising network adhesive filaments with the superabsorbent particles immobilized within the mesh network, and the network adhesive filaments extending substantially throughout a three-dimensional space defined by the network adhesive filaments and the superabsorbent particles, and wherein the absorbent structure has a CD Gray Level Variability (CD GL Var.) values less than or equal to 510, according to the Pad Uniformity Test.

In a third embodiment, a method of manufacturing an absorbent structure may comprise: feeding a first stream of superabsorbent particles toward a first substrate material layer moving in a machine direction, the first stream of superabsorbent particles having a first side and a second side, spraying, with a first adhesive applicator having a first adhesive nozzle, the first side of the first stream of superabsorbent particles with a first adhesive, the first adhesive contacting the first stream of superabsorbent particles and intermixing with the superabsorbent particles of the first stream of superabsorbent particles prior to said superabsorbent particles depositing onto the first substrate material layer, the first adhesive contacting the first stream of superabsorbent particles at a first contact point having a first height as measured from the first substrate material layer, spraying, with a second adhesive applicator having a second adhesive nozzle, the second side of the first stream of superabsorbent particles with a second adhesive, the second adhesive contacting the first stream of superabsorbent particles and intermixing with the superabsorbent particles of the first stream of superabsorbent particles prior to said superabsorbent particles depositing onto the first substrate material layer, the second adhesive contacting the first stream of superabsorbent particles at a second contact point having a second height as measured from the first substrate material layer, depositing the intermixed superabsorbent particles of the first stream of superabsorbent particles, first adhesive, and second adhesive onto the first substrate material layer, covering the mixture of the superabsorbent particles of the first stream of superabsorbent particles, the first adhesive, and the second adhesive with a second substrate material layer, and separating the mixture of the superabsorbent particles, adhesive, the first substrate material layer, and the second substrate material layer into individual absorbent structures, wherein absorbent structures produced by this method having superabsorbent particles disposed in an amount equal to 300 gsm and adhesive disposed in an amount greater than 3% and less than 4%, by weight, of the weight of the superabsorbent particles, have CD Gray Level Variability (CD GL Var.) values less than or equal to 675, according to the Pad Uniformity Test.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
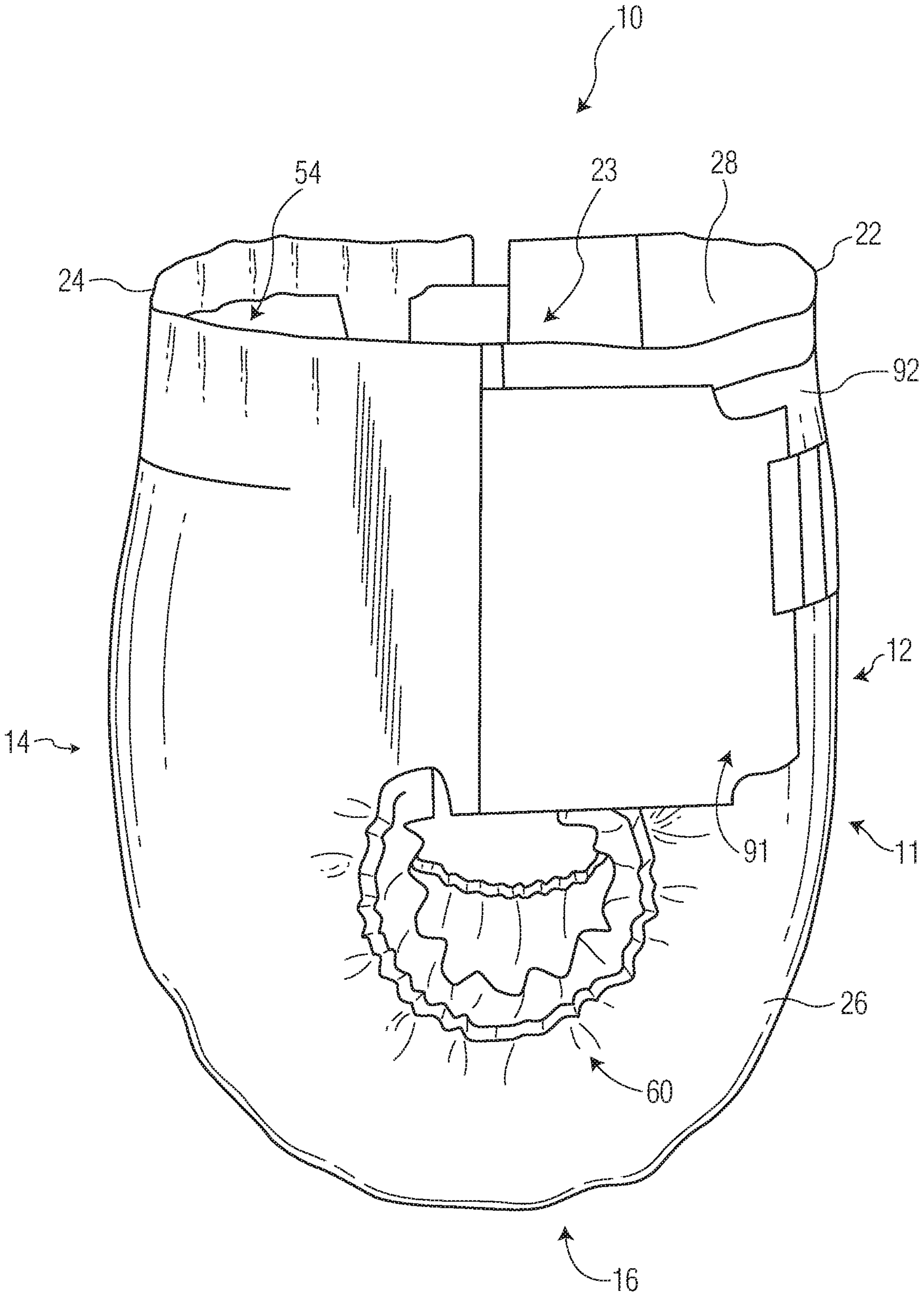
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards absorbent cores absorbent material comprising a high proportion of superabsorbent material. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles “a”, “an”, “the” and “said” are intended to mean that there are one or more of the elements. The terms “comprising”, “including” and “having” are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions

The term “absorbent article” refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products and other adult care garments, medical garments, surgical pads and bandages, other personal care or health care garments, and the like without departing from the scope of the present disclosure.

The term “acquisition layer” refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term “bonded” or “coupled” refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term “carded web” refers herein to a web containing natural or synthetic staple length fibers typically having fiber lengths less than 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

“Elastomeric” refers to a material or composite which can be elongated by at least 50 percent of its relaxed length and which will recover, upon release of the applied force, at least 20 percent of its elongation. It is generally preferred that the elastomeric material or composite be capable of being elongated by at least 50 percent, more preferably by at least 100 percent, and still more preferably by at least 300 percent of its relaxed length and recover, upon release of an applied force, at least 50 percent of its elongation.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearers body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than 0.3, and in an embodiment, between 0.6, 5 and 10 and 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least 15 times its weight and, in an embodiment, at least 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "super-majority" refers herein to a majority of at least 65%.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Absorbent Article

Figure 2:
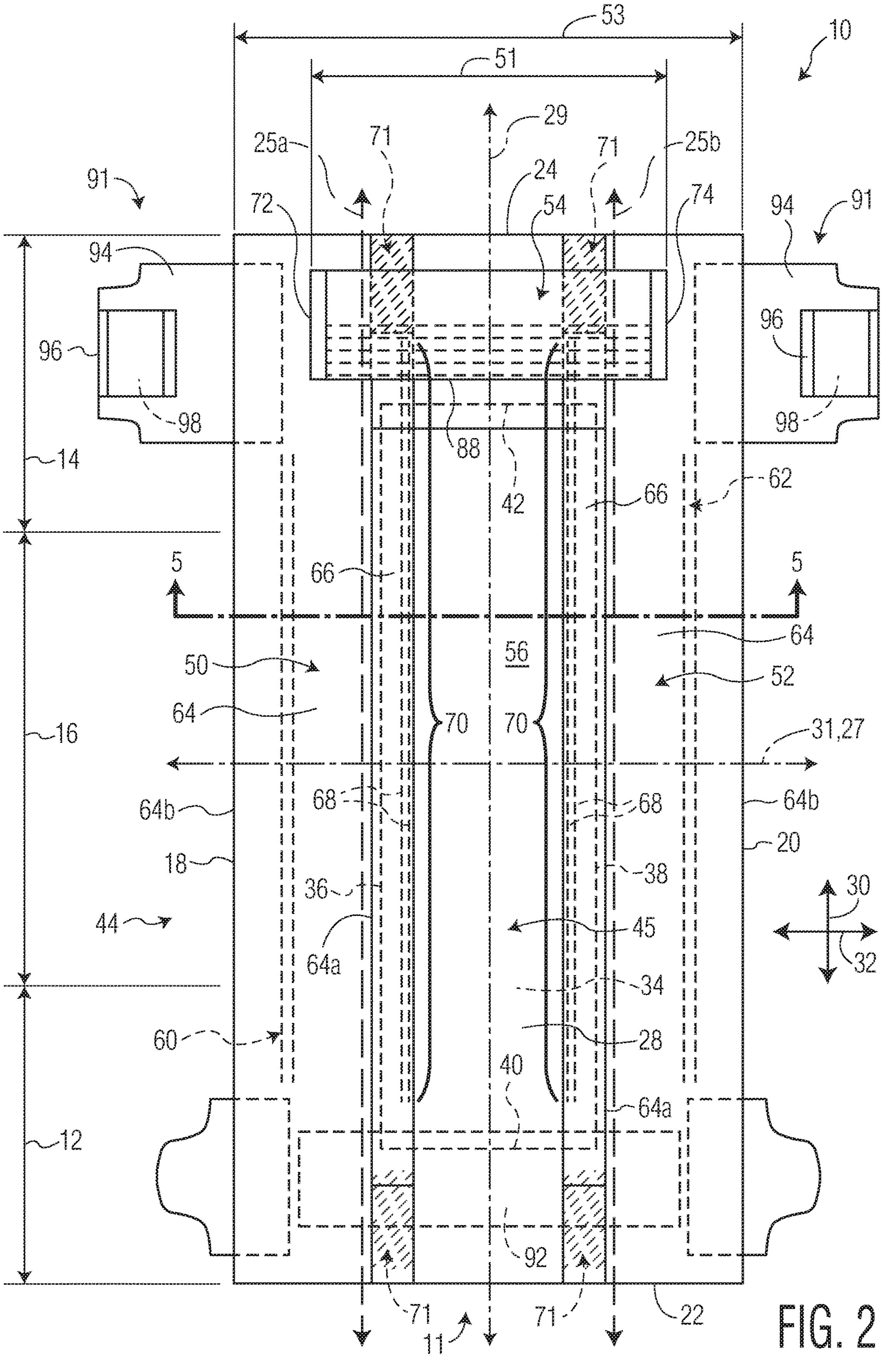
FIG. 2 is a top plan view of the absorbent article of FIG. 1 in a stretched, laid flat, unfastened condition.

Referring to FIGS. 1-2, a non-limiting illustration of an absorbent article 10, for example a diaper, is illustrated. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross-machine direction manufacturing of a product, without departing from the spirit and scope of the disclosure. For example, the absorbent article 210 in FIGS. 3-4 provide an exemplary embodiment of an absorbent article 210 that can be manufactured in cross-machine direction manufacturing process.

Figure 3:
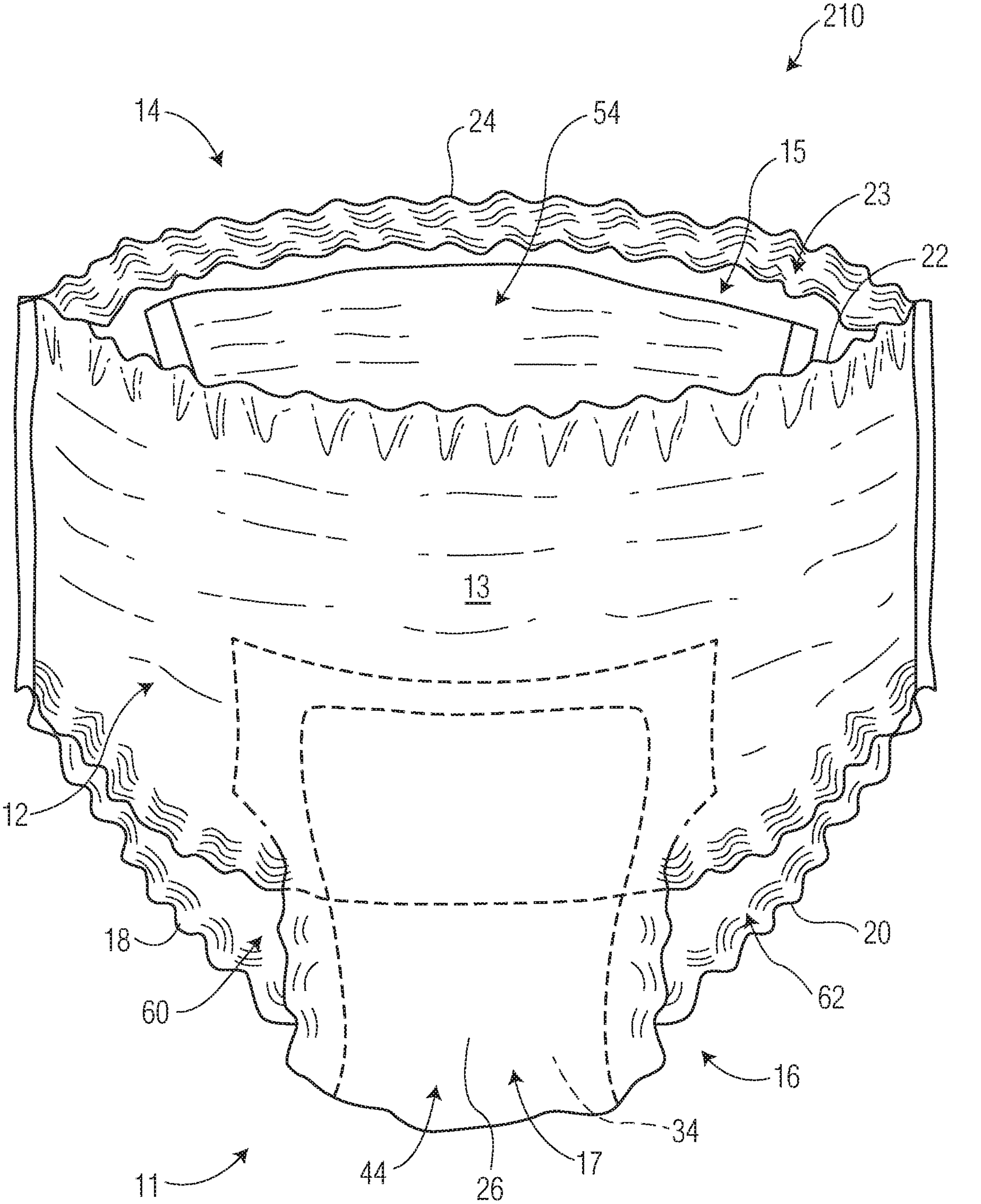
FIG. 3 is a front perspective view of an alternative embodiment of an absorbent article, such as a pant.
Figure 4:
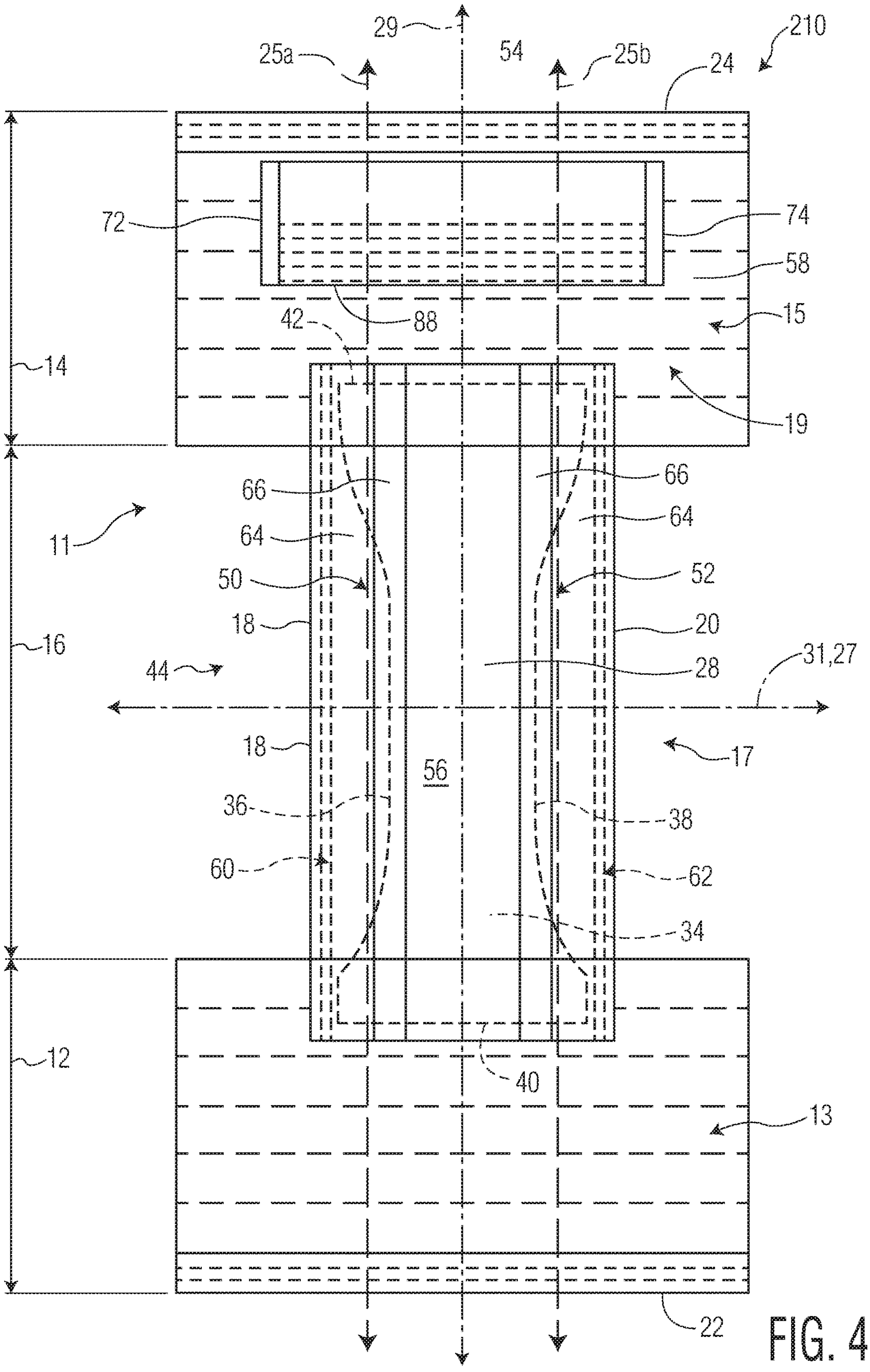
FIG. 4 is a top plan view of the absorbent article of FIG. 3 in a stretched, laid flat condition.

The absorbent article 10 illustrated in FIGS. 1 and 2 and the absorbent article 210 illustrated in FIGS. 3 and 4 can each include a chassis 11. The absorbent article 10, 210 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front-end region, the rear waist region 14 can be referred to as the rear-end region, and the crotch region 16 can be referred to as the intermediate region. In the embodiment depicted in FIGS. 3 and 4, a three-piece construction of an absorbent article 210 is depicted where the absorbent article 210 can have a chassis 11 including a front waist panel 13 defining the front waist region 12, a rear waist panel 15 defining the rear waist region 14, and an absorbent panel 17 defining the crotch region 16 of the absorbent article 210. The absorbent panel 17 can extend between the front waist panel 13 and the rear waist panel 15. In some embodiments, the absorbent panel 17 can overlap the front waist panel 13 and the rear waist panel 15. The absorbent panel 17 can be bonded to the front waist panel 13 and the rear waist panel 15 to define a three-piece construction. However, it is contemplated that an absorbent article can be manufactured in a cross-machine direction without being a three-piece construction garment.

The absorbent article 10, 210 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent article 10 illustrated in FIGS. 1 and 2. In other embodiments, the longitudinal side edges 18, 20 can be curved between the front waist edge 22 and the rear waist edge 24. In the absorbent article 210 of FIGS. 3 and 4, the longitudinal side edges 18, 20 can include portions of the front waist panel 13, the absorbent panel 17, and the rear waist panel 15.

The front waist region 12 can include the portion of the absorbent article 10, 210 that, when worn, is positioned at least in part on the front of the wearer while the rear waist region 14 can include the portion of the absorbent article 10, 210 that, when worn, is positioned at least in part on the back of the wearer. The crotch region 16 of the absorbent article 10, 210 can include the portion of the absorbent article 10, 210 that, when worn, is positioned between the legs of the wearer and can partially cover the lower torso of the wearer. The waist edges, 22 and 24, of the absorbent article 10, 210 are configured to encircle the waist of the wearer and together define a central waist opening 23 (as labeled in FIG. 1 and FIG. 3) for the waist of the wearer. Portions of the longitudinal side edges 18, 20 in the crotch region 16 can generally define leg openings for the legs of the wearer when the absorbent article 10, 210 is worn.

The absorbent article 10, 210 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIGS. 2 and 4, the absorbent article 10, 210 can have a longitudinal axis 29 extending in the longitudinal direction 30 and a lateral axis 31 extending in the lateral direction 32.

Figure 5:
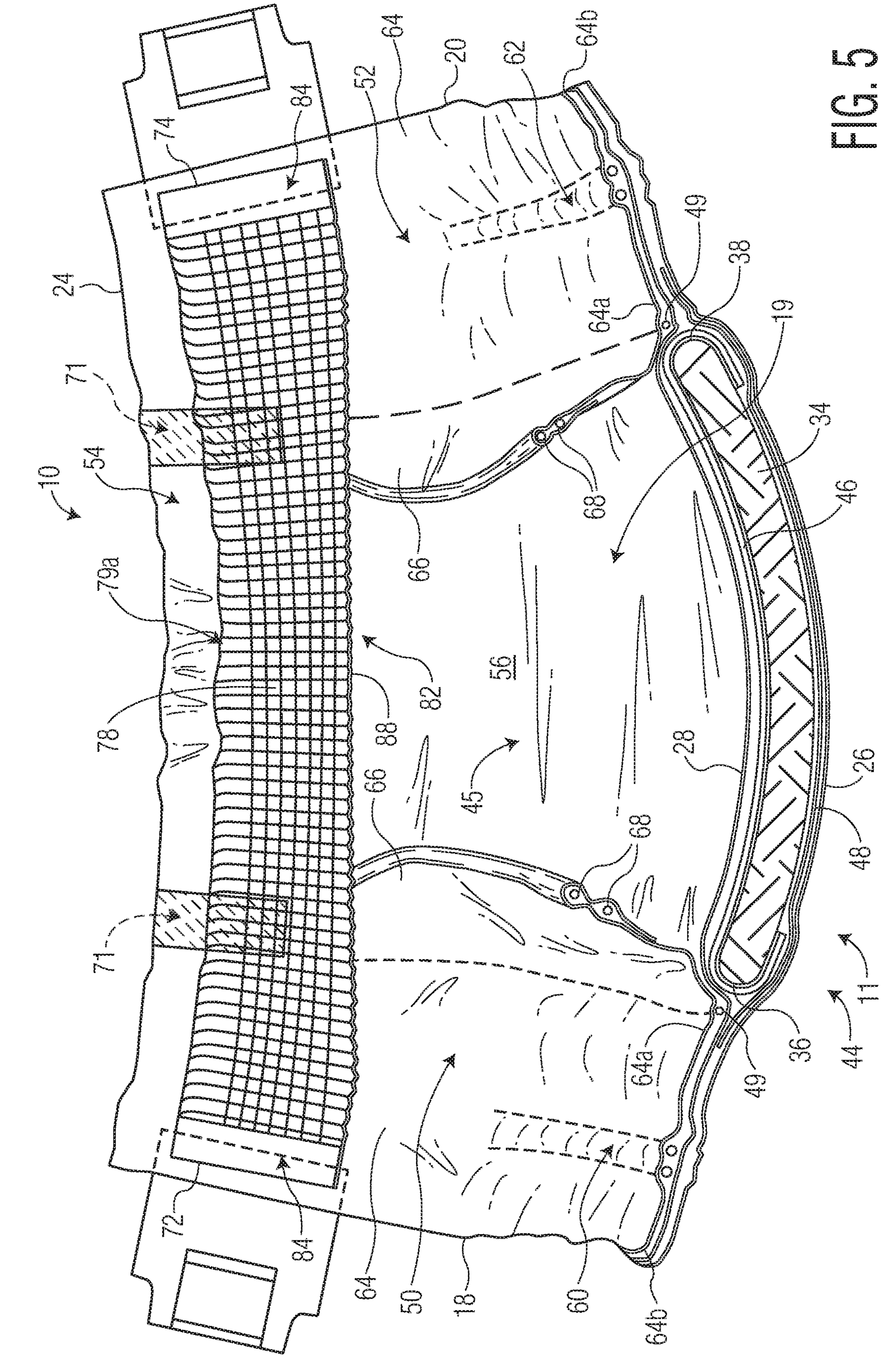
FIG. 5 is a front perspective cross-sectional view taken along line 5-5 from FIG. 2, with the absorbent article being in a relaxed configuration.

The chassis 11 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10, 210. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10, 210. The bodyside liner 28, the outer cover 26, and the absorbent body 34 can form part of an absorbent assembly 44. In the absorbent article 210 of FIGS. 3 and 4, the absorbent panel 17 can form the absorbent assembly 44. The absorbent assembly 44 can also include a fluid transfer layer 46 (as shown in FIG. 5) and a fluid acquisition layer (not shown) between the bodyside liner 28 and the fluid transfer layer 46 as is known in the art. The absorbent assembly 44 can also include a spacer layer 48 (as shown in FIG. 5) disposed between the absorbent body 34 and the outer cover 26.

The absorbent article 10, 210 can be configured to contain and/or absorb liquid, solid, and semi-solid body exudates discharged from the wearer. In some embodiments, containment flaps 50, 52 can be configured to provide a barrier to the lateral flow of body exudates. To further enhance containment and/or absorption of body exudates, the absorbent article 10, 210 can suitably include a waist containment member 54. In some embodiments, the waist containment member 54 can be disposed in the rear waist region 14 of the absorbent article 10, 210. Although not depicted herein, it is contemplated that the waist containment member 54 can be additionally or alternatively disposed in the front waist region 12 of the absorbent article 10, 210.

The waist containment member 54 can be disposed on the body facing surface 19 of the chassis 11 to help contain and/or absorb body exudates. In some embodiments, such as in the absorbent articles 10 depicted in FIGS. 1 and 2, the waist containment member 54 can be disposed on the body facing surface 45 of the absorbent assembly 44. In some embodiments, the waist containment member 54 can be disposed on the body facing surface 56 of the bodyside liner 28. In some embodiments, such as in the absorbent article 210 depicted in FIGS. 3 and 4, the waist containment member 54 can be disposed on the body facing surface 58 of the rear waist panel 15.

The absorbent article 10, 210 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10, 210. The leg elastic members 60, 62 can be parallel to the longitudinal axis 29 as shown in FIGS. 2 and 4 or can be curved as is known in the art. The leg elastic members 60, 62 can be elastomeric and can provide elasticized leg cuffs.

In some embodiments, the absorbent article 10, 210 can further include longitudinal extending fold lines 25*a*, 25*b*, as shown in FIGS. 2 and 4. The first longitudinal extending fold line 25*a* can be on one side of the longitudinal axis 29 of the absorbent article 10, 210 and the second longitudinal extending fold line 25*b* can be on an opposite side of the longitudinal axis 29. In some embodiments, the longitudinal extending fold lines 25*a*, 25*b* can be generally parallel to the longitudinal axis 29 of the absorbent article 10, 210. In some embodiments, the absorbent article 10, 210 can further include a lateral extending fold line 27. The lateral extending fold line 27 can be parallel to and located at the lateral axis 31 of the absorbent article 10, 210 in some embodiments.

Additional details regarding each of these elements of the absorbent article 10, 210 described herein can be found below and with reference to the Figures.

Outer Cover

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10, 210. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two-layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A.G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10, 210 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Bodyside Liner:

The bodyside liner 28 of the absorbent article 10, 110, 210 can overlay the absorbent body 34 and the outer cover 26 and can isolate the wearer's skin from liquid waste retained by the absorbent body 34. In various embodiments, a fluid transfer layer 46 can be positioned between the bodyside liner 28 and the absorbent body 34. In various embodiments, an acquisition layer (not shown) can be positioned between the bodyside liner 28 and the absorbent body 34 or a fluid transfer layer 46, if present. In various embodiments, the bodyside liner 28 can be bonded to the acquisition layer, or to the fluid transfer layer 46 if no acquisition layer is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer, if present, and/or a spacer layer 48, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. The bodyside liner 28 may be narrower than the outer cover 26. However, in other embodiments, the bodyside liner 28 and the outer cover 26 may be of the same dimensions in width and length. In other embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material. The bodyside liner 28 can be of different shapes, including rectangular, hourglass, or any other shape. The bodyside liner 28 can be suitably compliant, soft feeling, and non-irritating to the wearers skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,474,660 to Kirby, Scott S. C. et al.

For example, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 28 or it can be selectively applied to particular sections of the bodyside liner 28.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from 10 or 12 to 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10, 210. In other aspects, the bodyside liner 28 can be stretchable, and more suitably elastic, in both the lateral and the longitudinal directions 32, 30, respectively.

Containment Flaps

In an embodiment, the absorbent article 10, 210 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10, 210 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10, through the crotch region 16 to the rear waist region 14 of the absorbent article 10. In some embodiments, the containment flaps 50, 52 can extend in a direction substantially parallel to the longitudinal axis 29 of the absorbent article 10, 210, however, in other embodiments, the containment flaps 50, 52 can be curved, as is known in the art. In other embodiments, such as the absorbent article 210 in FIGS. 3 and 4, the containment flaps 50, 52 can be disposed on the absorbent panel 17 in the crotch region 16.

In embodiments where the containment flaps 50, 52 are coupled to the chassis 11, the containment flaps 50, 52 can be bonded to the bodyside liner 28 with a barrier adhesive 49, as shown in FIG. 5. Alternatively, the containment flaps 50, 52 can be bonded to the outer cover 26 with a barrier adhesive 49, or to the spacer layer 48. Of course, the containment flaps 50, 52 can be bonded to other components of the chassis 11 and can be bonded with other suitable means other than a barrier adhesive 49. The containment flaps 50, 52 can be constructed of a fibrous material which can be similar to the material forming the bodyside liner 28. Other conventional materials, such as polymer films, can also be employed.

The containment flaps 50, 52 can each include a base portion 64 and a projection portion 66. The base portion 64 can be bonded to the chassis 11, for example, to the bodyside liner 28 or the outer cover 26 as mentioned above. The base portion 64 can include a proximal end 64*a* and a distal end 64*b*. The projection portion 66 can be separated from the base portion 64 at the proximal end 64*a* of the base portion 64. As used in this context, the projection portion 66 is separated from the base portion 64 at the proximal end 64*a* of the base portion 64 in that the proximal end 64*a* of the base portion 64 defines a transition between the projection portion 66 and the base portion 64. The proximal end 64*a* of the base portion 64 can be located near the barrier adhesive 49. In some embodiments, the distal ends 64*b* of the base portion 64 can laterally extend to the respective longitudinal side edges 18, 20 of the absorbent article 10, 210. In other embodiments, the distal ends 64*b* of the base portion 64 can end laterally inward of the respective longitudinal side edges 18, 20 of the absorbent article 10, 210. The containment flaps 50, 52 can also each include a projection portion 66 that is configured to extend away from the body facing surface 19 of the chassis 11 at least in the crotch region 16 when the absorbent article 10, 210 is in a relaxed configuration, as illustrated in FIG. 5. The containment flaps 50, 52 can include a tack-down region 71 in either or both of the front waist region 12 and the rear waist region 14 where the projection portion 66 is coupled to the body facing surface 19 of the chassis 11.

It is contemplated that the containment flaps 50, 52 can be of various configurations and shapes, and can be constructed by various methods. For example, the containment flaps 50, 52 of FIG. 5 depict a vertical containment flap 50, 52 with a tack-down region 71 in both the front and rear waist regions 12, 14 where the projection portion 66 of each containment flap 50, 52 is tacked down to the bodyside liner 28 towards or away from the longitudinal axis 29 of the absorbent article 10, 210. However, the containment flaps 50, 52 can include a tack-down region 71 where the projection portion 66 of each of the containment flaps 50, 52 is folded back upon itself and coupled to itself and the bodyside liner 28 in a "C-shape" configuration, as is known in the art and described in U.S. Pat. No. 5,895,382 to Robert L. Popp et al. As yet another alternative, it is contemplated that the containment flaps 50, 52 could be constructed in a "T-shape" configuration, such as described in U.S. Pat. No. 9,259,362 by Robert L. Popp et al. Such a configuration can also include a tack-down region 71 in either or both of the front and rear waist regions 12, 14, respectively. Of course, other configurations of containment flaps 50, 52 can be used in the absorbent article 10, 210 and still remain within the scope of this disclosure.

The containment flaps 50, 52 can include one or more flap elastic members 68, such as the two flap elastic strands depicted in FIG. 5. Suitable elastomeric materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastomeric properties itself.

The flap elastic members 68, as illustrated in FIG. 5, can have two strands of elastomeric material extending longitudinally in the projection portion 66 of the containment flaps 50, 52, in generally parallel, spaced relation with each other. The elastic members 68 can be within the containment flaps 50, 52 while in an elastically contractible condition such that contraction of the strands gathers and shortens the projection portions 66 of the containment flaps 50, 52 in the longitudinal direction 30. As a result, the elastic members 68 can bias the projection portions 66 of the containment flaps 50, 52 to extend away from the body facing surface 45 of the absorbent assembly 44 in a generally upright orientation of the containment flaps 50, 52, especially in the crotch region 16 of the absorbent article 10, 210, when the absorbent article 10 is in a relaxed configuration.

During manufacture of the containment flaps 50, 52 at least a portion of the elastic members 68 can be bonded to the containment flaps 50, 52 while the elastic members 68 are elongated. The percent elongation of the elastic members 68 can be, for example, 110% to 350%. In one embodiment, the elastic members 68 can be coated with adhesive while elongated to a specified length prior to attaching to the elastic members 68 to the containment flaps 50, 52. In a stretched condition, the length of the elastic members 68 which have adhesive coupled thereto can provide an active flap elastic region 70 in the containment flaps 50, 52, as labeled in FIG. 2, which will gather upon relaxation of the absorbent article 10. The active flap elastic region 70 of containment flaps 50, 52 can be of a longitudinal length that is less than the length of the absorbent article 10, 210. In this exemplary method of bonding the elastic members 68 to the containment flaps 50, 52, the portion of the elastic members 68 not coated with adhesive, will retract after the elastic members 68 and the absorbent article 10 are cut in manufacturing to form an individual absorbent article 10. As noted above, the relaxing of the elastic members 68 in the active flap elastic region 70 when the absorbent article 10, 210 is in a relaxed condition can cause each containment flap 50, 52 to gather and cause the projection portion 66 of each containment flap 50, 52 to extend away from the body facing surface 19 of the chassis 11 (e.g., the body facing surface 45 of the absorbent assembly 44 or the body facing surface 56 of the bodyside liner 28), as depicted in FIG. 5.

Of course, the elastic members 68 can be bonded to the containment flaps 50, 52 in various other ways as known by those of skill in the art to provide an active flap elastic region 70, which is within the scope of this disclosure. Additionally, the active flap elastic regions 70 can be shorter or longer than depicted herein, including extending to the front waist edge 22 and the rear waist edge 24, and still be within the scope of this disclosure.

Leg Elastics

Leg elastic members 60, 62 can be secured to the outer cover 26, such as by being bonded thereto by laminate adhesive, generally laterally inward of the longitudinal side edges, 18 and 20, of the absorbent article 10, 210. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the base portion 64 of each containment flap 50, 52 and the bodyside liner 28 as depicted in FIG. 5, between the base portion 64 of each containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein each include two elastic strands. A wide variety of elastomeric materials may be used for the leg elastic members 60, 62.

Suitable elastomeric materials can include sheets, strands or ribbons of natural rubber, synthetic rubber, or thermoplastic elastomeric materials. The elastomeric materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10, 210 without departing from the scope of this disclosure.

Waist Containment Member

In an embodiment, the absorbent article 10, 210 can have one or more waist containment members 54. The waist containment member(s) 54 can be disposed in the rear waist region 14 as illustrated in FIGS. 1-5. In general, the waist containment member 54 can help contain and/or absorb body exudates, especially low viscosity fecal matter, and as such, can be preferred to be in the rear waist region 14. In some embodiments, the absorbent article 10, 210 can have a waist containment member 54 disposed in the front waist region 12. A waist containment member 54 in the front waist region 12 can help contain and/or absorb body exudates, such as urine, in the front waist region 12. Although not as prevalent as in the rear waist region 14, in some circumstances, fecal material may also spread to the front waist region 12, and thus, a waist containment member 54 disposed in the front waist region 12 can help contain and/or absorb body exudates as well. In other embodiments, the absorbent article 10, 210 can have a waist containment member 54 in both the rear waist region 14 and the front waist region 12.

The waist containment member 54 can be disposed on the body facing surface 45 of the absorbent assembly 44. In some embodiments, such as in embodiments illustrated in FIGS. 1-2 and 5, the waist containment member 54 can be disposed on the body facing surface 56 of the bodyside liner 28. However, in some embodiments, such as the absorbent article 210 in FIG. 4, the waist containment member 54 can be disposed on a body facing surface 58 of the rear waist panel 15.

The waist containment member 54 can include a first longitudinal side edge 72 and a second longitudinal side edge 74. The first longitudinal side edge 72 can be opposite from the second longitudinal side edge 74. The distance between the first longitudinal side edge 72 and the second longitudinal side edge 74 can define a width 51 of the waist containment member 54 in the lateral direction 32, as shown in FIG. 2.

As illustrated in FIGS. 2 and 5, the waist containment member 54 can be configured such that the first longitudinal side edge 72 can be disposed laterally outward of the proximal end 64*a* of the base portion 64 of the containment flap 50. Similarly, the waist containment member 54 can be configured such that the second longitudinal side edge 74 can be disposed laterally outward of the proximal end 64*a* of the base portion 64 of the containment flap 52. The waist containment member 54 can be configured such that the width 51 of the waist containment member 54 can be greater than a lateral distance between longitudinal extending fold lines 25*a*, 25*b*, as shown in FIGS. 2 and 4.

The waist containment member 54 can also include a proximal portion (not shown) and a distal portion 78. The proximal portion can be coupled to the body facing surface 19 of chassis 11 (e.g., the body facing surface 45 of the absorbent assembly 44 or the body facing surface 56 of the bodyside liner 28) whereas the distal portion 78 of the waist containment member 54 can be free to move with respect to the chassis 11 and the absorbent assembly 44 when the absorbent article 10, 210 is in the relaxed configuration, such as shown in FIG. 5. When the waist containment member 54 is in a relaxed configuration, the distal portion 78 extends away from the chassis 11 and absorbent assembly 44 in a vertical direction, which is perpendicular to the plane defined by the longitudinal axis 29 and the lateral axis 31. A fold 79*a* can separate the proximal portion from the distal portion 78 of the waist containment member 54. As used in this context, the fold 79*a* separates the proximal portion from the distal portion 78 in that the fold 79*a* defines a transition between the proximal portion and the distal portion 78.

In some embodiments, the proximal portion of the waist containment member 54 can be coupled to the body facing surface 56 of the bodyside liner 28. In other embodiments, the proximal portion of the waist containment member 54 can be coupled to the body facing surface 58 of the rear waist panel 15. The proximal portion can be coupled to the body facing surface 45 by an adhesive, by pressure bonding, by ultrasonic bonding, by thermal bonding, and combinations thereof.

Because the distal portion 78 of the waist containment member 54 can freely move with respect to the absorbent assembly 44 when the absorbent article 10, 210 is in the relaxed configuration, the distal portion 78 can help provide a containment pocket 82 when the absorbent article 10, 210 is in the relaxed configuration. The containment pocket 82 can help provide a barrier to contain and/or can help absorb body exudates. The containment pocket 82 can be especially beneficial for containing and/or absorbing low viscosity fecal matter, which can be prevalent in younger children. The first longitudinal side edge 72 can be disposed laterally outward of the proximal end 64*a* of the base portion 64 of the containment flap 50, and thus, the containment pocket 82 can extend laterally outward of the proximal end 64*a* of the containment flap 50. Similarly, the second longitudinal side edge 74 can be disposed laterally outward of the proximal end 64*a* of the base portion 64 of the containment flap 52 and the containment pocket 82 can extend laterally outward of the proximal end 64*a* of the containment flap 52. Such a configuration provides waist containment member 54 with a wide containment pocket 82 to contain and/or absorb body exudates.

To help prevent lateral flow of body exudates that are contained by the containment pocket 82 of the waist containment member 54, the distal portion 78 of the waist containment member 54 can be bonded to the proximal portion of the waist containment member 54 and/or the body facing surface 19 of the chassis 11 near the first and second longitudinal side edges 72, 74, respectively. For example, FIG. 5 depicts tack-down regions 84 where the distal portion 78 of the waist containment member 54 can be bonded to the proximal portion of the waist containment member 54 and/or the body facing surface 19 of the chassis 11.

In preferred embodiments, the waist containment member 54 can include at least one elastic member and even more elastic members in further embodiments. Generally, the elastic member can span substantially from the first longitudinal side edge 72 to the second longitudinal side edge 74 of the waist containment member 54. The elastic member can be disposed in the distal portion 78 of the waist containment member 54, and preferably, is located near a free edge 88 of the distal portion 78 of the waist containment member 54.

A wide variety of elastomeric materials may be used for the elastic member(s) in the waist containment member 54. Suitable elastomeric materials can include sheets, strands or ribbons of natural rubber, synthetic rubber, elastic foams, or thermoplastic elastomeric materials (e.g., films). The elastomeric materials can be stretched and secured to a substrate forming the waist containment member 54, secured to a gathered substrate, or secured to a substrate and then elasticized or shrunk, for example, with the application of heat, such that the elastic retractive forces are imparted to the substrate forming the waist containment member 54.

The waist containment member 54 can be disposed to be coupled to the chassis 11 by being placed either over the containment flaps 50, 52 or under the containment flaps 50, 52. More specifically, the waist containment member 54 can be disposed on the body facing surface 19 of the chassis 11 such that the proximal portion of the waist containment member 54 is disposed over the base portion 64 of the first and the second containment flaps 50, 52, respectively. Alternatively, the waist containment member 54 can be disposed on the body facing surface 19 of the chassis 11 such that the proximal portion of the waist containment member 54 is disposed under the base portion 64 of the first and the second containment flaps 50, 52, respectively. Both configurations can provide advantages to the functioning of the waist containment member 54 to contain and/or absorb body exudates.

Where the proximal portion of the waist containment member 54 is disposed over the base portion 64 of the containment flaps 50, 52, the containment flaps 50, 52 can have an active flap elastic region 70 that longitudinally overlaps with the distal portion 78 of the waist containment member 54 when the absorbent article 10 is in the stretched, laid flat configuration, such as illustrated in FIG. 2. Additionally or alternatively, the tack-down region 71 may not extend from the rear waist edge 24 to the free edge 88 of the distal portion 78 of the waist containment member 54, such as illustrated in FIG. 2.

Where the proximal portion of the waist containment member 54 is disposed under the base portion 64 of the containment flaps 50, 52, the tack-down region 71 of the projection portion 66 of each of the containment flaps 50, 52 may longitudinally overlap with the distal portion 78 of the waist containment member 54. In some of these embodiments, the tack-down region 71 of projection portion 66 of each of the containment flaps 50, 52 can extend to the free edge 88 of the waist containment member 54 to further assist in containing exudates to the containment pocket 82 created by the waist containment member 54.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. The basis weight of the material forming the waist containment member 54 can vary, however, in a preferred embodiment, the basis weight can be between 8 gsm to 120 gsm, not including the elastic members 86 in the waist containment member 54. More preferably, the basis weight of the material comprising the waist containment member 54 can be between 10 gsm to 40 gsm, and even more preferably, between 15 gsm to 25 gsm.

Fastening System:

In an embodiment, the absorbent article 10 can include a fastening system. The fastening system can include one or more back fasteners 91 and one or more front fasteners 92. The embodiments shown in FIGS. 1 and 2 depict embodiments with one front fastener 92. Portions of the fastening system may be included in the front waist region 12, rear waist region 14, or both.

The fastening system can be configured to secure the absorbent article 10 the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2. As shown in FIG. 5, in some embodiments the waist containment member 54 can extend to back fasteners 91. In some embodiments, the waist containment member 54 can be coupled to the stretch component 94 of the back fasteners 91, either directly or indirectly. In some embodiments, the waist containment member 54 can extend to the longitudinal side edges 18, 20 of the absorbent article 10, 210.

Absorbent Body

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10, 210. The absorbent body 34 can have a length and width that can be less than or equal to the length and width of the absorbent article 10, 210.

In an embodiment, the absorbent body 34 can be composed of absorbent material, such as fibrous absorbent material and/or, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In another embodiment, the absorbent material of the absorbent body 34 can comprise only superabsorbent material. In an embodiment, the absorbent body 34 may be constructed of a single layer of materials, or in the alternative, may be constructed of two or more layers of materials.

When composed at least partially of fibrous material, various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber.

When composed at least partially of superabsorbent materials, such superabsorbent materials can be selected from natural, synthetic, and modified natural polymers and materials. The superabsorbent materials can be inorganic materials, such as silica gels, or organic compounds, such as cross-linked polymers.

If a spacer layer 48 is present, the absorbent body 34 can be disposed on the spacer layer 48 and superposed over the outer cover 26. The spacer layer 48 can be bonded to the outer cover 26, for example, by adhesive. In some embodiments, a spacer layer 48 may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer 48, can be positioned between the absorbent body 34 and the outer cover 26, such as illustrated in FIG. 5. The absorbent body 34 can be bonded to the fluid transfer layer 46 and/or the spacer layer 48.

According to some aspects of the present disclosure, the absorbent body 34, or at least one component of the absorbent body 34, may comprise absorbent structure 101 as described in more detail with respect to FIGS. 9A-9C and 10A-10B. The absorbent structure 101 may be the absorbent body 34 in some embodiments, such as those shown with respect to FIGS. 1-5. In other embodiments, the absorbent structure 101 may comprise only a portion of the absorbent body 34. For example, the absorbent structure 101 may be contained within the absorbent body 34 along with other material, such as one or more web materials and/or additional absorbent materials. Such other materials, along with absorbent structure 101, which in total form the absorbent body 34 may generally be identified as being part of the absorbent body 34 by their inclusion under fluid transfer layer 46—which may or may not wrap around side edges of the absorbent body 34 in different embodiments. By contrast, the absorbent body 34 and the fluid transfer layer 46, disposed between the spacer layer 48 or the outer cover 26 and the bodyside liner 28, may together comprise the absorbent system of the articles 10, 210.

In at least some embodiments, the absorbent material content of the absorbent structure 101 can comprise mostly superabsorbent material, by weight of the absorbent material of the absorbent structure 101. For example, the absorbent material content of the absorbent structure 101, by weight of the absorbent material of the absorbent structure 101, can comprise greater than 80% superabsorbent material, greater than 85% superabsorbent material, greater than 90% superabsorbent material, greater than 95% superabsorbent material, or may even comprise 100% superabsorbent material. In such embodiments, the remaining absorbent material content may comprise fibrous absorbent material, such as cellulosic fibers, or any other suitable absorbent material.

Figure 6:
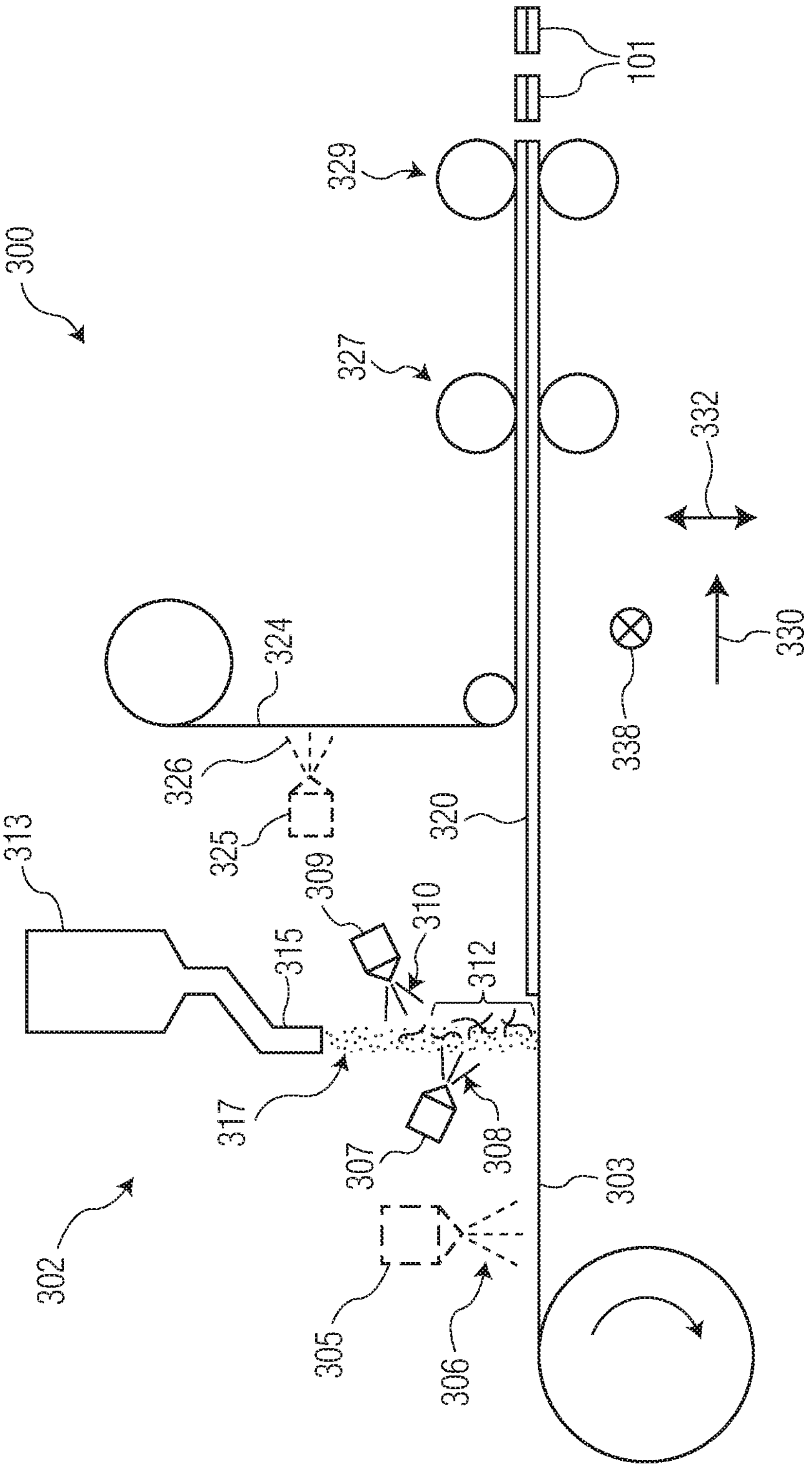
FIG. 6 is a process schematic depicting an exemplary method of manufacturing an absorbent structure according to the present disclosure.
Figure 7:
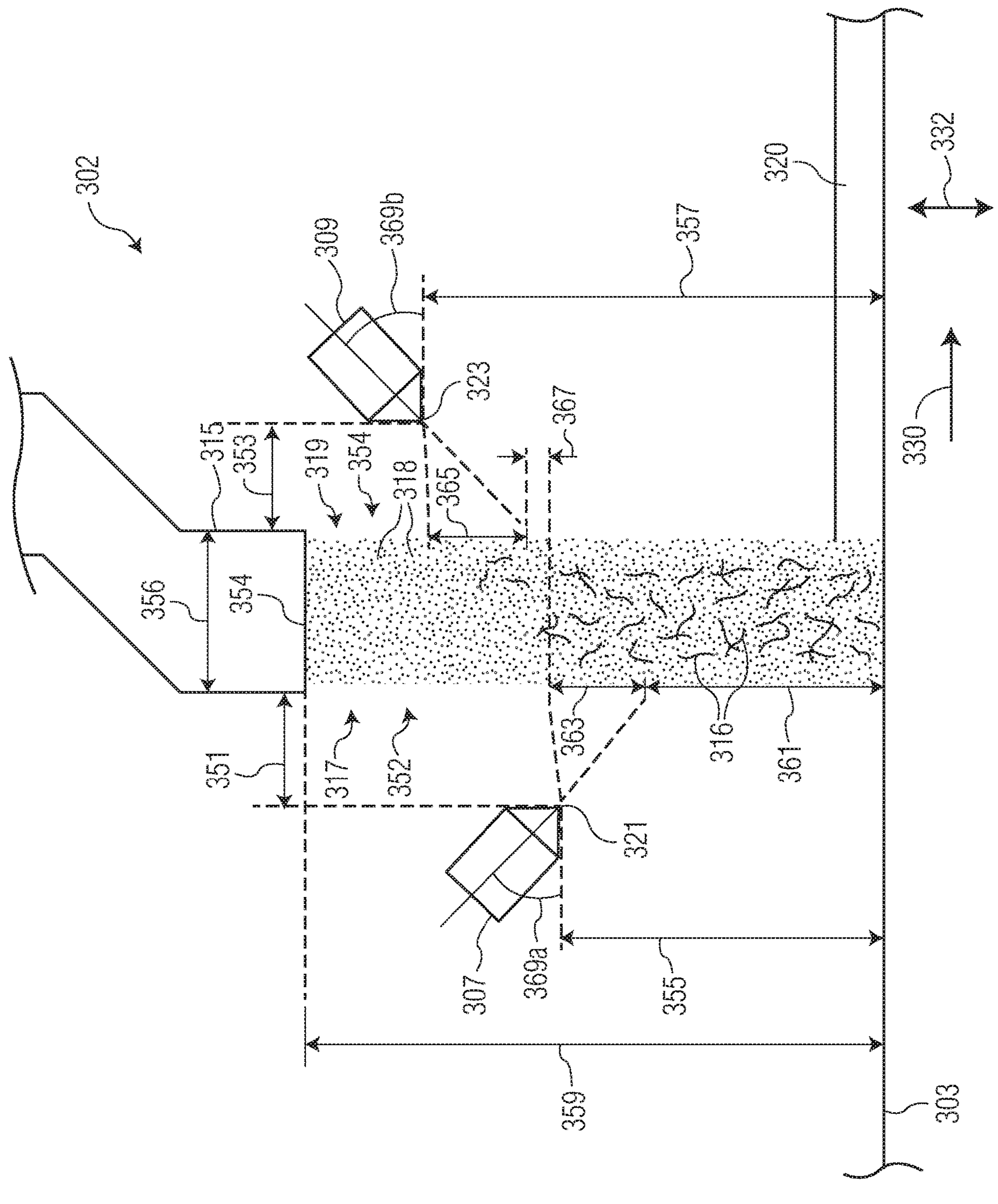
FIG. 7 is a process schematic depicting a portion of the exemplary method of FIG. 6.
Figure 8:
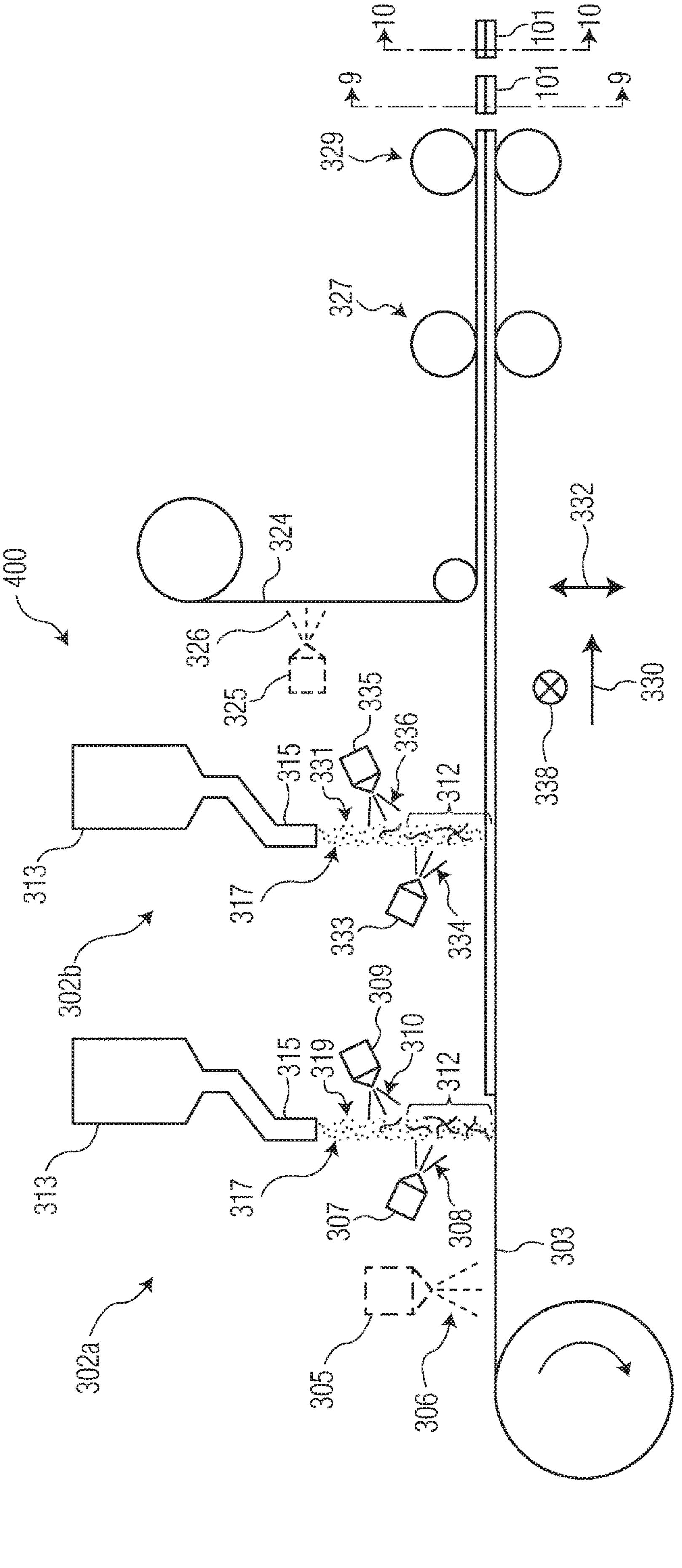
FIG. 8 is a process schematic depicting an alternative exemplary method of manufacturing an absorbent structure according to the present disclosure.

Absorbent structures 101 according to the present disclosure may be formed according to the processes disclosed herein, such as processes 300, 400 detailed in FIGS. 6-8. Such absorbent structures 101 may advantageously provide greater thinness, flexibility, superabsorbent material capture, pad integrity than absorbent structures formed by different processes and/or comprising different material or different relative amounts of material. Although the FIGS. 1-5 focus on description of a diaper absorbent article 10, 210, it should be understood that the absorbent structures 101 of the present disclosure may be used in any absorbent article—including but not limited to, diapers, diaper pants, training pants, youth pants, swim pants, feminine hygiene products, including, but not limited to, menstrual pads or pants, incontinence products and other adult care garments, medical garments, surgical pads and bandages, other personal care or health care garments, and the like.

FIG. 6 is an exemplary schematic depiction of absorbent structure formation process 300. Process 300 may include unwinding web material 303 and moving the web material 303 in a machine direction 330. In some exemplary embodiments, adhesive applicator 305 may apply adhesive 306 to the web material 303. The adhesive applicator 305 may apply the adhesive 306 to the web material 303 pneumatically or through various coating methods—or any other suitable application method—in the form of dots, beads, swirls, or any other suitable pattern. Although, it should be noted that the adhesive applicator 305 and adhesive 306 may be optional and not present in other embodiments. Accordingly, in such embodiments, adhesive 306 is not placed onto the web material 303.

In either case, the web material 303 may continue in the machine direction 330, arriving at an absorbent material deposition station 302. At the absorbent material deposition station 302, superabsorbent material 317 intermixes with one or more adhesives 308, 310 prior to depositing onto the web material 303, for example in a mixing region 312, and ultimately deposits onto the web material 303.

The superabsorbent material 317 flows from hopper 313 and through chute 315 toward the web material 303. The hopper 313 may be a bulk solid pump or feeder configured to maintain a consistent flow of the superabsorbent material 317 through the absorbent material deposition station 302. The flow rate of the superabsorbent material 317 out of the hopper 313 may be adjustable such that the hopper 313 can deliver different amounts of superabsorbent material 317, resulting in different basis weights of superabsorbent material 317 in the finished absorbent structures 101. Such differences in basis weights of superabsorbent material 317 may allow the formed absorbent structures 101 to be used in different absorbent end uses—such as in diapers, feminine articles, adult care garments, bandages and the like.

The chute 315 has a chute end 354 (as seen in FIG. 7) that is shown oriented in the vertical direction 332 such that the superabsorbent material 317, shown as individual particles 318 in FIG. 7, exits the chute 315 falling substantially in the vertical direction 332. The superabsorbent material 317 may preferably be fed through the absorbent material deposition station 302 by gravity, without any pneumatic force. As used herein, the vertical direction 332 is used to denote a direction perpendicular to the web material 303. The machine direction 330 may be defined as a direction parallel within the web material 303 and, accordingly, may be perpendicular to the vertical direction 332. In embodiments where the web material 303 is oriented in a horizontal direction with respect to gravity (e.g. perpendicular to the direction of gravity), the vertical direction 332 may be substantially aligned with respect to gravity. However, in other embodiments, the vertical direction 332 may be at an angle with respect to gravity—for example angles of up to 25 degrees difference with respect to gravity may be suitable for the vertical direction 332. Accordingly, in such embodiments, the superabsorbent material 317 may fall toward the web material 303 having a direction including a component in both the vertical direction 332 and the machine direction 330 (or potentially opposite the machine direction 330).

Additionally, regardless of the orientation of the vertical direction 332 with respect to gravity, the chute 315 may further be oriented in a non-perpendicular fashion with respect to the web material 303. For instance, the chute end 354 may be oriented perpendicular with respect to the web material 303 (as shown in FIG. 7) or it may be oriented so as to form an angle of greater than 0 degrees and less than 25 degrees with respect to a direction perpendicular to the web material 303.

In general, the amount of superabsorbent material 317 fed through the absorbent material deposition station 302 may be configured to result in absorbent structures 101 comprising superabsorbent material 317 disposed in amounts between 50 gsm and 1000 gsm, or between 100 gsm and 1000 gsm, or between 150 gsm and 1000 gsm, or between 200 gsm and 800 gsm, or between 250 gsm and 800 gsm, or between 300 gsm and 700 gsm, or between 350 gsm and 700 gsm, or between 400 gsm and 700 gsm, or between 450 gsm and 700 gsm, or between 500 gsm and 700 gsm, or between 400 gsm and 600 gsm, or between 500 gsm and 600 gsm. Such superabsorbent material 317 basis weight values for absorbent structures 101 may be particularly suitable for use in absorbent garments and feminine hygiene products. Although, further absorbent structures 101 that may be formed according to aspects of the present disclosure can have even smaller basis weights of superabsorbent material 317, such as between 5 gsm and 50 gsm, or 5 gsm and 30 gsm, or between 10 gsm and 30 gsm.

The chute opening 354 may have an opening width 356 (as measured where the superabsorbent material 317 exits the chute 315) in the machine direction 330. The opening width 356 may be between 2 mm and 30 mm, or between 5 mm and 25 mm, or between 5 mm and 20 mm, or between 7 mm and 15 mm. More specifically, opening widths 356 of between 2 mm and 10 mm are preferred when the amount of superabsorbent material 317 deposited by the absorbent material deposition station 302 is between 50 gsm and 300 gsm. Conversely, opening widths 356 of between 10 mm and 14 mm are preferred when the amount of superabsorbent material 317 deposited by the absorbent material deposition station 302 is between 300 gsm and 500 gsm, and opening widths 356 of between 14 mm and 20 mm are preferred when the amount of superabsorbent material 317 deposited by the absorbent material deposition station 302 is between 500 gsm and 1000 gsm.

These combinations of features—the gravity feed method and the chute opening width 356—may help to generate a "sheet" or "stream" of superabsorbent material 317 flowing toward the web material 303. The specified widths 356 may help to ensure that the stream 319 of superabsorbent material 317 has a sufficient width and/or density—particularly at the points where the adhesives 308 and/or 310 contact the stream 319, which can allow for the adhesives 308 and/or 310 to better penetrate the stream 319 and intermix with the superabsorbent material 317. These configurations can help to drive beneficial properties of the resulting absorbent structures 101, as described in more detail below. In some further embodiments, air streams or curtains may be used to help shape the stream 319 and/or to maintain a desired width and/or density of the stream. In such embodiments, the superabsorbent material 317 may be directed toward the web material 303 to some extent faster than solely by gravity, but such embodiments may be considered to still comprise a gravity feed system because the superabsorbent material 317 is not pneumatically or otherwise forced from the chute end 354.

As the superabsorbent material 317 falls toward the web material 303, adhesive applicators 307 and/or 309 may spray adhesive 308 and/or 310 toward the falling superabsorbent material 317. The adhesive 308 and/or 310 intermixes with the falling superabsorbent material 317 prior to the mixture of the superabsorbent material 317 and the adhesive 308 and/or 310 depositing onto the web material 303. FIG. 7 is a close-up schematic depiction of the absorbent material deposition station 302, showing more details regarding the adhesive applicators 307 and/or 309, the adhesives 308 and/or 310.

The amount of adhesives 308 and/or 310 applied by adhesive applicators 307 and/or 309 may generally be applied at add-on percentages of less than 7%, or less than 6%, or less than 5%, or less than 4%, or less than 3%, or less than 2%. In other embodiments, the add-on percentages may be between 2% and 7%, or between 3% and 7%, or between 4% and 7%, or between 5% and 7%, or between 6% and 7%. As used herein, the term "add-on" amount or percentage is the amount of described material added such that a resulting weight of the described material within the absorbent structure 101 has the desired relation to a weight of the absorbent material within the absorbent structure 101. As one illustrative example, where the superabsorbent material 317 is disposed in an absorbent structure 101 at a basis weight of 500 gsm, and where the adhesives 308 and/or 310 were applied at an add-on rate of 5%, the resulting basis weight of the adhesive 308 and/or 310 in the formed absorbent structure would be 25 gsm (5% of 500 gsm).

As described, in some embodiments the absorbent material deposition station 302 can comprise two adhesive applicators 307 and 309. The first adhesive applicator 307 may be positioned upstream (relative to the process direction 330) of the chute 315 while the second adhesive applicator 309 may be positioned downstream of the chute 315. The superabsorbent material 317 may form a stream 319 of superabsorbent material 317 as it falls toward the web material 303. Where the adhesive applicator 307 is positioned on the upstream side of the chute 315, the adhesive applicator 307 is configured to spray the first adhesive 308 at the first side 352 of the stream 319 of superabsorbent material 317.

The adhesive applicator 307 may be configured to spray the first adhesive 308 such that the first adhesive 308 contacts the first side 352 of the stream 319 of superabsorbent material 317 along a portion of the stream 319 having a length 363 along the stream 319. In some embodiments, the length 363 may be insubstantial in that the first adhesive 308 may be sprayed as a stream which has minimal-to-no spread. However, in other embodiments, the first adhesive 308 may have some spread and accordingly the length 363 could be between 2 mm and 10 mm, or between 2 mm and 6 mm, or between 2 mm and 4 mm.

In order to allow sufficient time for the first adhesive 308 to intermix with the stream 319 of the superabsorbent material 317 prior to the mixture of the first adhesive 308 and the superabsorbent material 317 depositing onto the web material 303, the first adhesive 308 may generally contact the stream 319 at a first contact point located a distance 361 away from the web material 303. The distance 361 may be between 4 mm and 40 mm, or between 4 mm and 35 mm, or between 5 mm and 30 mm, or between 6 mm and 25 mm. Where the first adhesive 308 is sprayed in a spread fashion and contacts the stream 319 along some length 363, the first contact point, and accordingly the distance 361, is measured with respect to the center of the length 363 along which the first adhesive 308 contacts the stream 319.

To achieve such distances 361, the nozzle 321 may be positioned a distance 355 away from the web material 303 and a distance 351 away from the chute 315. These distances 355, 351 may be adjusted to achieve the desired distance 361. As some non-limiting examples, the distance 355 may generally be between 5 mm and 40 mm, or between 10 mm and 30 mm. As a comparison, the chute 315 may be positioned a distance 359 away from the web material 303. The distance 359 may be between 50 mm and 90 mm, or between 60 mm and 80, or between 70 mm and 80 mm. Distances 359 higher than 70 mm, or 80 mm, or 90 mm may result in undesirable spreading of the stream 319. Distances lower than 60 mm or 50 mm may result in there being insufficient space between the chute 315 and the web material 303 to allow for sufficient mixing of the superabsorbent material 317 and the first adhesive 308 (or the second adhesive 310 described in more detail below).

It has been further found that the angle **369*a* at which the nozzle 321 is oriented with respect to the machine direction 330 may be important in achieving a desired level of mixing between the first adhesive 308 and the stream 319. Preferably, the angle 369*a*** may vary between 40 degrees and 80 degrees, or between 45 degrees and 75 degrees, or between 50 degrees and 70 degrees.

The adhesive applicator 309 may be configured similarly to the adhesive applicator 307. The adhesive applicator 309 can spray the second adhesive 310 such that the second adhesive 310 contacts the second side 354 of the stream 319 of superabsorbent material 317 along a portion of the stream 319 having a length 365 along the stream 319. Accordingly, the length 365 may be insubstantial in that the second adhesive 310 may be sprayed as a stream which has minimal-to-no spread. In other embodiments, the second adhesive 310 may have some spread such that the length 365 may vary between 2 mm and 10 mm, or between 2 mm and 6 mm, or between 2 mm and 4 mm.

To allow sufficient time for the second adhesive 310 to intermix with the stream 319 of the superabsorbent material 317 prior to the mixture of the second adhesive 310 and the superabsorbent material 317 depositing onto the web material 303, the second adhesive 310 may generally contact the stream 319 at a second contact point on the stream 319 located a distance away from the web material 303 equal to distance 367 added to distance 361. The distance 367 plus distance 361 may generally be between 4 mm and 40 mm, or between 4 mm and 35 mm, or between 5 mm and 30 mm, or between 6 mm and 25 mm. Additionally, where the second adhesive 310 is sprayed in a spread fashion and contacts the stream 319 along some length 365, the second contact point, as well as the distance 367 added to the distance 361, is measured with respect to the center of the length 365 along which the second adhesive 310 contacts the stream 319 (and with respect to the center of the length 363 if the first adhesive 308 contact the stream 319 for some appreciable length 363).

It can be understood that the distance 361 and the distance 367 added to the distance 361 overlap in their preferred ranges. According to some preferred embodiments, the distance 361 is less than the distance 367 added to the distance 361. For example, it may be preferred that the applicator 307 is positioned closer to the web material 303 than the applicator 309. In such embodiments, the distance 361 may be preferred to be between 4 mm and 22 mm, or between 4 mm and 20 mm, or between 6 mm and 15 mm. The distance 367 added to the distance 361 may be greater than the distance 361 by between 5 mm and 15 mm, or between 6 mm and 13 mm, or between 6 mm and 11 mm, e.g. the distance 367 may be between 5 mm and 15 mm, or between 6 mm and 13 mm, or between 6 mm and 11 mm. In such embodiments, the distance 367 may represent a spacing between the first contact point where the first adhesive 308 contacts the stream 319 and the second contact point where the second adhesive 310 contacts the stream 319.

It has been found that spraying the adhesives 308 and/or 310 at the stream 319 may cause the stream 319 to bend in the direction of the spray. Without being limited by theory, it is thought that the force of the adhesives 308 and/or 310 contacting the stream and/or the optional pattern air supplied by the applicators 307 and/or 309 can cause this bending of the stream 319. Accordingly, where first contact point where the first adhesive 308 contacts the stream 319 is at a lower point than the second contact point where the second adhesive 310 contacts the stream 319, the stream 319 may bend in the machine 330 just prior to depositing onto the web material 303. This bending of the stream 309 in the machine direction 330 helps to ensure a smooth deposition of mixture of the superabsorbent material 317 and the first adhesive 308 (and optionally the second adhesive 310), resulting in a more uniform mixture 320, which has many benefits in terms of capture and stabilization of the superabsorbent material 317, integrity of the resulting absorbent structure 101, and uniformity of the distribution of the superabsorbent material 317 and the first adhesive 308 (and optionally the second adhesive 310).

As with the nozzle 321, the nozzle 323 may be positioned a distance 357 away from the web material 303 and a distance 353 away from the chute 315 in order to achieve the desired distance 367 added to the distance 361. The angle **369*b* at which the nozzle 323 is oriented with respect to the web of material 303 may further be similar to the angle 369*a*. For example, the angle 369*b* may vary between 40 degrees and 80 degrees, or between 45 degrees and 75 degrees, or between 50 degrees and 70 degrees. In at least some embodiments, the angle 369*a* and the angle 369*b* can be the same, while in other embodiments the angles 369*a*, 369*b*** are different.

The applicators 307 and/or 309 may be preferably configured to spray the adhesives 308 and/or 310 in a substantially random pattern. It has been found that spray patterns that are more randomized, irregular, or erratic may produce better results in terms of performance of the absorbent structures 101—such as in terms of capture and stabilization of the superabsorbent material 317, integrity of the resulting absorbent structure 101, and uniformity of the distribution of the superabsorbent material 317 and the adhesives 308 and/or 310. One such exemplary spray pattern is the pattern produced by the Universal™ Signature™ Spray Nozzles available from the Nordson Corporation having headquarters at 28601 Clemens Road, Westlake, OH 44145 USA. However, in other embodiments, different adhesive spray patterns which are more regular and less randomized, but still considered a random pattern, may be sufficient to produce absorbent structures 101 having desirable performance properties. It is further contemplated that some non-random spray patterns may also be sufficient to produce absorbent structures 101 having desirable performance properties.

Although shown in FIG. 7 as comprising two adhesive applicators 307 and/or 309, in some embodiments the absorbent material deposition station 302 may only comprise one of the adhesive applicators 307 and/or 309. Further, although shown, and described above, with the adhesive applicator 307 directing adhesive 308 to the first side 352 of the stream 319 (which is the upstream side of the stream 319) positioned closer to the web material 303 than the adhesive applicator 309, this orientation is not required in all embodiments. For example, in further embodiments, the adhesive applicator 307 may be positioned further away from the web material 303 than the adhesive applicator 309, while still being positioned on the upstream side of the stream 319. In any of these such embodiments, the distances between the first contact point and the second contact point with respect to each other and with respect to the web material described previously may be reversed. That is, the distance 361 may describe the distance between the second contact point and the web material 303 while the distance 367 added to the distance 361 may describe the distance between the first contact point and the web material 303 (with the distance 367 describing the distance between the first contact point and the second contact point).

As the web 303 passes the absorbent material deposition station 302, a deposited mixture 320 of the mixture of the adhesives 308 and/or 310 and the superabsorbent material 317 forms. In embodiments where the adhesive applicator 305 was used to spray the adhesive 306 onto the web material 303, the adhesive 306, along with the adhesives 308 and/or 310 operate to immobilize the superabsorbent material 317 onto the web material 303. In embodiments where the adhesive applicator 305 is not used, only the adhesives 308 and/or 310 operate to immobilize the superabsorbent material 317 onto the web material 303.

During the deposition of the mixture 320, vacuum energy may optionally be applied to the web material 303. For example, web material 303 may be supported by a forming surface—such as a forming belt or forming drum as is typical in the art. Vacuum energy may be applied to the forming surface such that air is drawn through the forming surface from the side where the web material 303 is located. Accordingly, the web material 303, along with the mixture 320 as it is falling toward the web material 303, is drawn to the forming surface due to the applied vacuum energy. Such vacuum energy may help to control the spread of the mixture 320 as it is falling toward the web material 303, thereby helping to form a relatively more uniform absorbent structure 101. It has been found that particularly high pressure differentials are preferred at the forming surface—above and beyond typical pressure differentials in the art. For example, it may be preferred that the vacuum energy produces a pressured differential of greater than 0.25 m of water at the forming surface. In further embodiments, it my be more preferable for even higher pressure differentials, such as greater than 0.35 m of water, or greater than 0.5 m of water, or greater than 0.65 m of water, as measured at the forming surface.

A web material 324 may further be applied to the deposited mixture 320. In some embodiments, an adhesive applicator 325 may spray an adhesive 326 onto the web material 324 prior to the web material 324 being positioned onto the deposited mixture 320. Although, it should be understood that the adhesive applicator 325 is only optional and may not be present in some embodiments. Where present, the applied adhesive 326 may operate to more closely couple the web material 324 to the deposited mixture 320 and/or to further immobilize the superabsorbent material 317 within the formed absorbent structure.

According to some aspects of the present disclosure, the combination of the web material 303, the deposited mixture 320, and the web material 324 may pass through one or more nip stations 327 to help compress the components together. In general, the nip station 327 may apply a pressure to the combination of the web material 303, the deposited mixture 320, and the web material 324 of between 0.5 pounds per linear inch (PLI) (88 N/m) and 1.5 PLI (263 N/m), or between 0.75 PLI (131 N/m) and 1.25 PLI (219 N/m). Such pressures help to further connect the deposited mixture to the web materials 303, 324. Although not required in all embodiments, it may be preferred for the nip station 327 to be positioned in relatively close proximity to the material deposition station 302 such that the adhesives 308 and/or 310 is still open when the combination of the web material 303, the deposited mixture 320, and the web material 324 passes through the nip station 327.

After the one or more nip stations 327, the combination of the web material 303, the deposited mixture 320, and the web material 324 may pass to a cutting station 329 where the connected length of the web material 303, the deposited mixture 320, and the web material 324 is cut into individual absorbent structures 101. These individual absorbent structures 101 may then be combined into a manufacturing process for producing the various absorbent products described herein.

FIG. 8 depicts is an exemplary schematic depiction of an alternative absorbent structure formation process 400. The process 400 is similar to process 300, except the process 400 employs two absorbent material deposition stations 302*a*, 302*b*. It has been found that there are some advantages of employing two absorbent material deposition stations 302*a*, 302*b* over a single absorbent material deposition station 302. For example, as the desired amount of deposited superabsorbent material 317 gets higher, the lower the ability of a single absorbent material deposition station 302 to form an absorbent structure 101 having desired performance properties. If the desired amount of deposited superabsorbent material 317 gets too high, a single absorbent material deposition station 302 may not be able to form a mixture of superabsorbent material 317 and adhesive which sufficiently immobilizes the superabsorbent material 317—particularly at desired low adhesive add-on amounts. For instance, in such examples, a superabsorbent material capture property of such formed absorbent structures 101 may fall below a desired value.

Conversely, the same desired amount of deposited superabsorbent material 317 may be able to be sufficiently immobilized by employing two absorbent material deposition stations 302*a*, 302*b* such that the resulting absorbent structures 101 have a desired superabsorbent material capture value. Additionally, employing two absorbent material deposition stations 302*a*, 302*b* may allow for increased production rates—even at lower superabsorbent material 317 amounts and higher adhesive add-on amounts. Accordingly, in the process 400, after the mixture of superabsorbent material 317 and adhesives 308 and/or 310 is deposited onto the web material 303 at absorbent material deposition station 302*a* (which may be equivalent to absorbent material deposition station 302 of FIGS. 6 and 7), the web material 303 and the deposited mixture of superabsorbent material 317 and adhesives 308 and/or 310 moves onto absorbent material deposition station 302*b*.

Similar to absorbent material deposition station 302*a*, absorbent material deposition station 302*b* may be configured to direct a second stream 331 of superabsorbent material 317 toward the web 303 and the already deposited mixture of superabsorbent material 317 and adhesives 308 and/or 310. The absorbent material deposition station 302*b* may comprise adhesive applicators 333 and/or 335 which may spray adhesive 334 and/or 336 toward the second stream 331 of falling superabsorbent material 317. The adhesive 334 and/or 336 intermixes with the falling superabsorbent material 317 prior to the mixture of the superabsorbent material 317 of the second stream 331 and the adhesive 334 and/or 336 depositing onto the web material 303 and the previously deposited mixture of superabsorbent material 317 and adhesives 308 and/or 310.

According to some aspects of the present disclosure, the absorbent material deposition station 302*b* can comprise two adhesive applicators 333 and 335. With respect to the absorbent material deposition station 302*b*, the first adhesive applicator 333 (which may be the third adhesive applicator of the process 400) may be positioned upstream (relative to the process direction 330) of the chute 315 of the second deposition station 302*b* while the second adhesive applicator 335 (which may be the fourth adhesive applicator of the process 400) may be positioned downstream of the chute 315 of the second deposition station 302*b*. The adhesive applicator 333 is configured to spray the first adhesive 334 (which may be the third adhesive of the process 400) at a first side of the second stream 331 of superabsorbent material 317. The adhesive applicator 335 is configured to spray the second adhesive 336 (which may be the fourth adhesive of the process 400) at a second side of the second stream 331 of superabsorbent material 317.

Generally, the positions, locations, distances, and other features and optional components or features of the absorbent material deposition station 302 described with respect to FIG. 7 may be the same as for absorbent material deposition station 302*a*. Likewise, the absorbent material deposition station 302*b* may be the same or substantially similar to the absorbent material deposition station 302*a*. The absorbent material deposition station 302*b* may be positioned between 0.25 m and 3.0 m, or more preferably between 0.25 m and 2.0 m, or even more preferably between 0.25 m and 1.0 m.

Turning back to web materials 303 and 324, as shown in FIGS. 6 and 8, the web material 324 may be coupled to the deposited mixture 320 of the superabsorbent material 317 and the adhesives 308, 310, 334, and/or 336 to form the absorbent structures 101. Some alternative embodiments according to aspects of the present disclosure may forgo the web material 324 altogether. In such embodiments, the web material 303 may be wide enough that, after the mixture 320 is deposited onto the web material 303, the web material 303 is wrapped around the mixture 320 to form the absorbent structure 101.

Figure 9A:
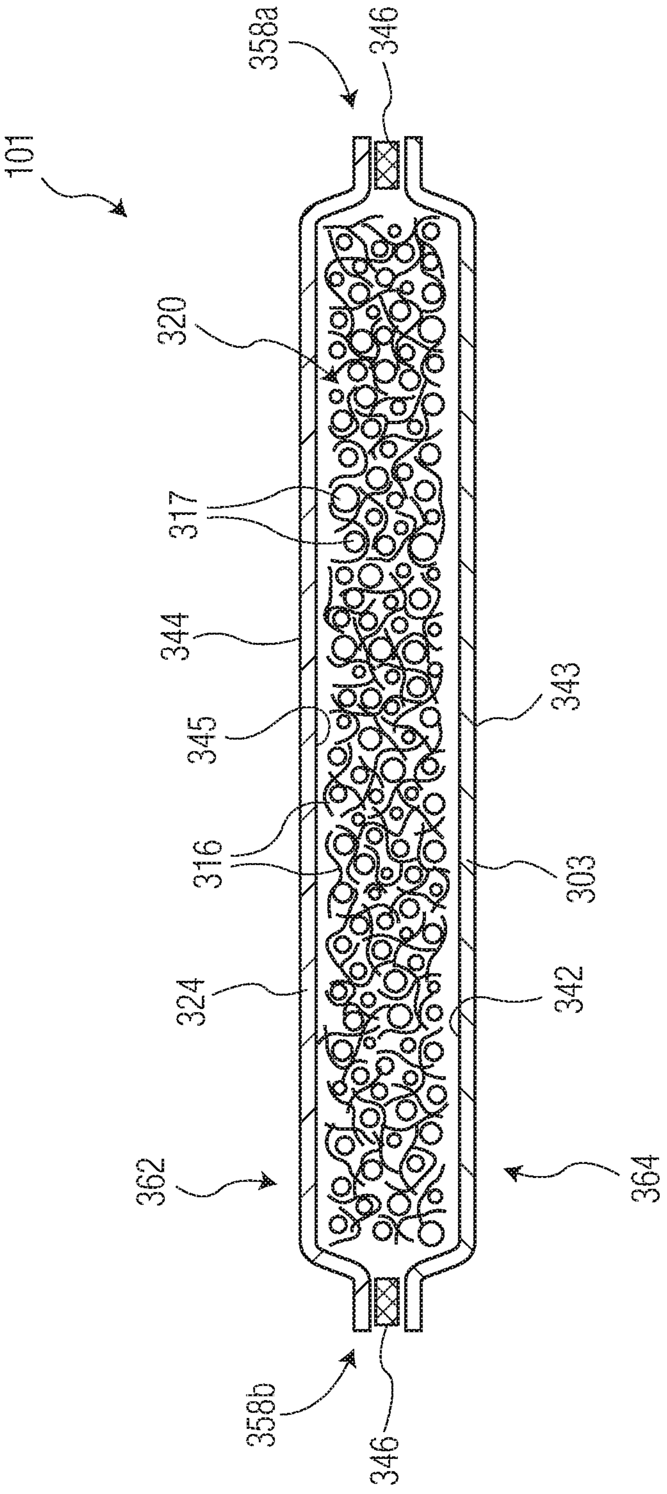
FIGS. 9A-9C are different exemplary front cross-sectional views of an absorbent structure formed according to a method of manufacturing according to aspects of the present disclosure, taken along line 9-9 from FIG. 8.
Figure 9B:
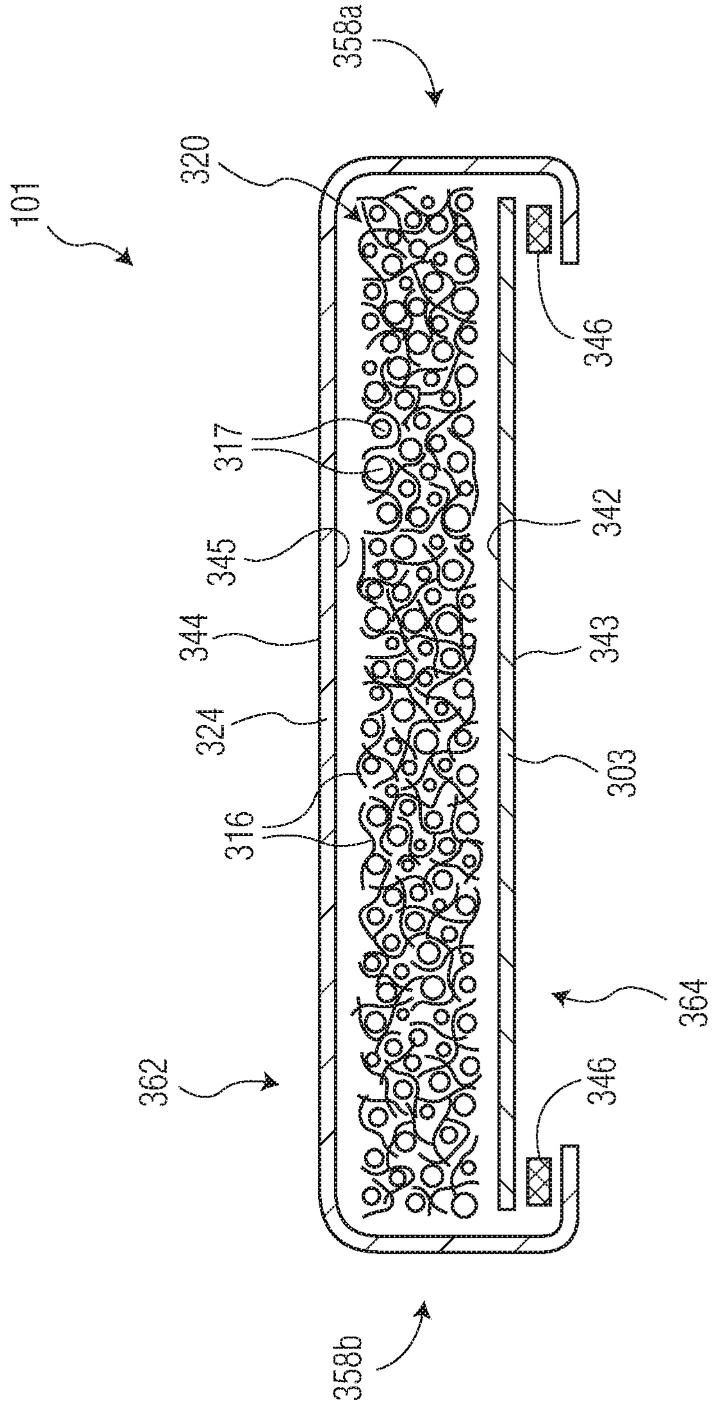
Figure 9C:
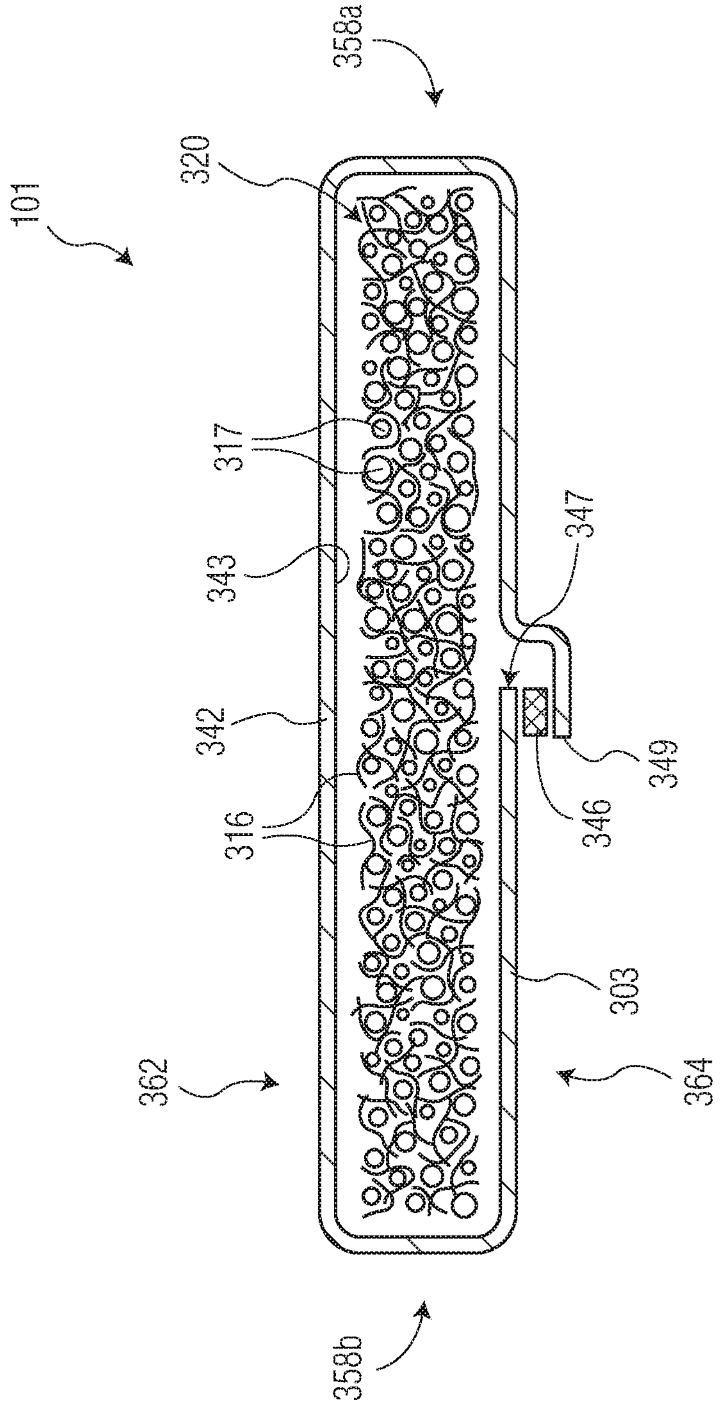

FIGS. 9A-9C depict different cross-sections of exemplary absorbent structures 101 according to aspects of the present disclosure. The cross-sections representing FIGS. 9A-9C are taken along line 9-9 of FIG. 8, showing different configurations of the mixture 320, the web material 303, and web material 324, where present.

FIG. 9A depicts an embodiment of an absorbent structure 101 of the present disclosure comprising web material 303 and web material 324, with mixture 320 disposed between web material 303 and web material 324. The web material 303 and web material 324 may have top surfaces 342 and 344, respectively, and bottom surfaces 343 and 345, respectively. In some exemplary embodiments according to FIG. 9A, the mixture 320 may be disposed on top surface 342 of web material 303 and on bottom surface 345 of web material 324. In some of these embodiments, absorbent structure 101 may further comprise seaming adhesives 346 disposed outboard of the mixture 320 and bonding the bottom surface 345 of web material 324 to the top surface 342 of web material 303. Such seaming adhesives 346 may help to seal the side edges 358*a*, 358*b* of the absorbent structure 101 closed. However, it should be understood that such adhesives 346 are not necessary in all embodiments—many embodiments sufficiently capture the superabsorbent material 317 such that little to no superabsorbent material 317 may escape out of the absorbent structure 101, even without the seaming adhesive 346.

Where present, the seaming adhesives 346 may be applied by adhesive applicators prior to or after deposition of the mixture 320 (for example, optional adhesive applicators 305 and/or 325 may apply the seaming adhesives 346). Alternatively, the seaming adhesives 346 may be applied during deposition of the mixture 320 by adhesive applicators 307, 309, 333 and/or 335, for example where the adhesive spray from the adhesive applicators 307, 309, 333 and/or 335 is wider than the stream or streams of superabsorbent material 317. In other embodiments, however, absorbent structure 101 may not include any seaming adhesives 346. In such embodiments the adhesives 308, 310, 334, and/or 336 may be sufficient to bond the web material 303 to the web material 324.

FIG. 9B depicts another embodiment of an absorbent structure 101 of the present disclosure comprising web material 303 and web material 324, with mixture 320 disposed between web material 303 and web material 324. In this embodiment, in contrast to the embodiment of FIG. 9A, instead of the bottom surface 345 of web material 324 bonded to the top surface 342 of web material 303, the top surface 344 of web material 324 may be bonded to the top surface 342 of web material 303. For example, the web material 324 may wrap at least partially around the mixture 320, sometimes termed a C-wrap, such that the bottom surface 345 of web material 324 is disposed about both a portion of a first side of the mixture 320 and a second side of the mixture 320. In the embodiment shown in FIG. 9B, the web material 324 may be disposed between the mixture 320 and the web material 303 where the web material 324 and the web material 303 overlap. Although, in other embodiments, the web material 324 may wrap around both of the mixture 320 and the web material 303 such that the web material 303 is disposed between the mixture 320 and the web material 324 where the web material 324 and the web material 303 overlap.

In the embodiment shown in FIG. 9B, the absorbent structure 101 may include seaming adhesives 346 connecting the top surface 344 of web material 324 to the top surface 342 of web material 303 proximate lateral edges of the absorbent structure 101. Although, it should be understood that such seaming adhesives 346 are optional and may not be present in all embodiments. Where present, seaming adhesives 346 may be applied for example, by optional adhesive applicators 305 and/or 325, or may be applied by one or more of adhesive applicators 307, 309, 333 and/or 335.

FIG. 9C depicts another embodiment of an absorbent structure 101 of the present disclosure comprising only web material 303. In this embodiment, web material 303 wraps around the mixture 320, for example forming a C-wrap configuration. As shown in FIG. 9C, the web material 303 has web end portions 347 and 349. In some exemplary embodiments according to FIG. 9C, the web material 303 may wrap around the mixture 320 such that the web end portions 347 and 349 overlap each other. As shown in FIG. 9C, such configurations may further include one or more seaming adhesives 346 disposed between the web end portions 347 and 349 and bonding the web end portions 347 and 349 of the material 303 together. Although, such seaming adhesives 346 are optional and may not be present in other embodiments. In further embodiments according to FIG. 9C, the web end portions 347 and 349 may be spaced from each other such that the web end portions 347 and 349 do not overlap. In such embodiments, a portion of the mixture 320 may be left uncovered by the web material 303.

With respect to FIGS. 9A-9C, the exemplary absorbent structures 101 may have top sides 362 and bottom sides 364. However, it should be understood that these absorbent structures 101 may be used in any orientation. For example, in some instances, the described absorbent structures 101 may be placed into an absorbent article, such as article 10, with the top side 362 disposed most closely to the body facing surface 19. In other instances, the absorbent structures 101 may be placed into an absorbent article such as article 10 with the bottom side 364 disposed most closely to the body facing surface 19.

Where web material 303 forms the top side 362 of the absorbent structure 101 and where the top side 362 is disposed most closely to the body facing surface 19, the web material 303 may be any suitable nonwoven material—for instance, a bonded carded web, a meltblown material, a spunbond material, including spunbond and meltblown combination webs commonly referred to SMS webs or SMMS webs or the like, a spunlace material, a hydroentangled material, an airlaid material, a coform material, or may be a material formed according to mixtures of technologies used to form the above described materials such as a spunbond-meltblown-spunbond material or other such similar materials. Typical basis weights for such web materials 303 may range between 8 gsm to 200 gsm, or between 10 gsm and 150 gsm, or between 10 gsm and 100 gsm. Alternatively, the web material 303 may be formed of wetlaid fibrous materials such as uncreped through air dried tissue or creped tissue, or other material sheets made from cellulosic fibers. The web material 303 may further comprise a combination of nonwoven and fibrous materials, including fiberized pulp captured on top of or between nonwoven materials or wetlaid fibrous materials. In such embodiments, the fiberized pulp may be densified to form the web material 303—prior to its use in capturing superabsorbent 317 and adhesive 308 and/or 310.

Without respect to any specific type of material, it has been found that web material 303 should ideally have sufficient air permeability to allow vacuum air flow to pass through the web material 303 and to at least partially entrain the streams 319 (and optionally 331) of superabsorbent material 317 and adhesives 308 and/or 310 (and optionally 334 and/or 336) in such vacuum air flow. For example, it has been found that an air permeability of the web material 303 should be greater than 25 standard cubic feet per minute (SCFM) of air (0.71 standard cubic meters per minute (SCMM)). In further embodiments, it may be more preferable for the web material 303 to have an air permeability of greater than 50 SCFM (1.4 SCMM), or greater than 75 SCFM (2.1 SCMM). Such measurements of air permeability may be made consistent with standard industry practices for measuring air permeability. According to some examples, such air permeability measurements may be made with a Frazier Instruments Model LP air permeability tester from Frazier Instruments (offices in Hagerstown, Maryland), a Textest FX 3300 air permeability unit from Textest (offices in Schwerzenbach, Switzerland), or equivalent test unit.

Again, where the web material 303 forms the top side 362 of the absorbent structure 101 and where the top side 362 is disposed most closely to the body facing surface 19 it may be preferable that the fibers, or at least the surface fibers, of the web material 303 have sufficient wettability to allow fluid intake, fluid flow, and fluid distribution through the web material 303 to the superabsorbent material 317. In some embodiments, the wettability may come from the composition of the fiber. For instance, the fibers forming the web material 303 may be inherently wettable fibers include such as natural cellulosic fibers derived from cotton, wood, or other fibers. Other examples of an inherently wettable fiber include a reconstituted cellulosic fiber such as a rayon fiber. In further embodiments, the fibers forming the web material 303 may not be inherently wettable, but may be changed to be wettable, such as by addition of a surfactant treatment to the fibers, or at least to the surface fibers. The surfactant treatment may be applied at least to the surface fibers in a continuous or discontinuous manner. In other embodiments, a surfactant treatment can be added internally to the fiber which will ultimately migrate to the surface of the fiber.

Where web material 324 forms the bottom side 364 of the absorbent structure 101 and where the bottom side 364 is disposed most closely to the body facing surface 19, the web material 324 may be any suitable nonwoven material—for example, any of those recited with respect to web material 303. Additionally, the web material 324 may be preferred to have any of the same properties as were described above with respect to web material 303. Where web material 324 forms the bottom side 364 of the absorbent structure 101 and where the top side 362 is disposed most closely to the body facing surface 19, the web material 324 may also be any of the materials described above with respect to web material 303, including having any of the properties and their described ranges.

The adhesives 308 and/or 310 may generally comprise hot-melt adhesives, and the nozzles 321, 323 may be configured to project the adhesives 308 and/or 310 toward the stream 319 of superabsorbent material 317 such that the adhesives 308 and/or 310 form adhesive filaments 316. Desirably, the adhesives 308 and/or 310 should have sufficient tack and cohesion. An exemplary suitable adhesive is the TECHNOMELT DM 5402U adhesive available from Henkel Corporation, a company having offices in Rocky Hill, Connecticut. This suitable adhesive is a styrenic block copolymer based hot melt adhesive design to have high cohesion and strong specific adhesion to provide good fixation of the superabsorbent material 317 in the absorbent structure under both wet and dry conditions. It may further be generally preferable for the adhesives 308 and/or 310 to be non-water soluble in order to help retain the positioning of the superabsorbent material 317 within the structure 101 after one or more liquid insults. It has been found that rubber-based adhesives may be preferable in that they may produce structures 101 which perform superior to other adhesives, such as standard construction adhesives or olefin-based adhesives.

In general, the adhesive applicators 307 and/or 309 operate to spray the adhesives 308 and/or 310 such that the adhesives 308 and/or 310 form adhesive filaments 316 which contact the stream 319. The adhesive applicators 307 and/or 309 may be generally configured to spray the adhesives 308 and/or 310 such that the adhesives 308 and/or 310 form filaments 316 having preferred diameters. It has been found that it may be preferable for the filaments 316 to have diameters of between 25 micrometers (microns) and 150 microns, or between 50 microns and 100 microns, or between 75 microns and 100 microns. These ranges of filament diameters have been shown to work together well with superabsorbent material 317 having the below described particle diameters in order to provide for beneficial performance properties of the structures 101.

Although the above described adhesive properties have been described with respect to adhesives 308 and/or 310, where present the adhesives 334 and/or 336 may have properties similar to those described above with respect to adhesives 308 and/or 310. Likewise, where present, the applicators 333 and/or 335 may be configured to spray the adhesives 334 and/or 336 in a similar manner to how the adhesive applicators 307 and/or 309 are configured to spray the adhesives 308 and/or 310. For example, the diameters of the filaments 316 formed by the adhesives 334 and/or 336 being sprayed from applicators 333 and/or 335 may be similar to the diameters described above with respect to filaments 316 formed by the adhesives 308 and/or 310 being sprayed from applicators 307 and/or 309.

Additionally, it has been found that the sizes of the individual particles 318 of the superabsorbent material 317 may drive certain desired properties of the formed absorbent structures 101. For instance, particle size of the individual particles 318 may at least partially drive pad integrity and superabsorbent material capture values, particularly in conjunction with the described structural features of the adhesive filaments 316. For example, it has been found that where the bulk superabsorbent material 317 has mean particle sizes ranging from between 150 and 1000 micrometers (microns) in diameter provide good results—especially in conjunction with the above described adhesive filament 316 diameters. In such embodiments, it may be preferred that at least 50% of the mass of the bulk superabsorbent material 317 have diameters larger than 180 microns. In other embodiments, it may be preferred that at least 60%, or at least 70%, or at least 80% of the mass of the bulk superabsorbent material 317 have diameters larger than 180 microns. In further embodiments, it may more preferable that at least 50% of the mass of the bulk superabsorbent material 317 have diameters larger than 300 microns, or that at least 60%, or at least 70%, or at least 80% of the mass of the bulk superabsorbent material 317 have diameters larger than 300 microns.

Where the bulk superabsorbent material 317 mean particle size is too low, such as lower than 300 microns, or lower than 180 microns, the formation and performance of the structures 101 can be affected to a detrimental degree. For example, such small mean particle sizes may affect the ability of the superabsorbent material 317 to fall in a relatively uniform stream from the chute 315, thereby resulting in relatively more non-uniformity of the superabsorbent material 317 and adhesives 308 and/or 310 (and optionally 334 and/or 336). Additionally, such small average particle sizes may begin to approach the average diameter size of the adhesive filaments 316, both affecting capture of the individual particles 318 by the adhesive filaments 316 and reducing absorptive performance because the adhesive filaments 316 would more readily block liquid from accessing all portions of the individual particles 318. Determining the masses of different portions of particles of the bulk superabsorbent material 317 may be performed by any classification process known in the art. For example, it is well known to utilize multiple sieves with differing mesh sizes to separate out different portions of particles from the bulk superabsorbent material 317 having differing particle size diameters. One particular method which can be used in such a classification effort may be ASTM D1921-18, titled "Standard Test Methods for Particle Size (Sieve Analysis) of Plastic Materials".

Figure 10A:
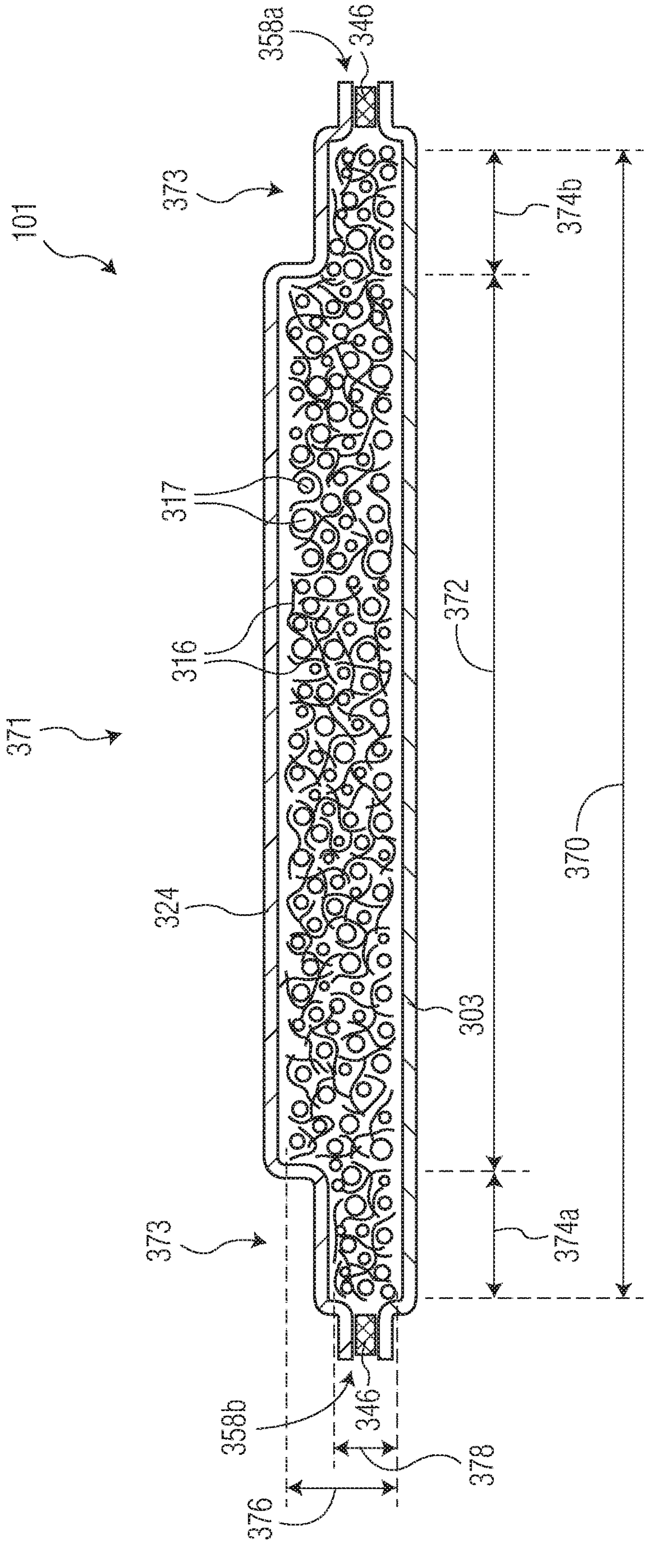
FIG. 10A-10B are different exemplary front cross-sectional views of an absorbent structure formed according to a method of manufacturing according to aspects of the present disclosure, taken along line 10-10 from FIG. 8.
Figure 10B:
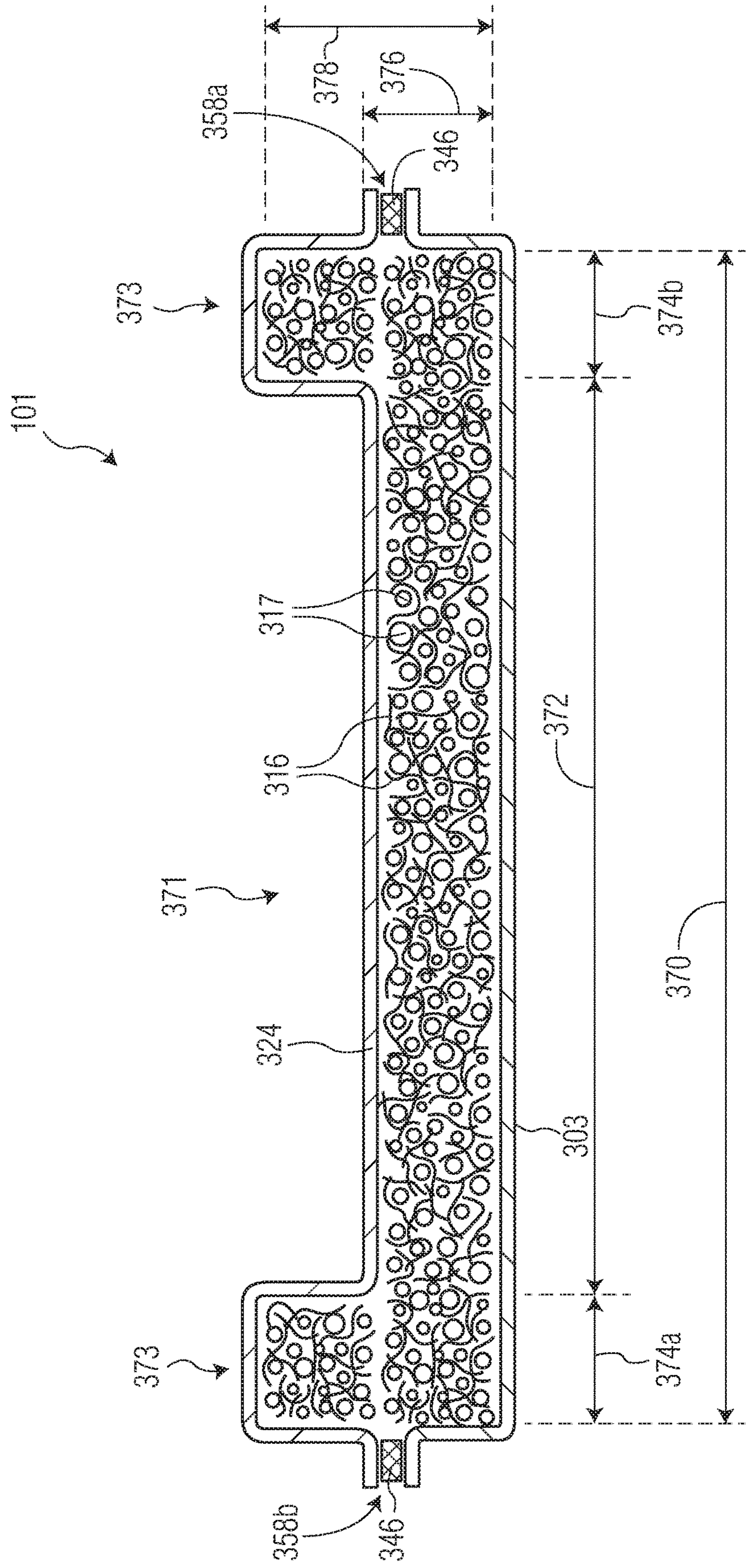

According to further aspects of the present disclosure, another way in which the deposition of the mixture 320 may differ between absorbent material deposition stations 302*a*, 302*b* is that the width of the streams 319, 331 of the superabsorbent material 317, in a direction perpendicular to the machine direction 330, termed the cross-machine direction 338 herein, may be different. For example, one of the streams 319, 331 may be narrower in the cross-machine direction 338 than the other of the streams 319, 331 such that the produced absorbent structures 101 have regions of zoned basis weights of superabsorbent material 317 (and adhesives 308, 310, 334, and/or 336). FIGS. 10A-10B depict different exemplary cross-sections of absorbent structures 101 as taken along line 10-10 in FIG. 8 showing such a zoned mixture 320. Accordingly, the absorbent structures 101 of FIGS. 10A-10B represent different exemplary absorbent structures 101 produced by process 400 where the cross-machine direction widths of the streams 319, 331 of superabsorbent material 317 were different, thus resulting in a varying width of the deposited mixture 320 throughout the structures 101. It should be understood that all of these below described embodiments regarding depositing the mixture 320 at different cross-machine direction widths may be further combined with any of the previously described embodiments where the amount of superabsorbent material 317 and/or the amounts of adhesives 308, 310, 334, and/or 336 differ between each of the absorbent material deposition stations 302*a*, 302*b*.

FIG. 10A depicts an exemplary cross-section of an absorbent structure 101 having an overall width 370, central zone 371 having a central zone width 372, and side zones 373 having side zone widths 374*a*, 374*b*. The central zone width 372 may generally be between 20% and 80% of the overall width 370. In more specific embodiments, the central zone width 372 may be between 25% and 75%, or between 30% and 70%, or between 35% and 65%, or between 40% and 60% of the overall width 370. Accordingly, the side zone widths 374*a*, 374*b*, added together, may generally be between 80% and 20% of the overall width 370, equaling the required percentage of the overall width 370 that, when added to the central zone width 372, equals 100% of the overall width 370. In some embodiments, the side zone widths 374*a*, 374*b* may be equal to each other. Although in other embodiments, the side zone widths 374*a*, 374*b* may differ from each other by between greater than 0% and less than 50% of the side zone width 374*a*, 374*b* having the greater value. As one illustrative example, the overall width 370 may be 100 mm, the central zone width 372 may be 60 mm, and the side zone width 374*a* may be 25 mm while the side zone width 374*b* is 15 mm (e.g. 40% less than the side zone width 374*a*, which has the greater value).

In the embodiment depicted in FIG. 10A, the central zone may have a central zone height 376 while the side zones 373 have a side zone height 378. In the orientation shown in FIG. 10A, the heights 376, 378 may correlate to basis weights of the zones 372, 373, and in particular to basis weights of superabsorbent material 317 (and adhesives 308, 310, 334, and/or 336) within the zones 371, 373. Accordingly, in the embodiment of FIG. 10A, with the central zone height 376 being greater than the side zone heights 378, the central zone 371 may have a greater basis weight of superabsorbent material 317 (and adhesives 308, 310, 334, and/or 336) than the side zones 373. According to some embodiments of the present disclosure, the basis weight of superabsorbent material 317 within the side zones 373 may be between 0% and 75% less than the basis weight of superabsorbent material 317 within the central zone 371. In more specific embodiments, the basis weight of superabsorbent material 317 within the side zones 373 may be between 10% and 70%, or between 10% and 60%, or between 10% and 50%, or between 20% and 60%, or between 30% and 60%, or between 40% and 60% less than the basis weight of superabsorbent material 317 within the central zone 371. As one illustrative example, the central zone 371 may have a basis weight of superabsorbent material 317 of 500 gsm, while the side zones 373 may have basis weights of superabsorbent material 317 of between 150 gsm and 450 gsm (using the example where the basis weight of superabsorbent material 317 within the side zones 373 is between 10% and 70% less than the basis weight of superabsorbent material 317 within the central zone 371).

In order to achieve the above specified differences in basis weights of superabsorbent material 317 within the central zone 371 and the side zones 373, as described previously, the cross-machine direction widths of the streams 319, 331 may differ between the absorbent material deposition stations 302*a*, 302*b*. In some embodiments, the cross-machine direction width of the stream 319 may be less than the cross-machine direction width of the stream 331. In such embodiments, the absorbent material deposition station 302*a*, comprising stream 319, may contribute superabsorbent material 317 substantially only within the central zone 371. Accordingly, in such embodiments, the cross-machine direction width of the stream 331 may be greater than the cross-machine direction width of the stream 319, and the absorbent material deposition station 302*b*, comprising stream 331, may contribute superabsorbent material 317 to both the central zone 371 and the side zones 373. Of course, in other embodiments it may be reversed where the cross-machine direction width of the stream 331 is less than the cross-machine direction width of the stream 319. Such embodiments may produce structures 101 which appear substantially similar to that depicted in FIG. 10A.

FIG. 10B depicts an exemplary cross-section of an absorbent structure 101 having a central zone 371 and side zones 373. In the embodiment of FIG. 10B, in contrast the embodiment of FIG. 10A, the central zone height 376 is less than the side zone height 378. Accordingly, in the embodiment of FIG. 10B, it is the case that the side zones 373 may have basis weight of superabsorbent material 317 that is greater than the basis weight of superabsorbent material 317 within the central zone 371. The difference in basis weights between the central zone 371 and the side zones 373 may be similar to that described with respect to FIG. 10A (for example, the basis weight of the superabsorbent material 317 of the central zone 371 may be between 0% and 75% less than the basis weights of superabsorbent material 317 within the side zones 373).

In order to achieve the above specified differences in basis weights of superabsorbent material 317 within the central zone 371 and the side zones 373, as described previously, the cross-machine direction widths of the streams 319, 331 may differ between the absorbent material deposition stations 302*a*, 302*b*. In some embodiments, the cross-machine direction width of the stream 319 may be less than the cross-machine direction width of the stream 319. In such embodiments, the stream 319 may contribute superabsorbent material 317 substantially only within the central zone 371.

Accordingly, in such embodiments, the cross-machine direction width of the stream 331 may be greater than the cross-machine direction width of the stream 319 and contribute superabsorbent material 317 to both the central zone 371 and the side zones 373. Of course, in other embodiments it may be reversed where the cross-machine direction width of the stream 331 is less than the cross-machine direction width of the stream 319. Such embodiments may produce structures 101 which appear substantially similar to that depicted in FIG. 10A.

In order to achieve the structure depicted in FIG. 10B, one of the streams 319, 331 may have a central region (in the cross-machine direction 338) that is devoid of superabsorbent material 317. In such cases, the one of the streams 319, 331 may comprise two separate, spaced apart sub-streams of superabsorbent material 317. In such embodiments, the absorbent material deposition station 302*a* or 302*b* comprising the one of the streams 319, 331 may contribute superabsorbent material 317 to only the side zones 373, while the other absorbent material deposition station 302*a* or 302*b* contributes superabsorbent material 317 to both of the central zone 371 and the side zones 373. Of course, in different embodiments it could be either of the absorbent material deposition stations 302*a*, 302*b* contributing superabsorbent material 317 to only the side zones 373 of the absorbent structure 101. According to some embodiments, the adhesive applicators 307, 309, 333 and/or 335 of the absorbent material deposition station 302*a*, 302*b* comprising the stream 317 or 331 which is split into two separate, spaced apart sub-streams, may be configured to spray adhesive into the region between the two sub-streams of the stream 319 or 317 such that the adhesives 308, 310, 334, and/or 336 used within the process 400 may generally be present throughout both the central zone 371 and the side zones 373 of the absorbent structure 101. Of course, in other embodiments, the adhesive applicators 307, 309, 333 and/or 335 of the absorbent material deposition station 302*a*, 302*b* comprising the stream 317 or 331 which is split into two separate, spaced apart sub-streams, may be configured to spray adhesive only in the region of the sub-streams of the stream 317 or 331 such that the adhesives 308 and/or 310, or 334 and/or 336 may generally be absent in the central zone 371 of the absorbent structure 101. Still further, it may be the case that the basis weights of the side zones 373 may not be equal to each other. However, in most embodiments the basis weights of the side zones 373 may not differ from each other by more than 50%.

Figure 11A:
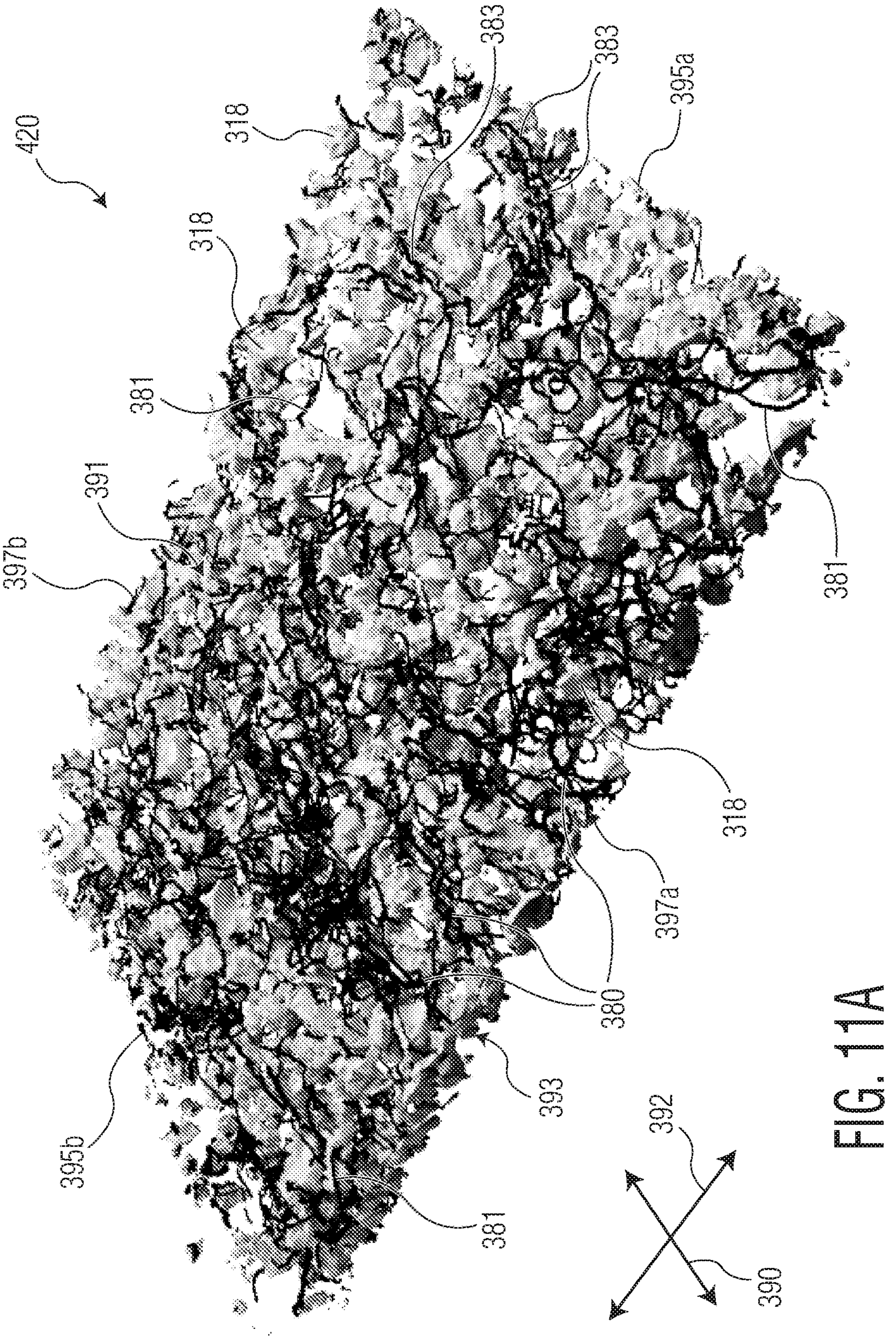
FIG. 11A is a top perspective view of a three-dimensional image generated by a micro-CT process used to analyze an exemplary mixture of particles and adhesive filaments formed by the process of FIG. 8, according to aspects of the present disclosure.

FIG. 11A is a perspective view of a computer-generated image 420 of a deposited mixture 320 which is based on micro-CT images taken from an exemplary deposited mixture 320 formed by the process 300. More specifically, the mixture 320 used to generate the computer generated mixture 420 shown in FIG. 11A was formed by process 300 where the stream 319 and the adhesives 308 and 310 were configured to be same as listed for the first exemplary absorbent structures detailed below, and the resulting structure 320 had superabsorbent material 317 disposed in an amount of 400 gsm and where the adhesives 308, 310, 334, and 336 were present at an add-on rate of 5%. The mixture 320 was stained with osmium tetroxide and then micro-CT scanning was performed, both according to standard, known techniques for staining and scanning. As part of the micro-CT process, a portion of stained deposited mixture 320 chosen approximately from the center of the mixture 320 (e.g. structure 101) in the widthwise and lengthwise directions was chosen for imaging. The portion had dimensions of approximately 3 cm by 1 cm and was sliced into approximately one-thousand two-hundred and fifty individual segments extending in the lateral direction 392, each segment extending from end edge 395*a* to end edge 395*b* and comprising 1986 pixels in the longitudinal dimension (e.g. along longitudinal direction 392). Each segment further comprised 504 pixels in the vertical direction 394 between the first surface 391 and the second surface 393. A voxel size of 8.0 micrometers was used. From the captured segments, a three-dimensional model was generated and is depicted in FIGS. 11A-110.

Figure 11B:
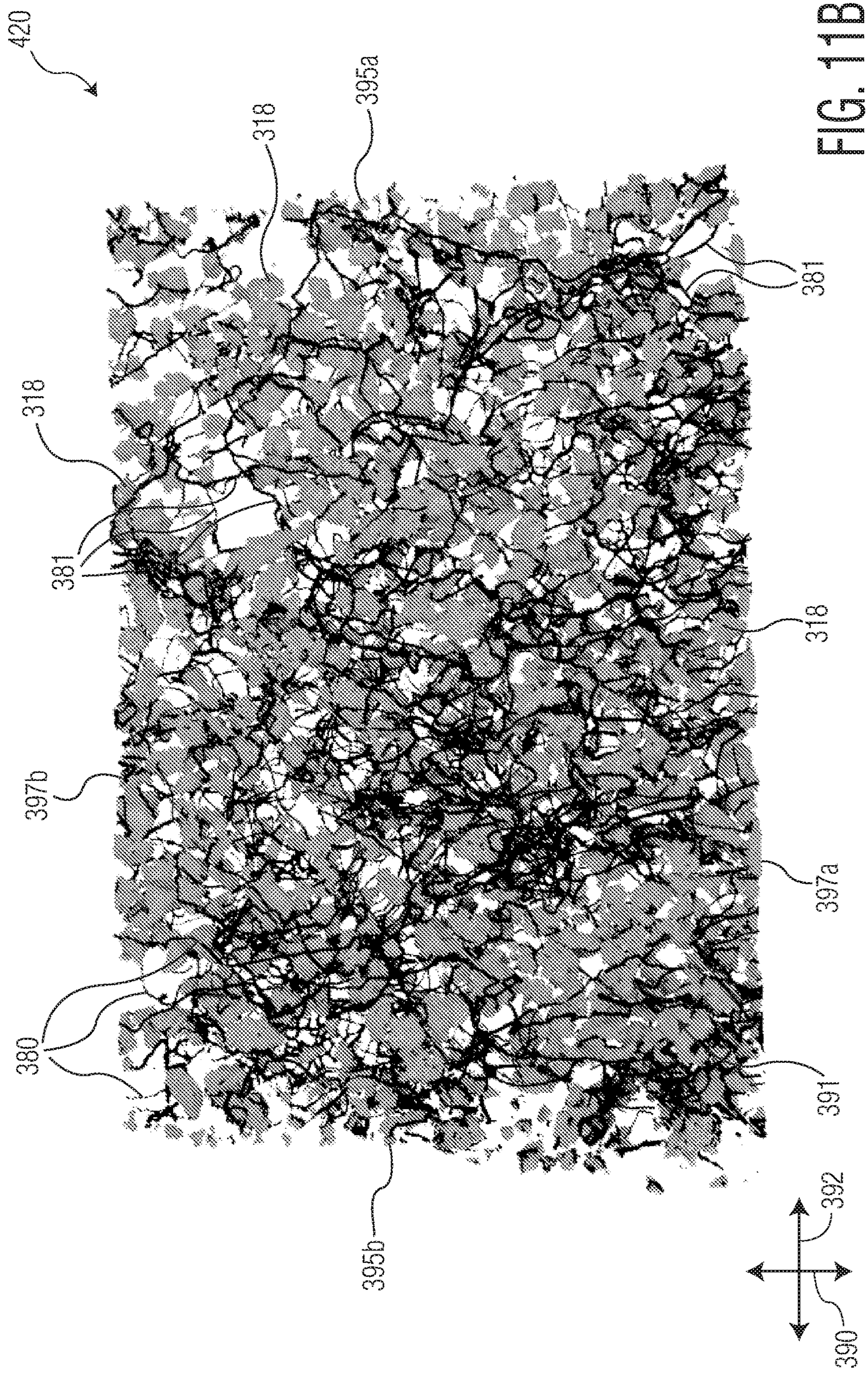
FIG. 11B is a top plan view of the three-dimensional image of FIG. 11A.

The adhesive filaments 316 which were sprayed by the applicators 307, 309, 311 and/or 313 cross and connect as the adhesives 308, 310, 334, and/or 336 and the superabsorbent material 317 intermix to form a three-dimensional mesh network 380 having network adhesive filaments 381 extending substantially throughout the three-dimensional space formed by image 420, as can be seen in FIGS. 11A and 11B. As used herein, the network adhesive filaments 381 may be considered to extend substantially throughout the three-dimensional space formed by the deposited mixture of the image 420 where the network adhesive filaments 381 extend between and intermingle with a majority, or super-majority, of the individual superabsorbent material 317. Such a configuration is in contrast to configurations where adhesive filaments extend over pockets or groupings of superabsorbent particles and do not extend into and between individual superabsorbent material 317 of the pocket or grouping of superabsorbent particles. The superabsorbent material 317 are also disposed throughout the three-dimensional mesh network 380, shown as particles 318, and are immobilized by contact with one or more of the network adhesive filaments 381.

The processes 300 and 400 may operate to intermix the adhesives 308, 310, 334, and/or 336 with the superabsorbent material 317 to such a degree that the network adhesive filaments 381 contact substantially all of the individual superabsorbent material 317. The network adhesive filaments 381 may wrap around a majority, or a super-majority, of the individual superabsorbent material 317. As used herein, the network adhesive filaments 381 may be considered to wrap around an individual superabsorbent particle 318 if combined lengths of individual network adhesive filaments 381 in contact with an individual superabsorbent particle 318 equal at least 40% of a maximum circumference of the individual superabsorbent particle 318.

Figure 11C:
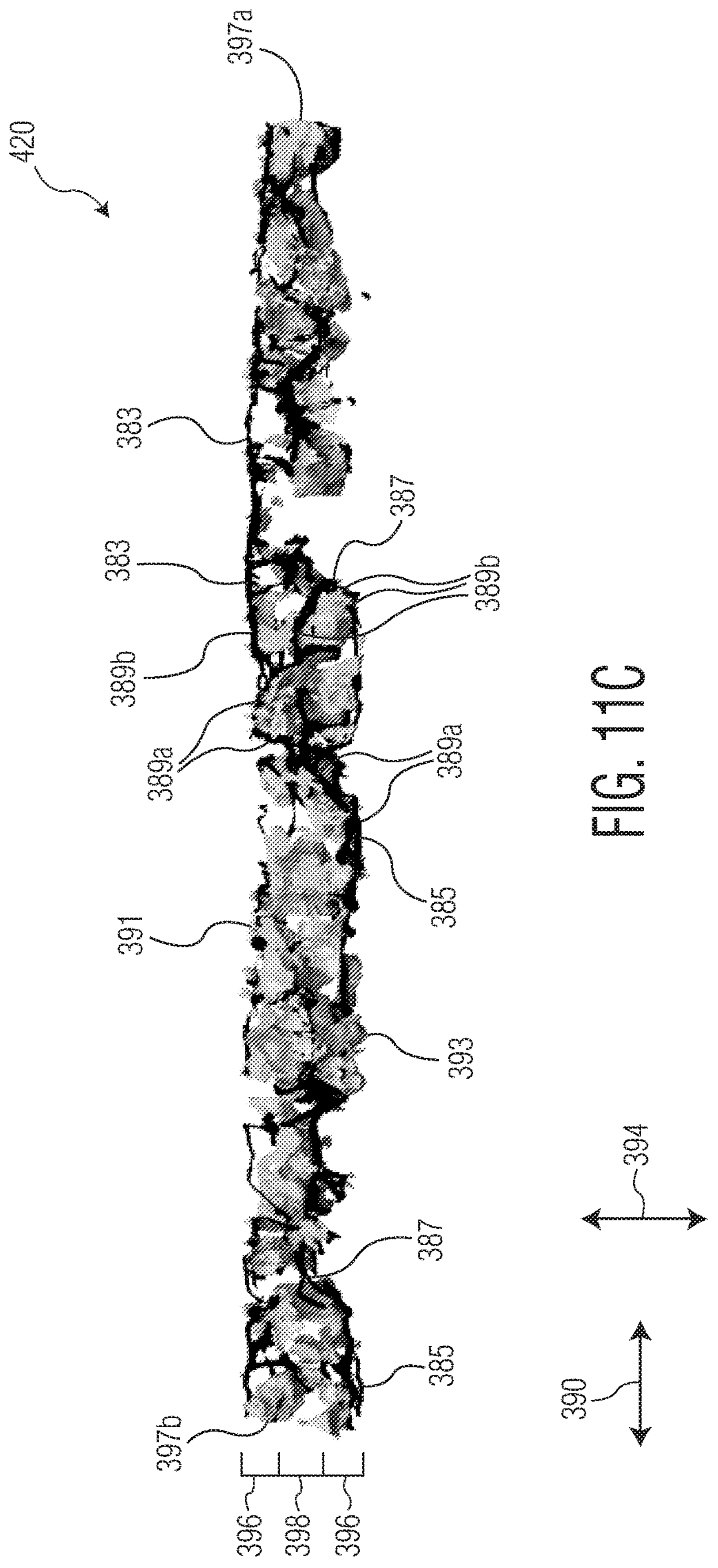
FIG. 11C is a cross-sectional view of a slice of the three-dimensional image of FIG. 11A.

As seen in both FIG. 11A and FIG. 11B, which is a top plan view of a portion of the image 420 of FIG. 11A, along with FIG. 11C, the image 420 of the deposited mixture may generally have a first surface 391 and a second surface 393 disposed opposite the first surface 391, along with end edges 395*a*, 395*b* and side edges 397*a*, 397*b*. Each of the first surface 391 and the second surface 393 extend generally in the lateral and longitudinal directions 390, 392. At each of the first surface 391 and the second surface 393, the mesh network 380 may comprise network adhesive filaments 381 which extend substantially in the lateral and longitudinal directions 390, 392. For example, first network adhesive filaments 383 can be seen extending substantially in the lateral and longitudinal directions 390, 392 along the first surface 391. Second network adhesive filaments 385 (shown in FIG. 11C) may extend substantially in the lateral and longitudinal directions 390, 392 along the second surface 393.

Figure 11D:
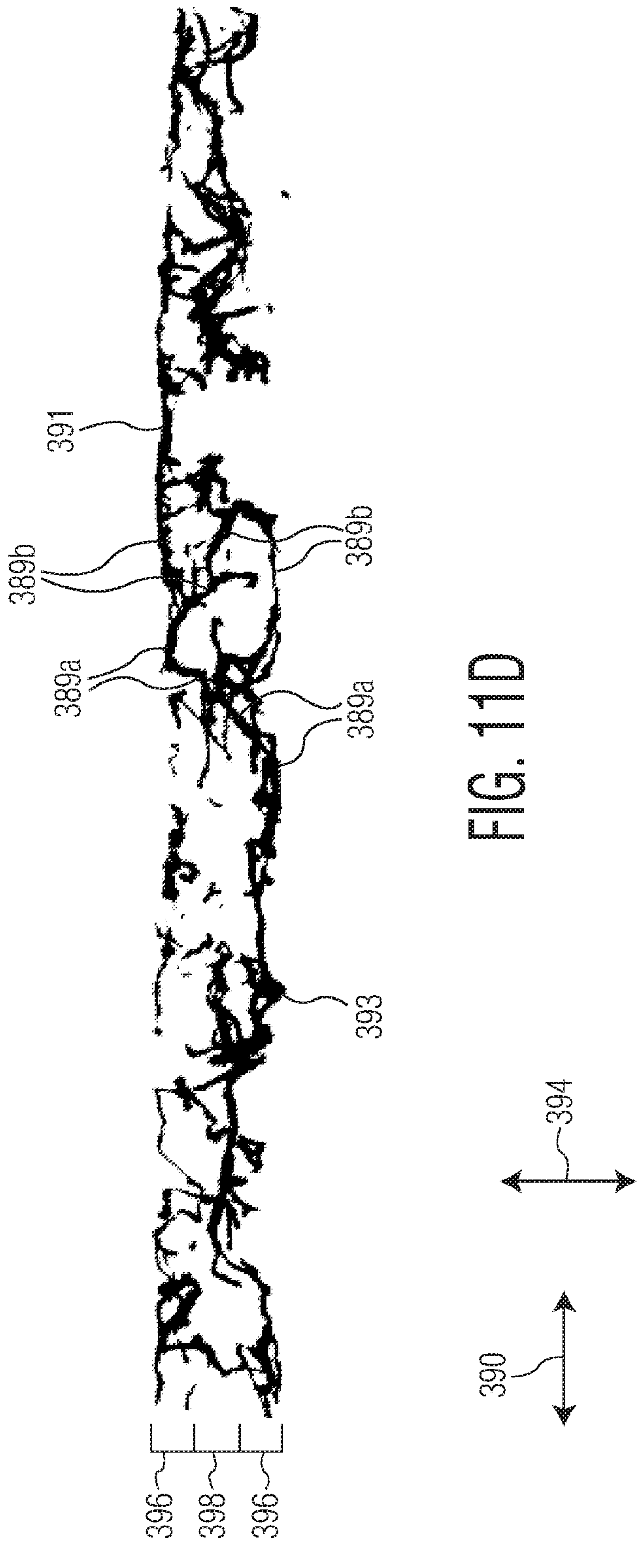
FIG. 11D is the cross-sectional view of FIG. 11C with the particles leaving only the adhesive filaments.

The network adhesive filaments 381 of the three-dimensional mesh network 380 may further include vertically extending filaments 387 which can be seen extending in the vertical direction 394 in FIG. 11C. FIG. 11C represents a laterally extending slice of the image 420 of FIG. 11A and having a length in the longitudinal direction 392 of 0.5 mm, showing in more detail interaction of the particles 318 and adhesive filaments 381. FIG. 11D is the same image as FIG. 11C with the particles 318 removed to show in more detail the adhesive filaments 381 and their disposition through the vertical direction 394.

At least some of these vertically extending filaments 387 extend all the way from the first surface 391 to the second surface 393 and connect the first network adhesive filaments 383 to the second network adhesive filaments 385 to form the three-dimensional mesh network 380. Of course, as can be seen, the vertically extending filaments 387 may not extend perfectly in the vertical direction 394 and may twist and turn between and around individual superabsorbent particles 318 such that at least some of the vertically extending filaments 387 extend also in the lateral and/or longitudinal directions 390, 392. In at least some embodiments, individual network adhesive filaments 381 may themselves extend from along part of the first surface 391 (for example in the longitudinal and/or lateral directions 390, 392), transition to extending in the vertical direction 394, and then connect with the second surface 392—possibly further extending along the longitudinal and/or lateral directions 390, 392 at the second surface 392. Such behavior can be seen with respect to network adhesive filaments 389*a* and 389*b*.

Another feature that can be seen to some extent in the FIGS. 11C-11D is the relative distribution of the network adhesive filaments 381 within different vertical regions of the deposited mixture represented by the image 420. For example, as indicated in FIGS. 11C and 11D, the image 420 may be split into exterior regions 396 and an interior region 398 disposed between the exterior regions 396, spanning the vertical direction 394. The exterior regions 396 may each be defined by a thickness of 33% of the overall thickness of the structure 420, while the interior region 398 may be defined by a thickness of 33% of the overall thickness of the structure 420.

It has been found that the processes 300 and/or 400 may desirably penetrate the adhesives 308, 310, 334, and/or 336 into the interior region 398, thereby promoting high SAM capture values and greater pad uniformity through greater evenness of distribution of the superabsorbent material 317 and adhesives 308, 310, 334, and/or 336 throughout the structure 420. This is particularly true where the formed mixtures 320 of the present disclosure have basis weights of superabsorbent material 317 greater than 300 gsm, or greater than 400 gsm, or greater than 500 gsm, or greater than 600 gsm, or greater than 700 gsm. As the desired basis weights of superabsorbent material 317 in a mixture 320 increases, penetration of the adhesives 308, 310, 334, and/or 336 into an interior of a streams 319 and/or 331 becomes more difficult and where the processes 300 and/or 400 excel in comparison to prior art processes.

In order to assess the ability of the processes 300 and/or 400 to penetrate adhesive into the interior region 398 of the formed mixtures 320, analysis of two sample codes was performed. In the analysis, two sample codes were generated according to process 400 having a basis weight of superabsorbent material of 500 gsm and adhesive disposed in an add-on amount of 5%. From these two sample codes, micro-CT images of portions of the codes were formed—according to the standard processes and techniques mentioned above. The Adhesive Distribution Test Method, described in detail below, was then performed on the generated micro-CT images to determine the relative quantity of adhesive located within the interior region 398 of the imaged portion of the two sample codes. The micro-CT images were generated using the known staining and imaging methods described above.

According to the Adhesive Distribution Test Method, it was found that the first sample code had 28.0% of the of the total amount of adhesive within the first sample code located within the interior region 398 of the first sample code, with the standard deviation being 8.4%. The second sample code was found to have 30.7% of the total amount of adhesive within the second sample code located within the interior region 398 of the second sample code, with the standard deviation being 8.9%. Accordingly, mixtures 320 formed according to the processes 300 and/or 400 can cause greater than 28% of the total amount of adhesive within the mixture 320 to be located within the interior region 398, or greater than 30.5% of the total amount of adhesive within a mixture 320 to be located within the interior region 398. However, in further potential embodiments, it is believed that greater than 33%, or even greater than 35% of the total amount of adhesive within a mixture 320 being located within the interior region 398 of the mixture 320 can be achieved through slight modifications to the processes 300 and/or 400—for example in terms of adhesive add-on amount, vacuum energy, nip pressure, location and angle of the nozzles, and the like. Such high adhesive penetration into the interior region 398 of the formed mixtures of the processes 300 and/or 400 result help to drive improved SAM Capture, Wet Pad Integrity, and Pad Uniformity results, as described in more detail below. The absorbent structures 101 produced by the process 300 and/or 400 have been shown to have beneficial characteristics with respect to prior art absorbent structures. For example, the processes 300 and/or 400 have been shown to produce absorbent structures 101 providing superior performance with respect to the capture and immobilization of superabsorbent material 317, a superior pad integrity of the formed absorbent structures 101, and a greater uniformity in the distribution of the superabsorbent material 317 throughout the formed absorbent structures 101 than prior art structures, as will be described in more detail below.

In order to compare absorbent structures, a number of different absorbent structures 101 were formed by the described processes 300 and/or 400 and tested with respect to absorbent structures formed by prior art processes. As will be described below, exemplary absorbent structures 101 and exemplary prior art absorbent structures were compared with respect to the SAM Capture Test Method, the Wet Pad Integrity Test Method, and the Pad Uniformity Test Method, as described herein below, to produce comparative results.

First Exemplary Absorbent Structures

First exemplary absorbent structures 101, labeled as absorbent structures S23, S27, S53, and S57, as described herein, were formed according to the exemplary process 300. Specifically, first exemplary absorbent structures 101 were formed according to the exemplary process 300 having basis weights of 200 gsm with an adhesive add-on of 3% (labeled as structures S23), having basis weights of 200 gsm with an adhesive add-on of 7% (labeled as structures S27), having basis weights of 500 gsm with an adhesive add-on of 3% (labeled as structures S53), and having basis weights of 500 gsm with an adhesive add-on of 7% (labeled as structures S57).

The settings of the process 300 used to form the exemplary absorbent structures S23, S27, S53, and S57 include using both adhesive applicators 307, 309 with adhesive applicator 307 positioned a distance from the web material 303 and the stream 319 such that the adhesive contacted the stream 319 a distance of 6.4 mm from the web material 303 (e.g. the distance 361). The adhesive applicator 309 was positioned a distance from the web material 303 and the stream 319 such that the adhesive 310 contacted the stream 319 a distance of 16 mm from the web material 303 (e.g. the distance 367 plus the distance 361). Additionally, the chute 315 was positioned a distance 359 of 76 mm from the web material 303. The adhesive nozzle 321 was positioned at an angle 359*a* of 60 degrees with respect to the machine direction 330, and the adhesive nozzle 323 was also positioned at an angle of 60 degrees with respect to the machine direction 330. The nozzles 321 and 232 were Universal™ Signature™ Spray Nozzles available from the Nordson Corporation. The chute width 356 was set at 12 mm, and a nip pressure at nip station 327 was 1 PLI (175.1 N/m). An 8 gsm SMS material was used for material web materials 303 and 324. Vacuum energy was applied such that the forming surface had a pressure differential of approximately 0.51 m of water.

Second Exemplary Absorbent Structures

Second exemplary absorbent structures 101, labeled as absorbent structures D23-D67, as described herein, were formed according to the exemplary process 400. Specifically, second exemplary absorbent structures 101 were formed according to the exemplary process 400 having basis weights of 200 gsm with an adhesive add-on of 3% (labeled as structures D23), having basis weights of 200 gsm with an adhesive add-on of 4% (labeled as structures D24), having basis weights of 200 gsm with an adhesive add-on of 5% (labeled as structures D25), having basis weights of 200 gsm with an adhesive add-on of 6% (labeled as structures D26), and having basis weights of 200 gsm with an adhesive add-on of 7% (labeled as structures D27). Further second exemplary absorbent structures 101 were formed according to the exemplary process 400 having basis weights of 300 gsm with an adhesive add-on of 3% (labeled as structures D33), having basis weights of 300 gsm with an adhesive add-on of 4% (labeled as structures D34), having basis weights of 300 gsm with an adhesive add-on of 5% (labeled as structures D35), having basis weights of 300 gsm with an adhesive add-on of 6% (labeled as structures D36), and having basis weights of 300 gsm with an adhesive add-on of 7% (labeled as structures D37). Still more second exemplary absorbent structures 101 were formed according to the exemplary process 400 having basis weights of 400 gsm with an adhesive add-on of 3% (labeled as structures D43), having basis weights of 400 gsm with an adhesive add-on of 4% (labeled as structures D44), having basis weights of 400 gsm with an adhesive add-on of 5% (labeled as structures D45), having basis weights of 400 gsm with an adhesive add-on of 6% (labeled as structures D46), and having basis weights of 400 gsm with an adhesive add-on of 7% (labeled as structures D47). Even more second exemplary absorbent structures 101 were formed according to the exemplary process 400 having basis weights of 500 gsm with an adhesive add-on of 3% (labeled as structures D53), having basis weights of 500 gsm with an adhesive add-on of 4% (labeled as structures D54), having basis weights of 500 gsm with an adhesive add-on of 5% (labeled as structures D55), having basis weights of 500 gsm with an adhesive add-on of 6% (labeled as structures D56), and having basis weights of 500 gsm with an adhesive add-on of 7% (labeled as structures D57). Further second exemplary absorbent structures 101 were formed according to the exemplary process 400 having basis weights of 600 gsm with an adhesive add-on of 2% (labeled as structures D62), having basis weights of 600 gsm with an adhesive add-on of 3% (labeled as structures D63), having basis weights of 600 gsm with an adhesive add-on of 4% (labeled as structures D64), having basis weights of 600 gsm with an adhesive add-on of 5% (labeled as structures D65), having basis weights of 600 gsm with an adhesive add-on of 6% (labeled as structures D66), and having basis weights of 600 gsm with an adhesive add-on of 7% (labeled as structures D67).

The settings of the process 400 used to form the exemplary absorbent structures D23-D27, D33-D37, D43-D47, D53-D57, and D62-D67 included using both adhesive applicators 307, 309 within absorbent material deposition stations 302*a*. The adhesive applicator 307 was positioned a distance from the web material 303 and the stream 319 such that the adhesive contacted the stream 319 a distance of 6.4 mm from the web material 303 (e.g. the distance 361). The adhesive applicator 309 was positioned a distance from the web material 303 and the stream 319 such that the adhesive 310 contacted the stream 319 a distance of 16 mm from the web material 303 (e.g. the distance 367 plus the distance 361). Additionally, the chute 315 was positioned a distance 359 of 76 mm from the web material 303. The adhesive nozzle 321 was positioned at an angle 359*a* of 60 degrees with respect to the machine direction 330, and the adhesive nozzle 323 was also positioned at an angle of 60 degrees with respect to the machine direction 330. The chute width 356 was set at 12 mm, and a nip pressure at nip station 327 was 1 PLI (175.1 N/m). The settings for absorbent material deposition station 302*b* were substantially the same as above for absorbent material deposition station 302*a*. An 8 gsm SMS material was used for material web materials 303 and 324, and vacuum energy was applied such that the forming surface had a pressure differential of approximately 0.51 m of water.

Third Exemplary Absorbent Structures

Third exemplary absorbent structures 101, labeled as absorbent structures N23-N67 (or, more specifically absorbent structures N23-N27, N33-N37, N43-N47, N53-N57, and N62-N67), as described herein, were formed according to an exemplary prior art process according to prior art document U.S. Pat. No. 8,986,474 to Kufner et al., and assigned to Nordson Corporation (hereinafter "Nordson", or the "Nordson process", or the "Nordson reference"). The exemplary absorbent structures N23-N67 were formed according to the Nordson process according to FIG. 3 of U.S. Pat. No. 8,986,474, where a single absorbent material deposition station was employed with two adhesive dispensing units. Such dispensing units, for example as depicted as units 22, 72 of FIG. 3 of the Nordson reference, were configured such that the discharged adhesive streams 26, 76 converged at the powder mixture 56 and each were oriented at angles of 45 degrees. The adhesive streams 26, 76 both contacted that power mixture 56 a distance 12.7 mm from the web facing material. A chute similar to chute 315 was used and was placed 76 mm away from the web facing material and was set to have a width (e.g. similar to width 356 of the chute 315 of the present disclosure) of 12 mm. Although not necessarily disclosed in the Nordson reference, the absorbent structures formed according to the Nordson process were subjected to the same post processing as described with respect to processes 300 and 400, namely passing through a nip station such as nip station 327 at a setting of 1 PLI (175.1 N/m) and then being cut into individual absorbent structures 101. Vacuum energy was applied such that the forming surface had a pressure differential of approximately 0.51 m of water. As with the first and second exemplary absorbent structures, an 8 gsm SMS material was used for material web materials 303 and 324.

With the prior art Nordson process set up as described above, a number of absorbent structures were produced. Specifically, third absorbent structures 101 having basis weights of 200 gsm with an adhesive add-on of 3% (labeled as structures N23), having basis weights of 200 gsm with an adhesive add-on of 4% (labeled as structures N24), having basis weights of 200 gsm with an adhesive add-on of 5% (labeled as structures N25), having basis weights of 200 gsm with an adhesive add-on of 6% (labeled as structures N26), and having basis weights of 200 gsm with an adhesive add-on of 7% (labeled as structures N27) were produced. Further third exemplary absorbent structures were formed according to the exemplary Nordson process having basis weights of 300 gsm with an adhesive add-on of 3% (labeled as structures N33), having basis weights of 300 gsm with an adhesive add-on of 4% (labeled as structures N34), having basis weights of 300 gsm with an adhesive add-on of 5% (labeled as structures N35), having basis weights of 300 gsm with an adhesive add-on of 6% (labeled as structures N36), and having basis weights of 300 gsm with an adhesive add-on of 7% (labeled as structures N37). Still more third exemplary absorbent structures were formed according to the Nordson process having basis weights of 400 gsm with an adhesive add-on of 3% (labeled as structures N43), having basis weights of 400 gsm with an adhesive add-on of 4% (labeled as structures N44), having basis weights of 400 gsm with an adhesive add-on of 5% (labeled as structures N45), having basis weights of 400 gsm with an adhesive add-on of 6% (labeled as structures N46), and having basis weights of 400 gsm with an adhesive add-on of 7% (labeled as structures N47). Even more third exemplary absorbent structures were formed according to the Nordson process having basis weights of 500 gsm with an adhesive add-on of 3% (labeled as structures N53), having basis weights of 500 gsm with an adhesive add-on of 4% (labeled as structures N54), having basis weights of 500 gsm with an adhesive add-on of 5% (labeled as structures N55), having basis weights of 500 gsm with an adhesive add-on of 6% (labeled as structures N56), and having basis weights of 500 gsm with an adhesive add-on of 7% (labeled as structures N57). Further third exemplary absorbent structures 101 were formed having basis weights of 600 gsm with an adhesive add-on of 2% (labeled as structures N62), having basis weights of 600 gsm with an adhesive add-on of 3% (labeled as structures N63), having basis weights of 600 gsm with an adhesive add-on of 4% (labeled as structures N64), having basis weights of 600 gsm with an adhesive add-on of 5% (labeled as structures N65), having basis weights of 600 gsm with an adhesive add-on of 6% (labeled as structures N66), and having basis weights of 600 gsm with an adhesive add-on of 7% (labeled as structures N67).

SAM Capture Test Method Results

The absorbent structures 101, labeled as absorbent structures S23, S27, S53, and S57, absorbent structures D23-D27, D33-D37, D43-D47, D53-D57, and D62-D67, and absorbent structures N23-N27, N33-N37, N43-N47, N53-N57, and N62-N67 below, were all tested according to the SAM Capture Test Method described in more detail below. Five samples were tested for each code and the averaged results for each code are displayed below in Tables 1A-1L.

The SAM gsm and the % Adh columns indicate the process settings used to form the corresponding structures. For example, the SAM gsm column indicates that the process was set up to produce absorbent structures 101 having an average basis weight of superabsorbent particles 17 of 200 gsm. The % Adh column indicates that the process was set up to produce absorbent structures 101 having a combined average basis weight of the one or more adhesives used of the specified percent, by weight, of the weight of the superabsorbent particles 17 of the structure 101. As one specific example, where the SAM gsm column indicates 200 gsm and the % Adh column indicates 3%, the specified absorbent structure 101 was formed to have a basis weight of adhesive(s) that is 3% of the 200 gsm of superabsorbent particles 17—6 gsm—disposed throughout the structure 101. The Avg % SAM capture value is a measure of the percentage of superabsorbent material 317 retained by the specified absorbent structure 101 at the end of the SAM Capture Test Method.

TABLE 1A

| Code | SAM gsm | % Adh | Avg Pre-Wt (g) | Avg Post-Wt (g) | Avg SAM Loss (g) | Avg % SAM Capture |
|---|---|---|---|---|---|---|
| S23 | 200 | 3 | 8.41 | 6.87 | 1.54 | 82.0% |
| S27 | 200 | 7 | 8.82 | 8.40 | 0.42 | 95.2% |

TABLE 1B

| Code | SAM gsm | % Adh | Avg Pre-Wt (g) | Avg Post-Wt (g) | Avg SAM Loss (g) | Avg % SAM Capture |
|---|---|---|---|---|---|---|
| S53 | 500 | 3 | 18.4 | 8.78 | 9.61 | 47.7% |
| S57 | 500 | 7 | 19.5 | 15.6 | 3.9 | 80.0% |

TABLE 1C

| Code | SAM gsm | % Adh | Avg Pre-Wt (g) | Avg Post-Wt (g) | Avg SAM Loss (g) | Avg % SAM Capture |
|---|---|---|---|---|---|---|
| D23 | 200 | 3 | 8.69 | 8.68 | .01 | 99.9% |
| D24 | 200 | 4 | 8.76 | 8.76 | 0 | 100.0% |
| D25 | 200 | 5 | 8.64 | 8.64 | 0 | 100.0% |
| D26 | 200 | 6 | 8.88 | 8.88 | 0 | 100.0% |
| D27 | 200 | 7 | 8.79 | 8.79 | 0 | 100.0% |

TABLE 1D

| Code | SAM gsm | % Adh | Avg Pre-Wt (g) | Avg Post-Wt (g) | Avg SAM Loss (g) | Avg % SAM Capture |
|---|---|---|---|---|---|---|
| N23 | 200 | 3 | 8.64 | 8.64 | 0 | 100.0% |
| N24 | 200 | 4 | 8.63 | 8.63 | 0 | 100.0% |
| N25 | 200 | 5 | 8.72 | 8.70 | 0.02 | 99.8% |
| N26 | 200 | 6 | 8.61 | 8.60 | 0.01 | 99.9% |
| N27 | 200 | 7 | 8.83 | 8.82 | 0.01 | 99.9% |

TABLE 1E

| Code | SAM gsm | % Adh | Avg Pre-Wt (g) | Avg Post-Wt (g) | Avg SAM Loss (g) | Avg % SAM Capture |
|---|---|---|---|---|---|---|
| D33 | 300 | 3 | 12.31 | 12.30 | 0.01 | 99.9% |
| D34 | 300 | 4 | 12.50 | 12.43 | 0.07 | 99.6% |
| D35 | 300 | 5 | 12.56 | 12.55 | 0.01 | 99.9% |
| D36 | 300 | 6 | 12.80 | 12.78 | 0.02 | 99.9% |
| D37 | 300 | 7 | 12.85 | 12.85 | 0 | 100.0% |

TABLE 1F

| Code | SAM gsm | % Adh | Avg Pre-Wt (g) | Avg Post-Wt (g) | Avg SAM Loss (g) | Avg % SAM Capture |
|---|---|---|---|---|---|---|
| N33 | 300 | 3 | 11.77 | 11.66 | 0.11 | 99.1% |
| N34 | 300 | 4 | 12.03 | 11.91 | 0.12 | 99.0% |
| N35 | 300 | 5 | 12.28 | 12.22 | 0.06 | 99.5% |
| N36 | 300 | 6 | 12.52 | 12.46 | 0.06 | 99.5% |
| N37 | 300 | 7 | 12.68 | 12.61 | 0.07 | 99.4% |

TABLE 1G

| Code | SAM gsm | % Adh | Avg Pre-Wt (g) | Avg Post-Wt (g) | Avg SAM Loss (g) | Avg % SAM Capture |
|---|---|---|---|---|---|---|
| D43 | 400 | 3 | 16.1 | 15.86 | 0.24 | 98.5% |
| D44 | 400 | 4 | 16.24 | 16.12 | 0.12 | 99.3% |
| D45 | 400 | 5 | 16.61 | 16.57 | 0.04 | 99.8% |
| D46 | 400 | 6 | 16.77 | 16.73 | 0.04 | 99.7% |
| D47 | 400 | 7 | 17.13 | 17.08 | 0.05 | 99.7% |

TABLE 1H

| Code | SAM gsm | % Adh | Avg Pre-Wt (g) | Avg Post-Wt (g) | Avg SAM Loss (g) | Avg % SAM Capture |
|---|---|---|---|---|---|---|
| N43 | 400 | 3 | 15.80 | 15.29 | 0.51 | 96.8% |
| N44 | 400 | 4 | 16.16 | 15.72 | 0.44 | 97.3% |
| N45 | 400 | 5 | 16.26 | 15.91 | 0.35 | 97.9% |
| N46 | 400 | 6 | 16.50 | 16.28 | 0.22 | 98.7% |
| N47 | 400 | 7 | 16.67 | 16.48 | 0.19 | 98.8% |

TABLE 1I

| Code | SAM gsm | % Adh | Avg Pre-Wt (g) | Avg Post-Wt (g) | Avg SAM Loss (g) | Avg % SAM Capture |
|---|---|---|---|---|---|---|
| D53 | 500 | 3 | 19.75 | 19.19 | 0.56 | 97.2% |
| D54 | 500 | 4 | 19.50 | 19.37 | 0.13 | 99.3% |
| D55 | 500 | 5 | 19.69 | 19.60 | 0.09 | 99.5% |
| D56 | 500 | 6 | 19.56 | 19.51 | 0.05 | 99.8% |
| D57 | 500 | 7 | 19.81 | 19.78 | 0.03 | 99.8% |

TABLE 1J

| Code | SAM gsm | % Adh | Avg Pre-Wt (g) | Avg Post-Wt (g) | Avg SAM Loss (g) | Avg % SAM Capture |
|---|---|---|---|---|---|---|
| N53 | 500 | 3 | 19.48 | 18.07 | 1.41 | 92.8% |
| N54 | 500 | 4 | 19.57 | 18.55 | 1.02 | 94.8% |
| N55 | 500 | 5 | 19.94 | 19.18 | 0.76 | 96.2% |
| N56 | 500 | 6 | 19.98 | 19.33 | 0.65 | 96.7% |
| N57 | 500 | 7 | 20.42 | 19.67 | 0.75 | 96.3% |

TABLE 1K

| Code | SAM gsm | % Adh | Avg Pre-Wt (g) | Avg Post-Wt (g) | Avg SAM Loss (g) | Avg % SAM Capture |
|---|---|---|---|---|---|---|
| D62 | 600 | 2 | 23.50 | 22.42 | 1.08 | 95.4% |
| D63 | 600 | 3 | 23.83 | 22.78 | 1.05 | 95.6% |
| D64 | 600 | 4 | 23.80 | 23.39 | 0.41 | 98.3% |
| D65 | 600 | 5 | 24.01 | 23.57 | 0.44 | 98.1% |
| D66 | 600 | 6 | 23.97 | 23.71 | 0.26 | 98.9% |
| D67 | 600 | 7 | 24.04 | 23.88 | 0.16 | 99.3% |

TABLE 1L

| Code | SAM gsm | % Adh | Avg Pre-Wt (g) | Avg Post-Wt (g) | Avg SAM Loss (g) | Avg % SAM Capture |
|---|---|---|---|---|---|---|
| N62 | 600 | 2 | 23.53 | 18.21 | 5.32 | 77.4% |
| N63 | 600 | 3 | 23.98 | 21.12 | 2.86 | 88.1% |
| N64 | 600 | 4 | 24.37 | 21.63 | 2.74 | 88.8% |
| N65 | 600 | 5 | 23.90 | 20.79 | 3.11 | 87.0% |
| N66 | 600 | 6 | 24.26 | 20.78 | 3.48 | 85.6% |
| N67 | 600 | 7 | 23.85 | 21.29 | 2.56 | 89.3% |

Accordingly, there are clear differences in the performance of some of the codes formed according to aspects of the present disclosure and codes produced by the Nordson process, particularly codes with relatively lower % Adh values. Specifically, it can be seen that absorbent structures 101 produced according to aspects of the present disclosure which have basis weights of superabsorbent particles 17 of between 400 gsm and 600 gsm and % Adh values of between 4% and 5%, have % SAM Capture Values of greater than 98.0, which is higher than any of the codes of absorbent structures produced by the Nordson process (code N45, falling within the specified ranges for SAM gsm and % Adh, has the highest % SAM Capture Value at 97.9). Alternatively, the structures 101 formed according to aspects of the present disclosure which have basis weights of superabsorbent particles 17 of between 400 gsm and 600 gsm and % Adh values of between 4% and 5% can be described as having % SAM Capture Values of greater than 98.5.

Further, many of the codes produced according to aspects of the present disclosure have % SAM Capture Values greater than 98.0, such as codes D65 (% SAM Capture Value of 98.1), D64 (% SAM Capture Value of 98.3), D55 (% SAM Capture Value of 99.5), D54 (% SAM Capture Value of 99.3), D45 (% SAM Capture Value of 99.8), and D44 (% SAM Capture Value of 99.3). Many of the corresponding codes of absorbent structures produced according to the Nordson process (e.g. codes having corresponding SAM gsm and % Adh values) have much lower % SAM Capture Values—for example, N65 has a % SAM Capture Value of 87.0, N64 has a % SAM Capture Value of 88.8, and N44 has a % SAM Capture Value of 97.3.

With further emphasis on the codes having basis weights of between 500 gsm and 600 gsm, having % Adh values of between 4% and 5%, the absorbent structures 101 formed according to aspects of the present disclosure all have % SAM Capture Values greater than 96.5. For instance, the codes D54, D55, D64, and D65 have % SAM Capture Values of 99.3, 99.5, 98.3, and 98.1, respectively. The corresponding codes N54, N55, N64, and N65 have % SAM Capture Values of 94.8, 96.2, 88.8, and 87.0, respectively.

Advantages in performance of codes of structures 101 formed according to aspects of the present disclosure in comparison to codes of absorbent structures produced by the Nordson process may also be evident where the basis weights of superabsorbent particles 17 are between 500 gsm and 600 gsm and the % Adh values are between 3% and 4%. In such examples, the structures 101 produced according to aspects of the present disclosure all have % SAM Capture Values of greater than 95.0, which is higher than any of the codes of absorbent structures produced by the Nordson process (code N54, falling within the specified ranges for SAM gsm and % Adh, has the highest % SAM Capture Value at 94.8).

Further, many of the codes produced according to aspects of the present disclosure have % SAM Capture Values greater than 95.0, such as codes D53 (% SAM Capture Value of 97.2), D54 (% SAM Capture Value of 99.3), D63 (% SAM Capture Value of 95.6), and D64 (% SAM Capture Value of 98.3). Many of the corresponding codes of absorbent structures produced according to the Nordson process have much lower % SAM Capture Values—for example, N53 has a % SAM Capture Value of 92.8, N63 has a % SAM Capture Value of 88.1, and N64 has a % SAM Capture Value of 88.8.

Where the % Adh value is increased to be between 4% and 5%, the structures 101 produced according to aspects of the present disclosure having basis weights of superabsorbent particles 17 of between 500 gsm and 600 gsm, still outperform the absorbent structures produced by the Nordson process by all having % SAM Capture Values of at greater than 97.0. For example, codes D54, D55, D64, and D65 have % SAM Capture Values of 99.3, 99.5, 98.3, and 98.1, respectively. The corresponding absorbent structures produced by the Nordson process, codes N54, N55, N64, and N65 have % SAM Capture Values of 94.8, 96.2, 88.8, and 87.0, respectively.

Even where the % Adh value is increased to be between 5% and 6%, the structures 101 produced according to aspects of the present disclosure, and having basis weights of superabsorbent particles 17 of between 500 gsm and 600 gsm, still outperform the absorbent structures produced by the Nordson process by all having % SAM Capture Values of at greater than 97.0. For example, codes D55, D56, D65, and D66 have % SAM Capture Values of 99.5, 99.8, 98.1, and 98.9, respectively. The corresponding absorbent structures produced by the Nordson process, codes N55, N56, N65, and N66 have % SAM Capture Values of 96.2, 96.7, 87.0, and 85.6, respectively.

Wet Pad Integrity Test Method Results

In obtaining comparative measurements of absorbent structures 101 formed according to aspects of the present disclosure and absorbent structures formed according to the Nordson process, a number of different codes were produced. As shown in the TABLE 2A below, absorbent structures 101 formed according to aspects of the present disclosure, labeled as codes DD23, DD27, DD53, and DD57 were produced. The codes DD23, DD27, DD53, and DD57 were formed by a process similar to that described above with respect to the Second Exemplary Absorbent Structures. Additionally, corresponding absorbent structures were formed according to the Nordson process, shown in TABLE 2B and labeled as NN23, NN27, NN53, and NN57. The codes NN23, NN27, NN53, and NN57 were formed by a process similar to that described above with respect to the Third Exemplary Absorbent Structures. Five of each of these codes were tested according to the Wet Pad Integrity Test Method described in more detail below, and the results are shown in TABLES 2A and 2B below. The Avg # column details the average number of shakes (average of the five samples tested) imparted to the structures during Wet Pad Integrity Test Method for which the structures maintained their integrity, capped at 50 shakes.

TABLE 2A

| Code | SAM gsm | % Adh | Avg # |
|---|---|---|---|
| DD23 | 200 | 3 | 20 |
| DD27 | 200 | 7 | 50 |
| DD53 | 500 | 3 | 3 |
| DD57 | 500 | 7 | 38 |

TABLE 2B

| Code | SAM gsm | % Adh | Avg # |
|---|---|---|---|
| NN23 | 200 | 3 | 19 |
| NN27 | 200 | 7 | 50 |
| NN53 | 500 | 3 | 0 |
| NN57 | 500 | 7 | 18 |

As can be seen in TABLES 2A and 2B, there are clear benefits in terms of Wet Pad Integrity to the absorbent structures 101 formed according to aspects of the present disclosure in comparison to the absorbent structures formed according to the Nordson process. For example, the code DD57, representing an absorbent structure 101 formed to have an average basis weight of superabsorbent material 317 of 500 gsm and a combined basis weight of one or more adhesives of 7% of the basis weight of the superabsorbent material 317, had a Wet Pad Integrity value of 38, which is 110% higher than the Wet Pad Integrity value for the corresponding code NN57 formed according to the Nordson process (Wet Pad Integrity value for NN57 is 18). In other embodiments, the absorbent structures 101 formed according to aspects of the present disclosure may be described as having Wet Pad Integrity Values of at least 25, or at least 30, or at least 35, when such absorbent structures 101 are formed to have an average basis weight of superabsorbent material 317 of 500 gsm and a combined basis weight of one or more adhesives of 7% of the basis weight of the superabsorbent material 317. As another example, the code DD53, representing an absorbent structure 101 formed to have an average basis weight of superabsorbent material 317 of 500 gsm and a combined basis weight of one or more adhesives of 3% of the basis weight of the superabsorbent material 317, had a Wet Pad Integrity value of 3, which higher than the Wet Pad Integrity value for the corresponding code NN53 (Wet Pad Integrity value for NN53 is 0) formed according to the Nordson process which could not withstand even a single shake from the Wet Pad Integrity Test Method.

In this manner, it can be seen that the processes 300 and 400 produce absorbent structures 101 having a superior Wet Pad Integrity than absorbent structures produced by prior art processes. For example, the processes disclosed herein include gravity feeding superabsorbent material 317 forming a stream of superabsorbent toward a web material 303 and further include spraying both a first side and a second side of the stream with adhesive. As described herein, the adhesive intermixes with the superabsorbent material 317 prior to deposition onto the web material 303. Accordingly, based on the above results, these processes are additionally capable of producing absorbent structures 101 having Wet Pad Integrity values greater than or equal to 20, according to the Wet Pad Integrity Test, at least when used to produce structures 101 which have superabsorbent material 317 disposed in an amount equal to 500 gsm and adhesive disposed in an amount equal to 7% by weight, of the weight of the superabsorbent material 317. Of course, as described in more detail with respect to process 400, it could be the case that the process includes gravity feeding two separate streams of superabsorbent material 317 toward web material 303 and spraying adhesive at first and second sides of both streams of superabsorbent material 317. Further, such processes according to the present disclosure may be described as being able to form absorbent structures 101 having Wet Pad Integrity Values of at least 25, or at least 30, or at least 35, when such absorbent structures 101 are formed to have an average basis weight of superabsorbent material 317 of 500 gsm and a combined basis weight of one or more adhesives of 7% of the basis weight of the superabsorbent material 317. Additionally, such processes according to the present disclosure are able to form absorbent structures 101 having Wet Pad Integrity Values of at least 1, or at least 2, or at least 3, when such absorbent structures 101 are formed to have an average basis weight of superabsorbent material 317 of 500 gsm and a combined basis weight of one or more adhesives of 3% of the basis weight of the superabsorbent material 317

Pad Uniformity Test Method Results

Another feature of the processes described herein, as compared to the Nordson process, is that the processes described herein are able to produce absorbent structures 101 which have a more uniform distribution of superabsorbent material 317 and adhesive fibers 316 throughout the formed structures 101 than absorbent structures formed according to the Nordson process. This higher uniformity can allow the absorbent structures 101 to be thinner, more flexible, and handle fluid better than absorbent structures having similar basis weights of superabsorbent material and adhesive.

In order to compare the distribution of superabsorbent material 317 and adhesive fibers 316, a number of different absorbent structures 101 were formed according to aspects of the present disclosure and compared to a number of different absorbent structures formed according to the Nordson process. As can be seen in TABLES 3A-3E, absorbent structures 101 formed according to aspects of the present disclosure are labeled as codes DDD23, DDD24, DDD27, DDD33, DDD34, DDD44, DDD45, DDD56, DDD62, DDD66, and DDD67. These codes were formed by a process similar to that described above with respect to the Second Exemplary Absorbent Structures. The absorbent structures formed according to the Nordson process are labeled as NNN23, NNN24, NNN27, NNN33, NNN34, NNN44, NNN45, NNN56, NNN62, NNN66, and NNN67. These codes were formed by a process similar to that described above with respect to the Third Exemplary Absorbent Structures.

The TABLES 3A-3E reporting the results of the various codes according to the Pad Uniformity Test Method represent the results from a single sample for each code. The CD GL Var. column details the variance in the gray level of the sample over a portion of the sample extending the cross-direction, as determined according to the Pad Uniformity Test Method. Lower gray level variance values indicate a generally more uniform structure, since the variance in the determined gray levels is lower. The CD Mean GL column reports the determined mean gray level value for the sample, as determined according to the Pad Uniformity Test Method, while the GL % COV value reports the calculated gray level variability normalized with respect to the mean gray level. For example, the GL % COV value is determined by dividing the gray level standard deviation by the mean gray level, for a given sample, and multiplying such a calculated value by 100%. Determining all of these values is described in more detail below with respect to the Pad Uniformity Test Method.

TABLE 3A

| Code | SAM gsm | % Adh | CD GL Var. | CD GL Var. Std. Dev. | CD Mean GL | CD Mean GL Std. Dev. | GL % COV | GL % COV Std. Dev. |
|---|---|---|---|---|---|---|---|---|
| DDD23 | 200 | 3 | 650.8 | 73.1 | 108.2 | 3.0 | 24.5 | 1.2 |
| NNN23 | 200 | 3 | 879.3 | 88.3 | 104.4 | 3.1 | 29.1 | 0.9 |
| DDD24 | 200 | 4 | 653.2 | 67.4 | 106.7 | 2.4 | 25.4 | 1.0 |
| NNN24 | 200 | 4 | 834.3 | 117.7 | 103.2 | 3.5 | 28.7 | 0.9 |
| DDD27 | 200 | 7 | 761.6 | 105.6 | 96.3 | 3.3 | 30.0 | 1.1 |
| NNN27 | 200 | 7 | 762.0 | 94.7 | 107.0 | 3.0 | 27.1 | 0.9 |

TABLE 3B

| Code | SAM gsm | % Adh | CD GL Var. | CD GL Var. Std. Dev. | CD Mean GL | CD Mean GL Std. Dev. | GL % COV | GL % COV Std. Dev. |
|---|---|---|---|---|---|---|---|---|
| DDD33 | 300 | 3 | 577.7 | 77.5 | 88.8 | 2.5 | 28.8 | 1.7 |
| NNN33 | 300 | 3 | 677.4 | 100.4 | 98.3 | 3.3 | 27.8 | 1.5 |
| DDD34 | 300 | 4 | 623.5 | 76.9 | 86.0 | 2.4 | 30.7 | 1.5 |
| NNN34 | 300 | 4 | 716.0 | 111.4 | 88.5 | 3.1 | 31.6 | 1.5 |

TABLE 3C

| Code | SAM gsm | % Adh | CD GL Var. | CD GL Var. Std. Dev. | CD Mean GL | CD Mean GL Std. Dev. | GL % COV | GL % COV Std. Dev. |
|---|---|---|---|---|---|---|---|---|
| DDD44 | 400 | 4 | 476.6 | 83.3 | 76.2 | 3.1 | 30.2 | 2.0 |
| NNN44 | 400 | 4 | 592.3 | 98.3 | 72.5 | 2.7 | 34.7 | 2.4 |
| DDD45 | 400 | 5 | 466.4 | 65.2 | 72.8 | 2.4 | 31.1 | 1.8 |
| NNN45 | 400 | 5 | 640.3 | 99.6 | 73.2 | 3.0 | 36.1 | 1.7 |

TABLE 3D

| Code | SAM gsm | % Adh | CD GL Var. | CD GL Var. Std. Dev. | CD Mean GL | CD Mean GL Std. Dev. | GL % COV | GL % COV Std. Dev. |
|---|---|---|---|---|---|---|---|---|
| DDD56 | 500 | 6 | 400.0 | 47.3 | 63.6 | 3.0 | 33.4 | 1.9 |
| NNN56 | 500 | 6 | 513.0 | 101.1 | 61.9 | 3.4 | 38.0 | 2.6 |

TABLE 3E

| Code | SAM gsm | % Adh | CD GL Var. | CD GL Var. Std. Dev. | CD Mean GL | CD Mean GL Std. Dev. | GL % COV | GL % COV Std. Dev. |
|---|---|---|---|---|---|---|---|---|
| DDD62 | 600 | 2 | 356.2 | 64.7 | 68.0 | 2.7 | 29.2 | 2.2 |
| NNN62 | 600 | 2 | 531.6 | 143.4 | 68.2 | 4.0 | 36.1 | 3.9 |
| DDD66 | 600 | 6 | 275.1 | 60.1 | 58.9 | 2.8 | 29.5 | 2.5 |
| NNN66 | 600 | 6 | 498.4 | 71.5 | 62.5 | 2.8 | 37.5 | 2.6 |
| DDD67 | 600 | 7 | 254.2 | 51.9 | 58.0 | 3.2 | 29.1 | 2.8 |
| NNN67 | 600 | 7 | 532.2 | 106.4 | 62.8 | 4.4 | 35.9 | 6.5 |

As can be seen in the TABLES 3A-3E, the structures 101 produced by the processes described herein result in much lower gray level variance than the absorbent structures formed according to the Nordson process. For example, the codes DDD23 and DDD24 have CD GL Var. values of less than 815, less than 800, less than 750, or less than 700, as determined according to the Pad Uniformity Test Method. Such CD GL Var. values are all less than the CD GL Var. values of the corresponding NNN23 and NNN24 codes. Put another way, absorbent structures 101 formed according to aspects of the present disclosure which have superabsorbent material 317 disposed at a basis weight of 200 gsm and one or more adhesives disposed in a combined basis weight that is less than 4%, by weight, of the basis weight of superabsorbent material 317, may have CD GL Var. values of less than 815, less than 800, less than 750, or less than 700, as determined according to the Pad Uniformity Test Method. In some of these embodiments, the one or more adhesives may be disposed in a combined basis weight of between 3% and 4%, by weight, of the basis weight of superabsorbent material 317.

Further examples indicate that codes DDD33 and DDD34 have CD GL Var. values of less than 675, less than 650, or less than 625, as determined according to the Pad Uniformity Test Method. Such CD GL Var. values are all less than the CD GL Var. values of the corresponding NNN33 and NNN34 codes. Put another way, absorbent structures 101 formed according to aspects of the present disclosure which have superabsorbent material 317 disposed at a basis weight of 300 gsm and one or more adhesives disposed in a combined basis weight that is less than 4%, by weight, of the basis weight of superabsorbent material 317, may have CD GL Var. values of less than 675, less than 650, or less than 625, as determined according to the Pad Uniformity Test Method. In some of these embodiments, the one or more adhesives may be disposed in a combined basis weight of between 3% and 4%, by weight, of the basis weight of superabsorbent material 317.

Still further examples indicate that codes DDD44 and DDD45 have CD GL Var. values of less than 575, or less than 550, less than 525, or less than 500, as determined according to the Pad Uniformity Test Method. Such CD GL Var. values are all less than the CD GL Var. values of the corresponding NNN44 and NNN45 codes. Put another way, absorbent structures 101 formed according to aspects of the present disclosure which have superabsorbent material 317 disposed at a basis weight of 400 gsm and one or more adhesives disposed in a combined basis weight that is less than 5%, by weight, of the basis weight of superabsorbent material 317, may have CD GL Var. values of less than 585, less than 550, less than 525, or less than 500, as determined according to the Pad Uniformity Test Method. In some of these embodiments, the one or more adhesives may be disposed in a combined basis weight of between 4% and 5%, by weight, of the basis weight of superabsorbent material 317.

More examples indicate that code DDD56 has a CD GL Var. value of less than 500, or less than 475, less than 450, or less than 425, as determined according to the Pad Uniformity Test Method. Such CD GL Var. values are all less than the CD GL Var. value of the corresponding NNN56 code. Put another way, absorbent structures 101 formed according to aspects of the present disclosure which have superabsorbent material 317 disposed at a basis weight of 500 gsm and one or more adhesives disposed in a combined basis weight that is 6%, by weight, of the basis weight of superabsorbent material 317, may have CD GL Var. values of less than 500, less than 475, less than 450, or less than 425, as determined according to the Pad Uniformity Test Method.

The TABLE 3E highlights that especially at high basis weights of superabsorbent material 317, the absorbent structures 101 formed according to aspects of the present disclosure are superior to the absorbent structures formed according to the Nordson process. Codes DDD62, DDD63, and DDD67 have CD GL Var. values of less than 475, less than 450, less than 425, less than 400, or less than 375, as determined according to the Pad Uniformity Test Method. In particular, the codes DDD66 and DDD67 have CD GL Var. values of less than 350, less than 325, or less than 300. Such CD GL Var. values are all less than the CD GL Var. values of the corresponding NNN62, NNN66, and NNN67 codes. Put another way, absorbent structures 101 formed according to aspects of the present disclosure which have superabsorbent material 317 disposed at a basis weight of 600 gsm and one or more adhesives disposed in a combined basis weight that is less than 7%, by weight, of the basis weight of superabsorbent material 317, may have CD GL Var. values of less than 475, less than 450, less than 425, less than 400, or less than 375, as determined according to the Pad Uniformity Test Method. In some of these embodiments, the one or more adhesives may be disposed in a combined basis weight of between 2% and 7%, by weight, of the basis weight of superabsorbent material 317. In further of these examples, where the basis weights of the one or more adhesives are disposed range between 6% and 7%, by weight, of the basis weight of superabsorbent material 317, such absorbent structures 101 may have CD GL Var. values of less than 350, less than 325, or less than 300.

Additional characterizations of the absorbent structures 101 formed according to aspects of the present disclosure may include the following: absorbent structures 101 having a basis weight of superabsorbent material 317 of between 500 gsm and 600 gsm may have CD GL Var. values of less than 475, less than 450, or less than 425. In at least some of these embodiments, one or more adhesives present in such structures 101 may have a combined basis weight of less than 7%, or less than 6%, or between 6% and 7%, or between 2% and 7%. Absorbent structures 101 having a basis weight of superabsorbent material 317 of between 400 gsm and 500 gsm may have CD GL Var. values of less than 510, less than 500, less than 490, or less than 480. In at least some of these embodiments, one or more adhesives present in such structures 101 may have a combined basis weight of less than 6%, or less than 5%, or between 4% and 6%. Absorbent structures 101 having a basis weight of superabsorbent material 317 of between 300 gsm and 400 gsm may have CD GL Var. values of less than 590 or less than 580. In at least some of these embodiments, one or more adhesives present in such structures 101 may have a combined basis weight of less than 5%, or less than 4%, or between 3% and 5%. Absorbent structures 101 having a basis weight of superabsorbent material 317 of between 200 gsm and 300 gsm, and wherein one or more adhesives present in such structures 101 have a combined basis weight of between 3% and 4%, may have CD GL Var. values of less than 675, less than 665, or less than 655.

When using the GL % COV values, it can be seen that the absorbent structures 101 formed according to aspects of the present disclosure have generally lower variance in the determined gray level across different basis weights. For example, the codes DDD44, DDD45, DDD56, DDD62, DDD66, and DDD67 all have GL % COV values of less than 34.5, less than 34, or less than 33.5. Such GL % COV values are all less than the GL % COV values of the corresponding NNN44, NNN45, NNN56, NNN62, NNN66, and NNN67 codes. Put another way, absorbent structures 101 formed according to aspects of the present disclosure which have superabsorbent material 317 disposed at a basis weight of between 400 gsm and 600 gsm, and one or more adhesives disposed in a combined basis weight that is less than 7%, by weight, of the basis weight of superabsorbent material 317, may have GL % COV values of less than 34.5, less than 34, or less than 33.5, as determined according to the Pad Uniformity Test Method. In some of these embodiments, the one or more adhesives may be disposed in a combined basis weight of between 4% and 7%, or between 4% and 6%, by weight, of the basis weight of superabsorbent material 317. In further of any of these embodiments, the superabsorbent material 317 may be disposed at a basis weight of between 400 gsm and 500 gsm.

As another example, the codes DDD34, DDD44, and DDD45 all have GL % COV values of less than 31.5, or less than 31.3. The lowest GL % COV value of the corresponding NNN34, NNN44, and NNN45 codes is 31.6. Put another way, absorbent structures 101 formed according to aspects of the present disclosure which have superabsorbent material 317 disposed at a basis weight of between 300 gsm and 400 gsm, and one or more adhesives disposed in a combined basis weight that is between 4% and 5%, by weight, of the basis weight of superabsorbent particles 318, may have GL % COV values of less than 31.5, or less than 31.3, as determined according to the Pad Uniformity Test Method.

SAM Capture Test Method

Individual sample absorbent structures are first obtained, whether by deconstruction of a commercially available product or by obtaining individual structures directly from a manufacturing line prior to incorporation into a product. If obtained from a commercially available product, typical product deconstruction methods should be used to obtain only the absorbent structure, such as the use of a freeze spray or other equivalent products which helps to deactivate any adhesive laminating the various layers of the product together, allowing for easier separation of the layers, and/or scissors to cut open one or more portions of the product. If obtained directly from a manufacturing line, the sample absorbent structures should be left to cure for a minimum of 24 hours.

Once the sample absorbent structures are ready, each individual sample should be weighed, and the weights should be recorded. Next, each sample structure is peeled apart, preferably over a garbage can or the like to capture any material fall out. The samples may be peeled apart by grasping one of the outside web materials in each hand, at one end of the structure, and pulling apart in a peeling motion. Once pulled apart, the separated webs are given a slight shake over the garbage can and then placed back on the scale for a second weighing, which is recorded.

A difference in the first recorded weight of a sample and a second recorded weight of the sample represents the amount of superabsorbent material lost. This difference value may then be used to determine a percentage of the total amount of superabsorbent material retained. In the present disclosure, since the web materials, the basis weights of the deposited superabsorbent material, and the adhesive add-on amounts were the same for the compared sample structures, this difference value was simply divided by the first record weight of a sample to arrive at the reported percent of superabsorbent material retained value. However, where comparing un-like samples, the basis weights and sizes of the web materials may be taken into account—for example by subtracting the total weight of the web materials of a sample from the first and second recorded weights. The total weight of the adhesives may be considered as generally negligible to the percentage retained value determination and therefore not accounted for separately.

Wet Pad Integrity Test Method

Individual sample absorbent structures are first obtained, whether by deconstruction of a commercially available product or by obtaining individual structures directly from a manufacturing line prior to incorporation into a product. If obtained from a commercially available product, typical product deconstruction methods should be used to obtain only the absorbent structure, such as the use of a freeze spray or other equivalent products which helps to deactivate any adhesive laminating the various layers of the product together, allowing for easier separation of the layers, and/or scissors to cut open one or more portions of the product. If obtained directly from a manufacturing line, the sample absorbent structures should be left to cure for a minimum of 24 hours.

Once obtained, target locations are marked for each sample. The target locations are marked 8.5 cm toward the front edge of the sample. The front edge of the sample is the edge located closest to the front of a product, if removed from a product, or toward the edge that would be placed closest to the front of a product if the sample was obtained directly from the manufacturing line. The product should then be adhered to a lightbox or other suitable work surface. The sample may be adhered with double side tape or the like positioned at front and/or rear edges of the sample.

Next, a plastic tube, having a length of 152 mm and a diameter of 51 mm (with a wall thickness of 3.5 mm and an internal diameter of 44 mm), is centered at the target location. A plastic funnel is placed at the top of the plastic tube and 100 ml of 0.9% blue colored saline was poured into the funnel. Care should be taken so as to not apply any pressure to the surface of the sample while holding the tube in place. Additionally, the funnel spout should be angled toward a wall of the tube so that the saline flows down the side of the tube before contacting the surface of the sample. Once the fluid has been poured into the funnel, a 5-minute timer is set.

After the 5 minutes, the sample is then hung from a product shaker machine. The product shaker machine consists of a simple frame with linear actuator attached to the top of the frame and oriented in the vertical direction. A 12-inch (305 mm) long horizontal bar is connected directly to the actuator and two product clips are attached to the horizontal bar. The sample absorbent structure front edge is connected to the product shaker machine through the clips. The product shaker is then switched on and the number of shakes counted. The linear actuator is configured to move the 12-inch bar up and down a total linear distance of 1-inch (25.4 mm) per half-stroke (one movement down or one movement up). A full-stroke movement is counted as one shake. Many commercially available linear actuators may be used as part of such a product shaker machine. For example, commercially available 12V or 24V actuators having a 25 mm stroke and around a fifty-pound rating along with actuating on the order of 30 mm per second may be particularly suitable actuators. Any suitable simple drive circuitry can be utilized to operate the linear actuator through extend and retract cycles. While the product shaker is on, the sample is observed for any partial breaks, which constitute any crack or gap appearing in the sample. Once the first partial break is observed, the number of shakes is noted and the product shaker machine turned off. If no partial cracks were observed by fifty shakes, the test is stopped and a value of 50 shakes was recorded for the sample.

Pad Uniformity Test Method

The cross-machine direction (CD) gray-level variation properties of thin, fluffless absorbent fibrous webs, including structures 101 formed according to the methods 300 and 400 according to the present disclosure and including structures formed according to the Nordson process, can be determined using an image analysis method described herein. In this context, CD gray-level variations for thin fluffless absorbent fibrous webs provide an indication of a uniformity of distribution of the adhesives and superabsorbent particles throughout the webs. For instance, webs having a lower CD gray level variation may be considered to have adhesives and superabsorbent particles disposed relatively more uniformity through the webs, because the amount light passing through the webs is relatively more uniform throughout the webs as compared to webs having a relatively higher CD gray level variation, as will be explained in more detail below.

The method for determining the CD gray level variation includes using diffuse, transmitted light which passes through the web and is detected by a camera. The camera may specifically be a CCD camera such as a Leica Microsystems DFC 310 camera available from Leica Microsystems of Heerbrugg, Switzerland. The camera may be mounted to a macro-viewer camera stand, such as a Polaroid MP4 macro-viewer camera stand, or equivalent. An adjustable lens assembly, such as a Nikon 35-mm lens with an f-stop setting of 4, is attached to the camera via a c-mount connection. The camera is set in monochrome mode and a flat field correction is performed on a white background prior to analysis.

An auto stage including a transparent support is placed on the upper surface of the macro-viewer between the video camera and a diffuse light source of the macro-viewer. The auto stage may be a Design Components Incorporated Model HM-1212 or equivalent. The diffuse, transmitted lighting may be provided by four LED tube lights (EMC-9 watt, dimmable) that are disposed beneath the auto stage, and the macro-viewer includes a diffusing plate located between the LED lights auto stage. The LED light's illumination level can be controlled via a common voltage controller equipped with a knob or slider for adjustments.

Two black masks are placed on the transparent support of the auto stage and spaced three inches apart and having a long dimension running to the front and rear of the auto stage (e.g. toward and away from the camera stand of the macro-viewer). A web sample is placed flat onto the transparent support and centered between the black masks so that only the central region of the sample is illuminated. The web sample is oriented similarly to the black masks with the longitudinally extending side edges (e.g. the long dimension side edges) of the web sample running toward and away from the camera stand. The camera and lens assembly are mounted onto the macro-viewer camera stand at such a distance above the sample that provides an image field-of-view size of approximately 4 and a half inches across a width of the auto stage (e.g. perpendicular to the longitudinally extending side edges of the sample).

Analysis is performed by placing a fibrous web sample onto the auto-stage as described above under the optical axis of the camera and lens assembly. The specimen must lay flat and care is taken to ensure that wrinkles or similar deformities are removed or avoided. An image analysis software package is used to monitor and adjust the illumination level, acquire an image and then perform the measurements for determining gray-level variation. For the analysis described, a Leica Microsystems LAS software platform is used along with the custom-written algorithm Gray Level of CD Variation (Activ Tech)-1 to monitor and adjust the light level of illumination for each sample and perform gray-level variation measurements. The algorithm, which is run using the LAS Macro Editor platform, is shown below.

```
NAME = Gray Level of CD Variation (Activ Tech) - 1
PURPOSE = Measures gray-level values of grid elements across CD
CONDITIONS = DFC 310 camera; 35 mm adj lens (f/4); diffuse transmitted light; pole = 76 cm
AUTHOR = D. G. Biggs
DATE = February 21, 2020
OPEN DATA FILES & SET VARIABLES
```

-continued

```
Pause Text ( "Enter EXCEL data file and image file prefix names now." ) Input ( TITLE$ )
OPENFILE$ = "C:\Data\102888 - Graverson\"+TITLE$+".xls"
Open File ( OPENFILE$, channel #CHAN )
SET Graphics VARIABLES
GRAPHNX = 6
GRAPHNY = 2
GRAPHWID = 790
GRAPHHGHT = 118
GRAPHORGX = 270
GRAPHORGY = 100
GRAPHTHIK = 2
GRAPHORNT = 0
GRAPHOUT = 0
COUNT = 0
SET-UP AND CALIBRATION
Calvalue = 0.0833 mm/px
CALVALUE = 0.0833
Calibration ( Local )
Enter Results Header
File Results Header ( channel #1 )
File Line ( channel #1 )
File Line ( channel #1 )
Image frame ( x 0, y 0, Width 1392, Height 1040 )
Measure frame ( x 260, y 72, Width 806, Height 962 )
SAMPLE LOOP
For (SAMPLE = 1 to 3, step 1)
PauseText ("Place sample onto stage.")
Image Setup DC Twain [PAUSE] (Camera 1, AutoExposure Off, Gain 0.00, Exposure Time 15.69
msec, Brightness 0, Lamp 49.99)
Stage ( Define Origin )
Stage ( Scan Pattern, 1 x 3 fields, size 102000.000000 x 96570.000000 )
IMAGE LOOP
For ( IMAGE = 1 to 3, step 1 )
ACQUIRE IMAGE
Image Setup DC Twain [PAUSE] ( Camera 1, AutoExposure Off, Gain 0.00,
Exposure Time 15.69 msec, Brightness 0, Lamp 49.99 )
Colour Transform ( Mono Mode )
Acquire ( into Image0 )
COUNT = COUNT+1
-- The following line is the image storage location on the hard drive.
ACQFILE$ = "C:\Images\102888 - Graverson\"+TITLE$+"_"+STR$(COUNT)+".tif"
Write image ( from ACQOUTPUT into file ACQFILE$ )
GRAPHORGY = 100
ANALYSIS LOOP
For ( ANALYSIS = 1 to 4, step 1 )
BINARY PROCESSING
Graphics ( Inverted Grid, GRAPHNX x GRAPHNY Lines, Grid Size GRAPHWID x
GRAPHHGHT, Origin GRAPHORGX x GRAPHORGY,
Thickness GRAPHTHIK, Orientation GRAPHORNT, to GRAPHOUT Cleared )
Display ( Image0 (on), frames (on,on), planes (0,off,off,off,off,off), lut 0, x 0, y 0, z 0,
Reduction off )
MEASURE FEATURE GRAY LEVEL
Measure feature ( plane Binary0, 32 ferets, minimum area: 4, grey image: Image0 )
Selected parameters: X FCP, Y FCP, MeanGrey, GreyVarianc
File Feature Results ( channel #1 )
File Line ( channel #1 )
File Line ( channel #1 )
File Line ( channel #1 )
MEASURE GL %COV
MGREYIMAGE = 0
MGREYMASK = 0
Measure Grey ( plane MGREYIMAGE, mask MGREYMASK,
histogram into GREYHIST(256), stats into GREYSTATS(2) )
Selected parameters: MeanGrey, Std Dev
MEANGREY = GREYSTATS(1)
GREYSDEV = GREYSTATS(2)
GLPERCCOV = GREYSDEV/MEANGREY*100
File ( "GL %COV = ", channel #1 )
File ( GLPERCCOV, channel #1, 2 digits after '.' )
File Line ( channel #1 )
File Line ( channel #1 )
GRAPHORGY = GRAPHORGY+250
Next (ANALYSIS)
Stage (Step, Wait until stopped + 550 msecs)
Next (IMAGE)
Next (SAMPLE)
Close File (channel #1)
END
```

Once the algorithm is executed using the Leica software, the analyst will be prompted to enter an EXCEL data file sample and image file prefix name which will be used to store measurement data as well as the image files acquired. Both will be saved onto the computer hard drive. Next, the analyst will be prompted to properly place the sample on the sample stand so that the region to be measured is located between the two black masks. The top edge of the sample should also be located at least an inch or more above the top edge of the field-of-view image. After the sample is properly placed, and the analyst continues the algorithm, the analyst will then be prompted to adjust the illumination level so that the displaying white level is set to approximately 0.95. Once set, the software algorithm then proceeds automatically to acquire and save the image and then perform image processing and analysis steps by placing a five-box grid on the image spanning the width of the sample (e.g. in the CD) and making mean gray and gray variation measurements within each individual box. This data is then exported to the previously named EXCEL spreadsheet and the same grid is again used to measure mean and standard deviation of gray level under the entire grid at one time. From this data, the algorithm then calculates the corresponding gray-level percent coefficient-of-variation (GL % COV) and exports this data to the EXCEL spreadsheet. The GL % COV is calculated as follows:

$$\text{GL \% COV} = \text{gray-level standard deviation}/\text{mean gray-level} \times 100\% \quad (1)$$

The CD-spanning measurement grid is nearly 66 mm across and is subdivided into five equally sized boxes. The mean gray and gray variation measurements are made for each box, while the GL % COV measurement is made for all boxes combined. Once the first measurements are made near the top of an image, the algorithm then moves the grid down 2.1 cm and a second set of measurements are made on the same image and exported to the EXCEL spreadsheet. This is repeated two more times, so that a total of four, CD-running regions are measured for each image. The algorithm then instructs the auto-stage to move the sample longitudinally by 8.2 cm, and the process of setting the white level for the next image begins again. For each sample replicate, three separate images will be acquired and analyzed. A total of three sample replicate pieces are then analyzed per sample.

For gray-level variation measurements, the five measurements made for each grid location are subsequently averaged in the EXCEL spreadsheet. These averages are then accumulated over 36 different grid positions (i.e. 3 replicates×3 images×4 CD locations=36 CD locations) for comparing different samples. After results are acquired from different samples, they can be compared to one another by performing a basic statistical analysis, such as a Student's T analysis at the 90% confidence level.

Adhesive Distribution Test Method

Samples to be imaged are first stained with osmium tetroxide fume so that the adhesive selectively absorbs the osmium in sufficient quantities to allow it to be more easily contrasted from the super absorbent and polymeric fibers during Micro-CT imaging. A sample is stained by placing it in a closable, air-tight chamber to which a small vial of osmium tetroxide is added. The chamber is then immediately sealed and the osmium tetroxide is allowed to interact with the sample for at least 24 hours. Since osmium tetroxide is highly toxic, the staining procedure is carried out in a fume hood. After the 24 hour period, the adhesive should become blackened in appearance. After re-opening the chamber, it is allowed to air out in the hood for another 24 hours to ensure any unreacted osmium tetroxide is allowed to harmlessly escape. After the second 24 hour period, the sample is now ready to be imaged in the Micro-CT, A Bruker SkyScan Model 1272 Micro-CT, or equivalent, is used to image a portion of the stained sample. Example X-ray scanning conditions include the following:

Voltage (kV)=35
Current (uA)=231
Image Pixel Size (um)=8.0
Rotation Step (deg)=0.20
Frame Averaging=5

The sample piece must be oriented so that machine-direction length is held in the vertical position during the scanning process. After initial x-ray scanning, the rotational x-ray images are then reconstructed using Bruker's NRecon software, or equivalent on a different vendor's system. The gray-scale reconstructed image slices are used for the adhesive distribution analysis.

The image analysis software platform used to perform the adhesive distribution measurements may be a QWIN Pro (Version 3.2.1) available from Leica Microsystems, having an office in Heerbrugg, Switzerland. The custom-written image analysis algorithm 'Z-Adhesive Distribution' was used to process and perform measurements of grayscale Micro-CT images using Quantimet User Interactive Programming System (QUIPS) language. The custom image analysis algorithm shown below was performed directly on the gray-scale reconstructed image slices that were stored on a storage device. The custom image analysis algorithm is shown below.

```
NAME: Z-Adhesive Distribution
PURPOSE: Measures z-distribution of osmium stained adhesive on ActivTech/Blizzard Substrates
CONDITIONS: Images acquired on the Bruker SkyScan 1272 Micro-CT
DATE: August 12, 2020
AUTHOR: D. G. Biggs
SET-UP
Clear Accepts
DATA FILES OPENED
Open File ( C:\Data\102888 - Graverson\totdistribution.xls, channel #2 )
Open File ( C:\Data\102888 - Graverson\adhesivedistribution.xls, channel #1 )
Configure ( Image Store 1968 x 504, Grey Images 201, Binaries 32 )
-- Calvalue = 8.00 um/px
CALVALUE = 8.00
Calibrate ( CALVALUE CALUNITS$ per pixel )
Measure frame ( x 160, y 2, Width 1600, Height 502 )
Image frame ( x 0, y 0, Width 1968, Height 504 )
Enter Results Header
File Results Header ( channel #1 )
File Line ( channel #1 )
```

-continued

```
File Results Header ( channel #2 )
File Line ( channel #2 )
PauseText ( "Enter sample image file prefix name." )
Input ( TITLE$ )
File ( TITLE$, channel #1 )
File Line ( channel #1 )
For ( IMAGE = 100 to 900, step 100 )
Clear Feature Histogram #1
Clear Feature Histogram #3
DEFINE BINARY GRAPHICS VARIABLES
GRAPHORGX = 250
IMAGE ACQUISITION AND DETECTION
ACQOUTPUT = 0
-- Location of Micro-CT images to be analyzed
ACQFILE$ = "C:\Images\102888 - Graverson\Code 2 - Blizzard Tech
Osmium\"+TITLE$+""+STR$(IMAGE)+".JPG"
Read image ( from file ACQFILE$ into ACQOUTPUT )
Colour Transform ( Mono Mode )
-- Detect all material
Detect ( whiter than 33, from Image0 into Binary0 )
IMAGE PROCESSING
PauseText ( "Accept the primary structure and exclude any outlying debris." )
Binary Edit [PAUSE] ( Accept from Binary0 to Binary1, nib Fill, width 2 )
Binary Amend ( Open from Binary1 to Binary1, cycles 1, operator Disc, edge erode on )
Binary Amend ( Close from Binary1 to Binary2, cycles 120, operator Disc, edge erode on )
Binary Identify ( FillHoles from Binary2 to Binary3 )
Binary Amend ( Open from Binary3 to Binary4, cycles 5, operator Disc, edge erode on )
BOLEAN AND MEASUREMENT
For ( BINGRAPH = 1 to 26, step 1 )
GRAPHORGY = 2
GRAPHNX = 1
GRAPHNY = 1
GRAPHWID = 50
GRAPHHGHT = 502
GRAPHTHIK = 1
GRAPHORNT = 0
GRAPHOUT = 13
Graphics ( Inverted Grid, GRAPHNX x GRAPHNY Lines, Grid Size GRAPHWID x GRAPHHGHT,
Origin GRAPHORGX x GRAPHORGY,
Thickness GRAPHTHIK, Orientation GRAPHORNT, to GRAPHOUT Cleared )
Binary Logical ( C = A AND B : C Binary5, A Binary4, B Binary13 )
CENTER YPOS
Measure feature ( plane Binary5, 32 ferets, minimum area: 10, grey image: Colour0 )
Selected parameters: UserDef1, YCentroid
Feature Expression ( UserDef1 ( all features ), title CalcA = (PYCENTROID(FTR)-252) )
GREYUTILIN = 0
GREYUTILOUT = 1
-- Shift Grey Image
If ( PUSERDEF1(FTR)<0 )
DISTANCE = (PUSERDEF1(FTR)**2)**0.5
SHIFT.SIZE = DISTANCE
SHIFT.DIRN = 270
Grey Util ( Shift GREYUTILIN to GREYUTILOUT by SHIFT.SIZE at SHIFT.DIRN degs )
Endif
If ( PUSERDEF1(FTR)>0 )
DISTANCE = PUSERDEF1 (FTR)
SHIFT.SIZE = DISTANCE
SHIFT.DIRN = 90
Grey Util ( Shift GREYUTILIN to GREYUTILOUT by SHIFT.SIZE at SHIFT.DIRN degs )
Endif
If ( PUSERDEF1(FTR)=0 )
Grey Util ( Copy Image0 to Image1 )
Endif
Display ( Image0 (on), frames (on,on), planes (off,off,off,off,off,off), lut 0, x 0, y 0, z 1, Reduction off )
DETECT AFTER CENTERING
-- Detect adhesive
Detect ( whiter than 84, from Image1 into Binary10 )
Binary Amend ( Close from Binary10 to Binary10, cycles 1, operator Disc, edge erode on )
Binary Amend ( Open from Binary10 to Binary11, cycles 1, operator Disc, edge erode on )
-- Detect all material
Detect ( whiter than 33, from Image1 into Binary0 )
Binary Amend ( Close from Binary0 to Binary0, cycles 1, operator Disc, edge erode on )
Binary Amend ( Open from Binary0 to Binary0, cycles 1, operator Disc, edge erode on )
MEASURE ADHESIVE Z-DISTRIBUTION
GRAPHORGY = 2
GRAPHNX = 1
GRAPHNY = 1
GRAPHWID = 50
GRAPHHGHT = 502
```

-continued

```
GRAPHTHIK = 1
GRAPHORNT = 0
GRAPHOUT = 12
Graphics ( Inverted Grid, GRAPHNX x GRAPHNY Lines, Grid Size GRAPHWID x GRAPHHGHT,
Origin GRAPHORGX x GRAPHORGY,
Thickness GRAPHTHIK, Orientation GRAPHORNT, to GRAPHOUT Cleared )
Binary Logical ( C = A AND B : C Binary6, A Binary12, B Binary11 )
Measure feature ( plane Binary6, 32 ferets, minimum area: 10, grey image: Image1 )
Selected parameters: Area, UserDef2, YCentroid
Feature Expression ( UserDef2 ( all features ), title YFEAT = PYCENTROID(FTR)*CALVALUE )
Feature Histogram #1 ( Y Param Area, X Param UserDef2, from 0. to 4032., linear, 40 bins )
Feature Histogram #2 ( Y Param Area, X Param UserDef2, from 0. to 4032., linear, 40 bins )
MEASURE TOTAL MATERIAL Z-DISTRIBUTION
Binary Logical (C = A AND B : C Binary7, A Binary12, B Binary0 )
Measure feature ( plane Binary7, 32 ferets, minimum area: 10, grey image: Image1 )
Selected parameters: Area, X FCP, Y FCP, UserDef2, YCentroid
Feature Expression ( UserDef2 ( all features ), title YFEAT = PYCENTROID(FTR)*CALVALUE )
Feature Histogram #3 ( Y Param Area, X Param UserDef2, from 0. to 4032., linear, 40 bins )
Feature Histogram #4 ( Y Param Area, X Param UserDef2, from 0. to 4032., linear, 40 bins )
GRAPHORGX = GRAPHORGX+50
Next ( BINGRAPH )
Display Feature Histogram Results ( #2, horizontal, differential, bins + graph (Y axis linear), statistics
)
Data Window ( 10, 871, 640, 300 )
Display Feature Histogram Results ( #4, horizontal, differential, bins + graph (Y axis linear), statistics
)
Data Window ( 962, 880, 640, 300 )
FILE ADHESIVE AND MATERIAL HISTOGRAMS FOR CURRENT IMAGE
File Feature Histogram Results ( #1, differential, statistics, bin details, channel #1 )
File Line ( channel #1 )
File Feature Histogram Results ( #3, differential, statistics, bin details, channel #2 )
File Line ( channel #2 )
File Line ( channel #2 )
MEASURE MEAN SUBSTRATE THICKNESS
MFLDIMAGE = 4
Measure field ( plane MFLDIMAGE, into FLDRESULTS(1), statistics into FLDSTATS(7,1) )
Selected parameters: Area
MEANTHICK = FLDRESULTS(1)/(CALVALUE*1330)
File ( "Mean Substrate Thickness (um) = ", channel #1 )
File ( MEANTHICK, channel #1, 2 digits after '.' )
File Line ( channel #1 )
File Line ( channel #1 )
Next ( IMAGE )
FILE CUMMULATIVE ADHESIVE AND MATERIAL HISTOGRAMS FOR CURRENT SLIDE
File Feature Histogram Results ( #2, differential, statistics, bin details, channel #1 )
File Feature Histogram Results ( #4, differential, statistics, bin details, channel #2 )
CLOSE DATA FILES
Close File ( channel #1 )
Close File ( channel #2 )
END
```

The adhesive distribution in the z-direction data are exported directly to an EXCEL® spreadsheet. Individual adhesive and total material z-distribution histograms are exported for data acquired from each of the analyzed slices of the micro-CT image as well as a cumulative histogram for data from all nine slices. These latter cumulative histograms were used for calculating the percentage of adhesive in each one-third layer of the thickness of the micro-CT image for a single slice. The area units are shown in the histogram are in square microns. In order to determine the histogram location of the top and bottom surface boundaries of the material, a 95 percent of total area rule was used on the total material histogram. In other words, when approaching the top and bottom material edges of the histogram, the surface boundary was considered to be the first histogram bin when a minimum of 2.5 percent material area had been encountered. These bin boundaries were then transposed over to the adhesive only cumulative histogram to determine the percentages of adhesive area present in the top, middle and bottom one-third histogram bins, inclusive of the calculated boundary bins. In cases where the number of bins was not evenly divisible by three (e.g. 8, 10, 14, etc.), a rotation technique was used to calculate adhesive percentages in each one-third layer of the material. For example, in the first encounter of a fourteen bin thickness, the top layer was four bins, the middle five, and the bottom five. During the next encounter, the top layer was five bins, the middle four, and the bottom five. If a third encounter occurs, the bottom layer would have one less or one more bin than the top and middle. If a fourth encounter occurs, the top layer again becomes the one containing one less or one more bin than the other two layers. This rotating method continues as required by the data.

The final sample mean adhesive percentage values for each one-third layer of z-distribution depth is based on an N=7 analysis from seven, separate, subsample regions each possessing four adjacently cut cross-sections. A comparison between different samples can be performed using a Student's T analysis at the 90 percent confidence level.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Embodiments

In a first embodiment, an absorbent structure having a longitudinal axis and a lateral axis may comprise a first substrate material layer having a first surface and a second surface, a second substrate material layer having a first surface and a second surface, and a mixture of superabsorbent particles and adhesive disposed between the first substrate material layer and the second substrate material layer, wherein the superabsorbent particles are disposed in an amount greater than or equal to 400 gsm and less than or equal to 600 gsm, and wherein the adhesive is disposed in an amount greater than or equal to 4% and less than or equal to 6%, by weight, of the weight of the superabsorbent particles, wherein the adhesive forms a three-dimensional mesh network comprising network adhesive filaments with the superabsorbent particles immobilized within the mesh network, and the network adhesive filaments extending substantially throughout a three-dimensional space defined by the network adhesive filaments and the superabsorbent particles, and wherein the absorbent structure has a Gray Level % Coefficient of Variability value (GL % COV) of less than or equal to 34.5, according to the Pad Uniformity Test Method.

In a second embodiment, the absorbent structure of the first embodiment may further comprise wherein the absorbent structure has a Gray Level % Coefficient of Variability value (GL % COV) of less than or equal to 33.5, according to the Pad Uniformity Test Method.

In a third embodiment, the absorbent structure of any of the first or second embodiments may further comprise wherein the superabsorbent particles are disposed in an amount greater than or equal to 400 gsm and less than or equal to 500 gsm.

In a fourth embodiment, the absorbent structure of any one of the first through third embodiments may further comprise wherein the absorbent structure does not comprise an adhesive layer disposed between at least one of: the first substrate material layer and the mixture of superabsorbent particles and adhesive; and, the second substrate material layer and the mixture of superabsorbent particles and adhesive.

In a fifth embodiment, the absorbent structure of any one of the first through fourth embodiments may further comprise wherein the network adhesive filaments contact substantially all of the superabsorbent particles of the mixture of superabsorbent particles and adhesive.

In a sixth embodiment, an absorbent structure having a longitudinal axis and a lateral axis may comprise a first substrate material layer having a first surface and a second surface, a second substrate material layer having a first surface and a second surface, and a mixture of superabsorbent particles and adhesive disposed between the first substrate material layer and the second substrate material layer, the superabsorbent particles being disposed in an amount greater than or equal to 400 gsm and less than or equal to 500 gsm, and wherein the adhesive is disposed in an amount greater than or equal to 4% and less than or equal to 6%, by weight, of the weight of the superabsorbent particles, wherein the adhesive forms a three-dimensional mesh network comprising network adhesive filaments with the superabsorbent particles immobilized within the mesh network, and the network adhesive filaments extending substantially throughout a three-dimensional space defined by the network adhesive filaments and the superabsorbent particles, and wherein the absorbent structure has a CD Gray Level Variability (CD GL Var.) values less than or equal to 510, according to the Pad Uniformity Test.

In a seventh embodiment, the absorbent structure of the sixth embodiment may further comprise wherein the absorbent structure has a CD Gray Level Variability (CD GL Var.) values less than or equal to 490, according to the Pad Uniformity Test.

In an eighth embodiment, the absorbent structure of the sixth or seventh embodiments may further comprise wherein the absorbent structure does not comprise an adhesive layer disposed between at least one of: the first substrate material layer and the mixture of superabsorbent particles and adhesive; and, the second substrate material layer and the mixture of superabsorbent particles and adhesive.

In a ninth embodiment, the absorbent structure of any one of the sixth through eighth embodiments may further comprise wherein the network adhesive filaments contact substantially all of the superabsorbent particles of the mixture of superabsorbent particles and adhesive.

In a tenth embodiment, a method of manufacturing an absorbent structure may comprise: feeding a first stream of superabsorbent particles toward a first substrate material layer moving in a machine direction, the first stream of superabsorbent particles having a first side and a second side, spraying, with a first adhesive applicator having a first adhesive nozzle, the first side of the first stream of superabsorbent particles with a first adhesive, the first adhesive contacting the first stream of superabsorbent particles and intermixing with the superabsorbent particles of the first stream of superabsorbent particles prior to said superabsorbent particles depositing onto the first substrate material layer, the first adhesive contacting the first stream of superabsorbent particles at a first contact point having a first height as measured from the first substrate material layer, spraying, with a second adhesive applicator having a second adhesive nozzle, the second side of the first stream of superabsorbent particles with a second adhesive, the second adhesive contacting the first stream of superabsorbent particles and intermixing with the superabsorbent particles of the first stream of superabsorbent particles prior to said superabsorbent particles depositing onto the first substrate material layer, the second adhesive contacting the first stream of superabsorbent particles at a second contact point having a second height as measured from the first substrate material layer, depositing the intermixed superabsorbent particles of the first stream of superabsorbent particles, first adhesive, and second adhesive onto the first substrate material layer, covering the mixture of the superabsorbent particles of the first stream of superabsorbent particles, the first adhesive, and the second adhesive with a second substrate material layer, and separating the mixture of the superabsorbent particles, adhesive, the first substrate material layer, and the second substrate material layer into individual absorbent structures, wherein absorbent structures produced by this method having superabsorbent particles disposed in an amount equal to 300 gsm and adhesive disposed in an amount greater than 3% and less than 4%, by weight, of the weight of the superabsorbent particles, have CD Gray Level Variability (CD GL Var.) values less than or equal to 675, according to the Pad Uniformity Test.

In an eleventh embodiment, the method of the tenth embodiment may further comprise wherein absorbent structures produced by this method having superabsorbent particles disposed in an amount equal to 300 gsm and adhesive disposed in an amount greater than 3% and less than 4%, by weight, of the weight of the superabsorbent particles, have CD Gray Level Variability (CD GL Var.) values less than or equal to 625, according to the Pad Uniformity Test.

In a twelfth embodiment, the method of the tenth or eleventh embodiments may further comprise wherein absorbent structures produced by this method having superabsorbent particles disposed in an amount equal to 400 gsm and adhesive disposed in an amount greater than 4% and less than 5%, by weight, of the weight of the superabsorbent particles, have CD Gray Level Variability (CD GL Var.) values less than or equal to 585, according to the Pad Uniformity Test.

In a thirteenth embodiment, the method of any one of the tenth through twelfth embodiments may further comprise wherein absorbent structures produced by this method having superabsorbent particles disposed in an amount equal to 400 gsm and adhesive disposed in an amount greater than 4% and less than 5%, by weight, of the weight of the superabsorbent particles, have CD Gray Level Variability (CD GL Var.) values less than or equal to 500, according to the Pad Uniformity Test.

In a fourteenth embodiment, the method of any one of the tenth through thirteenth embodiments may further comprise wherein absorbent structures produced by this method having superabsorbent particles disposed in an amount equal to 500 gsm and adhesive disposed in an amount of 6%, by weight, of the weight of the superabsorbent particles, have CD Gray Level Variability (CD GL Var.) values less than or equal to 500, according to the Pad Uniformity Test.

In a fifteenth embodiment, the method of any one of the tenth through fourteenth embodiments may further comprise wherein absorbent structures produced by this method having superabsorbent particles disposed in an amount equal to 600 gsm and adhesive disposed in an amount of 6%, by weight, of the weight of the superabsorbent particles, have CD Gray Level Variability (CD GL Var.) values less than or equal to 450, according to the Pad Uniformity Test.

In a sixteenth embodiment, the method of any one of the tenth through fifteenth embodiments may further comprise wherein the first height is different than the second height.

In a seventeenth embodiment, the method of any one of the tenth through sixteenth embodiments may further comprise wherein the first height is located between 4 mm and 40 mm from the first substrate material.

In an eighteenth embodiment, the method of any one of the tenth through sixteenth embodiments, may further comprise wherein the first height is spaced from the second height by between 3 mm and 9.5 mm.

In a nineteenth embodiment, the method of any one of the tenth through eighteenth embodiments may further comprise, prior to covering the mixture of the superabsorbent particles of the first stream of superabsorbent particles, the first adhesive, and the second adhesive with a second substrate material layer: feeding a second stream of superabsorbent particles toward the deposited mixture of the superabsorbent particles of the first stream of superabsorbent particles and the first adhesive, the second stream of superabsorbent particles having a first side and a second side, spraying, with a third adhesive applicator having a third adhesive nozzle, the first side of the second stream of superabsorbent particles with a third adhesive, the third adhesive contacting the second stream of superabsorbent particles and intermixing with the superabsorbent particles of the second stream of superabsorbent particles prior to said superabsorbent particles depositing onto the deposited mixture of the superabsorbent particles of the first stream of superabsorbent particles, the first adhesive, and the second adhesive, spraying, with a fourth adhesive applicator having a fourth adhesive nozzle, the second side of the second stream of superabsorbent particles with a fourth adhesive, the fourth adhesive contacting the second stream of superabsorbent particles and intermixing with the superabsorbent particles of the second stream of superabsorbent particles prior to said superabsorbent particles depositing onto the deposited mixture of the superabsorbent particles of the first stream of superabsorbent particles, the first adhesive, and the second adhesive, depositing the intermixed superabsorbent particles of the second stream of superabsorbent particles, the second adhesive, and the fourth adhesive onto the deposited mixture of the superabsorbent particles of the first stream of superabsorbent particles, the first adhesive, and the third adhesive, covering both the deposited mixtures of the superabsorbent particles of the first stream of superabsorbent particles, the first adhesive, and the third adhesive and the superabsorbent particles of the second stream of superabsorbent particles, the second adhesive, and the fourth adhesive with a second substrate material layer, and separating the deposited mixtures of the superabsorbent particles, adhesives, the first substrate material layer, and the second substrate material layer into individual absorbent structures.

In a twentieth embodiment, the method of the nineteenth embodiment may further comprise wherein the third adhesive contacts the second stream of superabsorbent particles at a third contact point having a third height as measured from the first substrate material layer, the fourth adhesive contacts the second stream of superabsorbent particles at a fourth contact point having a fourth height as measured from the first substrate material layer, and the third height being different from the fourth height.

What is claimed is:

1. A method of manufacturing an absorbent structure, the method comprising:

feeding a first stream of superabsorbent particles toward a first substrate material layer moving in a machine direction, the first stream of superabsorbent particles having a first side and a second side;

forming a mixture of superabsorbent particles, a first adhesive, and a second adhesive by:

spraying, with a first adhesive applicator having a first adhesive nozzle, the first side of the first stream of superabsorbent particles with the first adhesive, the first adhesive contacting the first stream of superabsorbent particles and intermixing with the superabsorbent particles of the first stream of superabsorbent particles prior to said superabsorbent particles depositing onto the first substrate material layer, the first adhesive contacting the first stream of superabsorbent particles at a first contact point having a first height as measured from the first substrate material layer, and spraying, with a second adhesive applicator having a second adhesive nozzle, the second side of the first stream of superabsorbent particles with the second adhesive, the second adhesive contacting the first stream of superabsorbent particles and intermixing with the superabsorbent particles of the first stream of superabsorbent particles prior to said superabsorbent particles depositing onto the first substrate material layer, the second adhesive contacting the first stream of superabsorbent particles at a second contact point having a second height as measured from the first substrate material layer;

forming a layered assembly by:

depositing the mixture onto the first substrate material layer, and covering the mixture with a second substrate material layer; and separating the layered assembly into individual absorbent structures, wherein absorbent structures produced by this method with superabsorbent particles disposed in an amount equal to 300 gsm and with adhesive disposed in an amount greater than 3% and less than 4%, by weight, of the weight of the superabsorbent particles, have CD Gray Level Variability (CD GL Var.) values less than or equal to 675, according to the Pad Uniformity Test.

2. The method of claim 1, wherein absorbent structures produced by this method with superabsorbent particles disposed in an amount equal to 300 gsm and with adhesive disposed in an amount greater than 3% and less than 4%, by weight, of the weight of the superabsorbent particles, have CD Gray Level Variability (CD GL Var.) values less than or equal to 625, according to the Pad Uniformity Test.

3. The method of claim 1, wherein the first height is different than the second height.

4. The method of claim 3, wherein the first height is located between 4 mm and 40 mm from the first substrate material.

5. The method of claim 3, wherein the first height is spaced from the second height by between 3 mm and 9.5 mm.

6. The method of claim 1, wherein the mixture is a first mixture;

the method further comprising, prior to covering the first mixture with the second substrate material layer:

feeding a second stream of superabsorbent particles toward the first substrate material layer with the first mixture, the second stream of superabsorbent particles having a third side and a fourth side;

forming a second mixture of superabsorbent particles, a third adhesive, and a fourth adhesive by:

spraying, with a third adhesive applicator having a third adhesive nozzle, the third side of the second stream of superabsorbent particles with the third adhesive, the third adhesive contacting the second stream of superabsorbent particles and intermixing with the superabsorbent particles of the second stream of superabsorbent particles prior to said superabsorbent particles depositing onto the first mixture, and spraying, with a fourth adhesive applicator having a fourth adhesive nozzle, the fourth side of the second stream of superabsorbent particles with the fourth adhesive, the fourth adhesive contacting the second stream of superabsorbent particles and intermixing with the superabsorbent particles of the second stream of superabsorbent particles prior to said superabsorbent particles depositing onto the first mixture; and depositing the second mixture onto the first mixture; and wherein the covering the first mixture includes covering the second mixture with the second substrate material layer.

7. The method of claim 6, wherein the third adhesive contacts the second stream of superabsorbent particles at a third contact point having a third height as measured from the first substrate material layer, the fourth adhesive contacts the second stream of superabsorbent particles at a fourth contact point having a fourth height as measured from the first substrate material layer, and the third height being different from the fourth height.

8. A method of manufacturing an absorbent structure, the method comprising:

feeding a first stream of superabsorbent particles toward a first substrate material layer moving in a machine direction, the first stream of superabsorbent particles having a first side and a second side;

forming a mixture of superabsorbent particles, a first adhesive, and a second adhesive by:

spraying, with a first adhesive applicator having a first adhesive nozzle, the first side of the first stream of superabsorbent particles with the first adhesive, the first adhesive contacting the first stream of superabsorbent particles and intermixing with the superabsorbent particles of the first stream of superabsorbent particles prior to said superabsorbent particles depositing onto the first substrate material layer, the first adhesive contacting the first stream of superabsorbent particles at a first contact point having a first height as measured from the first substrate material layer, and spraying, with a second adhesive applicator having a second adhesive nozzle, the second side of the first stream of superabsorbent particles with the second adhesive, the second adhesive contacting the first stream of superabsorbent particles and intermixing with the superabsorbent particles of the first stream of superabsorbent particles prior to said superabsorbent particles depositing onto the first substrate material layer, the second adhesive contacting the first stream of superabsorbent particles at a second contact point having a second height as measured from the first substrate material layer;

forming a layered assembly by:

depositing the mixture onto the first substrate material layer, and covering the mixture with a second substrate material layer; and separating the layered assembly into individual absorbent structures, wherein absorbent structures produced by this method with superabsorbent particles disposed in an amount equal to 400 gsm and with adhesive disposed in an amount greater than 4% and less than 5%, by weight, of the weight of the superabsorbent particles have CD Gray Level Variability (CD GL Var.) values less than or equal to 585, according to the Pad Uniformity Test.

9. The method of claim 8, wherein absorbent structures produced by this method with superabsorbent particles disposed in an amount equal to 400 gsm and with adhesive disposed in an amount greater than 4% and less than 5%, by weight, of the weight of the superabsorbent particles have CD Gray Level Variability (CD GL Var.) values less than or equal to 500, according to the Pad Uniformity Test.

10. The method of claim 8, wherein the first height is different than the second height.

11. The method of claim 10, wherein the first height is located between 4 mm and 40 mm from the first substrate material.

12. The method of claim 10, wherein the first height is spaced from the second height by between 3 mm and 9.5 mm.

13. The method of claim 8, wherein the mixture is a first mixture;

the method further comprising, prior to covering the first mixture with the second substrate material layer:

feeding a second stream of superabsorbent particles toward the first substrate material layer with the first mixture, the second stream of superabsorbent particles having a third side and a fourth side;

forming a second mixture of superabsorbent particles, a third adhesive, and a fourth adhesive by:

spraying, with a third adhesive applicator having a third adhesive nozzle, the third side of the second stream of superabsorbent particles with the third adhesive, the third adhesive contacting the second stream of superabsorbent particles and intermixing with the superabsorbent particles of the second stream of superabsorbent particles prior to said superabsorbent particles depositing onto the first mixture, and spraying, with a fourth adhesive applicator having a fourth adhesive nozzle, the fourth side of the second stream of superabsorbent particles with the fourth adhesive, the fourth adhesive contacting the second stream of superabsorbent particles and intermixing with the superabsorbent particles of the second stream of superabsorbent particles prior to said superabsorbent particles depositing onto the first mixture; and depositing the second mixture onto the first mixture; and wherein the covering the first mixture includes covering the second mixture with the second substrate material layer.

14. The method of claim 13, wherein the third adhesive contacts the second stream of superabsorbent particles at a third contact point having a third height as measured from the first substrate material layer, the fourth adhesive contacts the second stream of superabsorbent particles at a fourth contact point having a fourth height as measured from the first substrate material layer, and the third height being different from the fourth height.

15. A method of manufacturing an absorbent structure, the method comprising:

feeding a first stream of superabsorbent particles toward a first substrate material layer moving in a machine direction, the first stream of superabsorbent particles having a first side and a second side;

forming a mixture of superabsorbent particles, a first adhesive, and a second adhesive by:

spraying, with a first adhesive applicator having a first adhesive nozzle, the first side of the first stream of superabsorbent particles with the first adhesive, the first adhesive contacting the first stream of superabsorbent particles and intermixing with the superabsorbent particles of the first stream of superabsorbent particles prior to said superabsorbent particles depositing onto the first substrate material layer, the first adhesive contacting the first stream of superabsorbent particles at a first contact point having a first height as measured from the first substrate material layer, and spraying, with a second adhesive applicator having a second adhesive nozzle, the second side of the first stream of superabsorbent particles with the second adhesive, the second adhesive contacting the first stream of superabsorbent particles and intermixing with the superabsorbent particles of the first stream of superabsorbent particles prior to said superabsorbent particles depositing onto the first substrate material layer, the second adhesive contacting the first stream of superabsorbent particles at a second contact point having a second height as measured from the first substrate material layer;

forming a layered assembly by:

depositing the mixture onto the first substrate material layer, and covering the mixture with a second substrate material layer; and separating the layered assembly into individual absorbent structures, wherein absorbent structures produced by this method with superabsorbent particles disposed in an amount equal to 500 gsm and with adhesive disposed in an amount of 6%, by weight, of the weight of the superabsorbent particles have CD Gray Level Variability (CD GL Var.) values less than or equal to 500, according to the Pad Uniformity Test.

* * * * *